United States Patent

Doherty et al.

[11] Patent Number: 6,008,372
[45] Date of Patent: Dec. 28, 1999

[54] SUBSTITUTED DINAPHTHYLMETHYL AND DIHETEROARYLMETHYLACETYL HISTIDINE INHIBITORS OF PROTEIN FARNESYLTRANSFERASE

[75] Inventors: Annette M. Doherty; James S. Kaltenbronn; Daniele Leonard; John Quin, III, all of Ann Arbor; Jeffrey D. Scholten, Brighton, all of Mich.

[73] Assignee: Warner-Lambert Company, Morris Plains, N.J.

[21] Appl. No.: 09/101,206

[22] PCT Filed: Jan. 2, 1997

[86] PCT No.: PCT/US97/00265

§ 371 Date: Jul. 2, 1998

§ 102(e) Date: Jul. 2, 1998

[87] PCT Pub. No.: WO97/26246

PCT Pub. Date: Jul. 24, 1997

Related U.S. Application Data

[60] Provisional application No. 60/009,956, Jan. 16, 1996.

[51] Int. Cl.$^6$ ................. C07D 233/64; C07D 409/12; C07D 413/12; C07D 409/14; A61K 31/41; A61K 31/535

[52] U.S. Cl. ................. 548/338.1; 514/396; 514/397; 514/398; 514/399; 514/400; 514/235.8; 548/338.5; 548/346.1; 548/312.7; 548/311.1; 548/314.4; 544/139

[58] Field of Search ............... 548/338.1, 338.5, 548/312.7, 346.1, 311.1, 314.4; 514/398, 399, 396, 397, 400, 235.8; 544/139

[56] References Cited

U.S. PATENT DOCUMENTS

| | | | |
|---|---|---|---|
| 4,870,183 | 9/1989 | Iizuka et al. | 546/210 |
| 4,904,660 | 2/1990 | Nakano et al. | 514/236.2 |
| 5,098,923 | 3/1992 | Karjalainen et al. | 514/396 |
| 5,223,489 | 6/1993 | Hemmi et al. | 514/19 |
| 5,541,213 | 7/1996 | Matsukura et al. | 514/400 |
| 5,571,792 | 11/1996 | Bolton et al. | 514/18 |

*Primary Examiner*—Floyd D. Higel
*Attorney, Agent, or Firm*—Francis J. Tinney

[57] ABSTRACT

Substituted histidine compounds of formula (I) are described as well as methods for the preparation and pharamaceutical compositions of same, which are useful as inhibitors of protein farnesyltransferase and for the treatment of proliferative diseases including cancer, restenosis, and psoriasis, and as antiviral agents.

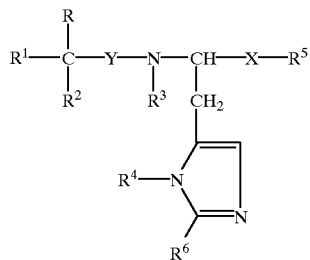

14 Claims, No Drawings

SUBSTITUTED DINAPHTHYLMETHYL AND DIHETEROARYLMETHYLACETYL HISTIDINE INHIBITORS OF PROTEIN FARNESYLTRANSFERASE

This application is a 371 of PCT/US97/00265 filed Jan. 2, 1997, and this application claims the benefit of U.S. Provisional Application No. 60/009,956 filed Jan. 16, 1996.

BACKGROUND OF THE INVENTION

The present invention relates to novel substituted histidine compounds useful as pharmaceutical agents, to methods for their production, to pharmaceutical compositions which include these compounds and a pharmaceutically acceptable carrier, and to pharmaceutical methods of treatment. The novel compounds of the present invention inhibit farnesyl transferase enzyme which activates ras proteins which in turn activate cellular division. More particularly, the novel compounds of the present invention are useful in the treatment of proliferative diseases such as, for example, cancer, restenosis, and psoriasis, and as antiviral agents.

Ras protein (or p21) has been examined extensively because mutant forms are found in 20% of most types of human cancer and greater than 50% of colon and pancreatic carcinomas (Gibbs J. B., Cell, 65:1 (1991), Cartwright T., et al., Chimica. Oggi., 10:26 (1992)). These mutant ras proteins are deficient in the capability for feedback regulation that is present in native ras and this deficiency is associated with their oncogenic action since the ability to stimulate normal cell division cannot be controlled by the normal endogenous regulatory cofactors. The recent discovery that the transforming activity of mutant ras is critically dependent on post-translational modifications (Gibbs J., et al., Microbiol. Rev., 53:171 (1989)) has unveiled an important aspect of ras function and identified novel prospects for cancer therapy.

In addition to cancer, there are other conditions of uncontrolled cellular proliferation that may be related to excessive expression and/or function of native ras proteins. Post-surgical vascular restenosis is such a condition. The use of various surgical revascularization techniques such as saphenous vein bypass grafting, endarterectomy and transluminal coronary angioplasty is often accompanied by complications due to uncontrolled growth of neointimal tissue, known as restenosis. The biochemical causes of restenosis are poorly understood and numerous growth factors and protooncogenes have been implicated (Naftilan A. J., et al., Hypertension, 13:706 (1989) and J. Clin. Invest., 83:1419; Gibbons G. H., et al., Hypertension, 14:358 (1989); Satoh T., et al., Mollec. Cell. Biol., 13:3706 (1993)). The fact that ras proteins are known to be involved in cell division processes makes them a candidate for intervention in many situations where cells are dividing uncontrollably. In direct analogy to the inhibition of mutant ras related cancer, blockade of ras dependent processes has the potential to reduce or eliminate the inappropriate tissue proliferation associated with restenosis, particularly in those instances where normal ras expression and/or function is exaggerated by growth stimulatory factors.

Ras functioning is dependent upon the modification of the proteins in order to associate with the inner face of plasma membranes. Unlike other membrane-associated proteins, ras proteins lack conventional transmembrane or hydrophobic sequences and are initially synthesized in a cytosol soluble form. Ras protein membrane association is triggered by a series of post-translational processing steps that are signaled by a carboxyl terminal amino acid consensus sequence that is recognized by protein farnesyltransferase (PFT). This consensus sequence consists of a cysteine residue located four amino acids from the carboxyl terminus, followed by two lipophilic amino acids and the C-terminal residue. The sulfhydryl group of the cysteine residue is alkylated by farnesylpyrophosphate in a reaction that is catalyzed by protein farnesyltransferase. Following prenylation, the C-terminal three amino acids are cleaved by an endoprotease and the newly exposed alpha-carboxyl group of the prenylated cysteine is methylated by a methyl transferase. The enzymatic processing of ras proteins that begins with farnesylation enables the protein to associate with the cell membrane. Mutational analysis of oncogenic ras proteins indicate that these post-translational modifications are essential for transforming activity. Replacement of the consensus sequence cysteine residue with other amino acids gives a ras protein that is no longer farnesylated, fails to migrate to the cell membrane and lacks the ability to stimulate cell proliferation (Hancock J. F., et al., Cell, 57:1167 (1989), Schafer W. R., et al., Science, 245:379 (1989), Casey P. J., Proc. Natl. Acad. Sci. USA, 86:8323 (1989)).

Recently, protein farnesyltransferases (PFTs, also referred to as farnesyl proteintransferases (FPTs) have been identified and a specific PFT from rat brain was purified to homogeneity (Reiss Y., et al., Bioch. Soc. Trans., 20:487–88 (1992)). The enzyme was characterized as a heterodimer composed of one alpha-subunit (49 kDa) and one beta-subunit (46 kDa), both of which are required for catalytic activity. High level expression of mammalian PFT in a baculovirus system and purification of the recombinant enzyme in active form has also been accomplished (Chen W. -J., et al., J. Biol. Chem., 268:9675 (1993)).

In light of the foregoing, the discovery that the function of oncogenic ras proteins is critically dependent on their post-translational processing provides a means of cancer chemotherapy through inhibition of the processing enzymes. The identification and isolation of a protein farnesyltransferase that catalyzes the addition of a farnesyl group to ras proteins provides a promising target for such intervention. Recently, it has been determined that prototypical inhibitors of PPT can inhibit ras processing and reverse cancerous morphology in tumor cell models (Kohl N. E., et al., Science, 260:1934 (1993), James G. L., et al., Science, 260:1937 (1993), Garcia A. M., et al., J. Biol. Chem., 268:18415 (1993)). Furthermore, Blaskovich M., et al., "Proceedings Eighty-Sixth Annual Meeting American Association For Cancer Research," Mar. 18–22, 1995, Toronto, Ontario, Canada, Vol. 86, March 1995, Abstract 2578, disclosed a series of tetrapeptide inhibitors of farnesyltransferase which inhibited growth of tumor cells in nude mice.

Nagasu T., et al., "Proceedings Eighty-Sixth Annual Meeting American Association For Cancer Research," Mar. 18–22, 1995, Toronto, Ontario, Canada, Vol. 86, March 1995, Abstract 2615, disclosed a peptidomimetic inhibitor, B956, of farnesyltransferase which inhibits growth of human tumor xenografts in nude mice. Kohl, N. E., et al., Proc. Natl. Acad. Sci. USA, 91:9141 (1994) have demonstrated that the protein farnesyltransferase inhibitor (L-739, 749) blocks the growth of a ras-dependent tumor in nude mice. Sebti, S. M., et al., Cancer Research, 55:4243 (1995) have demonstrated that a farnesyltransferase inhibitor (FTI-276) blocks the growth in nude mice of a human lung carcinoma with a k-ras mutation. Inhibition of tumor growth is correlated with inhibition of ras processing.

Thus, it is possible to prevent or delay the onset of cellular proliferation in cancers that exhibit mutant ras proteins by blocking PFT. By analogous logic, inhibition of PFT would provide a potential means for controlling cellular proliferation associated with restenosis, especially in those cases wherein the expression and/or function of native ras is overstimulated. Indolfi, C., et al., *Nature Medicine*, 1:541 (1995) have demonstrated that inhibition of cellular ras prevents smooth muscle cell proliferation after vascular injury in the rat.

PCT Published Patent Application WO91/16340 discloses cysteine containing tetrapeptide inhibitors of PFT of the Formula CAAX.

European Published Patent Application 0461869 discloses cysteine containing tetrapeptide inhibitors of PFT of the Formula Cys-Aaa$^1$-Aaa$^2$-Xaa.

European Published Patent Application 0520823 discloses cysteine containing tetrapeptide inhibitors of PFT of the Formula Cys-Xaa$^1$-dXaa$^2$-Xaa$^3$.

European Published Patent Application 0523873 discloses cysteine containing tetrapeptide inhibitors of PFT of the Formula Cys-Xaa$^1$-Xaa$^2$-Xaa$^3$.

European Published Patent Application 0528486 discloses cysteine containing tetrapeptide amides inhibitors of PFT of the Formula Cys-Xaa$^1$-Xaa$^2$-Xaa$^3$-NRR$^1$.

European Published Patent Application 0535730 discloses pseudotetrapeptide inhibitors of PFT of the following two formulas:

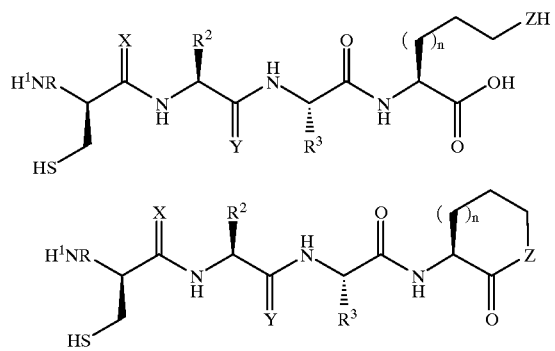

Copending U.S. patent application Ser. No. 08/268,364 discloses a series of histidine and homohistidine derivatives as inhibitors of protein farnesyltransferase.

U.S. Pat. No. 4,870,183 discloses a series of amino acid derivatives of the Formula I:

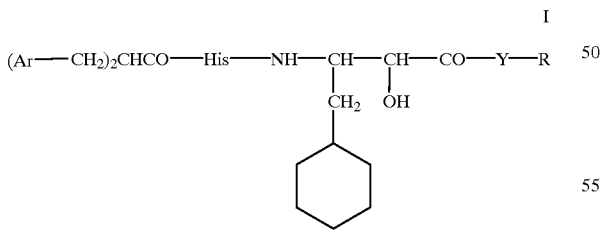

wherein Ar represents a phenyl group, a naphthyl group, or pyridyl group which may have a substituent. His represents an L-histidyl group, Y represents —O— or —NH—, R represents a straight or branched chain alkyl group, a cycloalkyl group or a halogenated alkyl group, or pharmaceutically acceptable acid addition salts thereof, useful for treatment of hypertension, especially renin-associated hypertension. Additionally, U.S. Pat. No. 4,870,183 discloses intermediates of Formula IV:

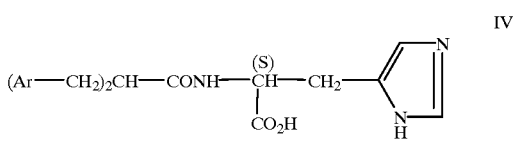

wherein the carbon atom marked with (S) is of S— configuration and Ar is as defined above which are used to prepare compounds of Formula I.

U.S. Pat. No. 4,904,660 discloses a series of histidine derivatives useful as renin inhibitors in the treatment of hypertension. Additionally, U.S. Pat. No. 4,904,660 discloses intermediates of formula

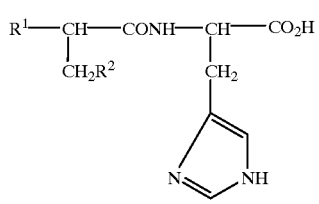

wherein R$_1$ is

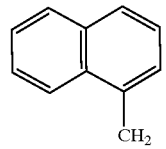

and

R$_2$ is

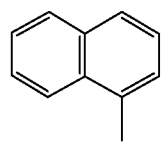

which are used to prepare the target renin inhibitors.

Compounds disclosed in the above references do not disclose or suggest the novel combination of structural variations found in the present invention described hereinafter.

We have surprisingly and unexpectedly found that a series of substituted histidines are inhibitors of farnesyltransferase and thus useful as agents for the treatment of proliferative diseases such as, for example, cancer, restenosis, and psoriasis, and as antiviral agents.

SUMMARY OF THE INVENTION

A compound of Formula I

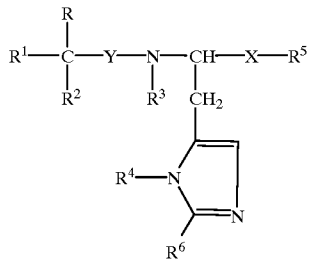

I wherein R is hydrogen or alkyl; $R^1$ and $R^2$ may be the same or different and are selected from the group consisting of:

a)

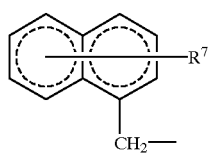

wherein the bicyclic ring may be aromatic, or partially or completely saturated, and $R^7$ may be 1 to 3 substituents selected from the group consisting of:

hydrogen,
alkyl,
alkenyl,
alkoxy,
thioalkoxy,
hydroxy,
mercapto,
halogen,
nitro,

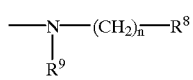

wherein $R^8$ and $R^9$ may be the same or different and are selected from the group consisting of:
hydrogen,
alkyl, or $R^8$ and $R^9$ are taken together with N to form a 5- or 6-membered ring optionally containing a heteroatom selected from the group consisting of: S, O, and N—$R^{10}$ wherein $R^{10}$ is hydrogen or alkyl, and
n is zero or an integer of one to four,

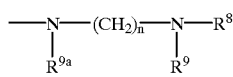

wherein $R^{9a}$ is hydrogen or alkyl and $R^8$, $R^9$, and n are as defined above, and

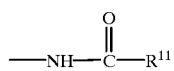

wherein $R^{11}$ is selected from the group consisting of:
hydrogen,
alkyl, and
aryl, b)

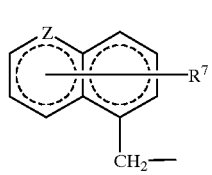

wherein the bicyclic ring may be aromatic, or partially or completely saturated, and Z is selected from the group consisting of:

$NR^{12}$ wherein $R^{12}$ is hydrogen, alkyl, or

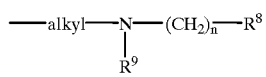

wherein $R^8$, $R^9$, and n are as defined above, or $R^{12}$ is absent,
O,
S,
SO, and
$SO_2$, and
Z may be at other positions in the bicyclic ring system provided that when the bicyclic ring is aromatic, Z is not at the point of attachment of the $CH_2$ unit, and $R^{12}$ is absent, and $R^7$ is as defined above, c)

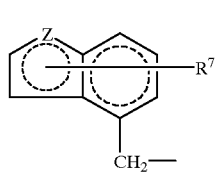

wherein the bicyclic ring may be aromatic, or partially or completely saturated, and Z and $R^7$ are as defined above, and $R^{12}$ may be present, d)

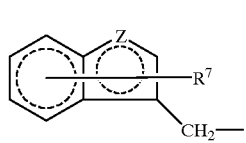

wherein the bicyclic ring may be aromatic, or partially or completely saturated, and Z and $R^7$ are as defined above, and $R^{12}$ may be present, e)

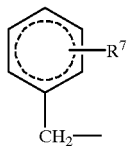

wherein the monocyclic ring may be aromatic, or partially or completely saturated, and $R^7$ is as defined above with the proviso that $R^1$ and $R^2$ are not both a monocyclic ring, and f)

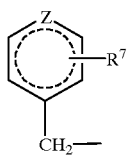

wherein the monocyclic ring may be aromatic, or partially or completely saturated, and $R^7$ and Z are as defined above with the proviso that $R^1$ and $R^2$ are not both a monocyclic ring;

$R^3$ is hydrogen or alkyl;

$R^4$ is selected from the group consisting of:
hydrogen,
alkyl,
alkenyl,
alkynyl,
benzyl,
alkyl chain wherein the alkyl chain may be interrupted by a heteroatom selected from the group consisting of: S, O, and N—$R^{10}$ wherein $R^{10}$ is as defined above,

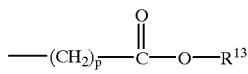

wherein p is an integer of one to four, and $R^{13}$ is alkyl or benzyl, and

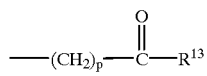

wherein p and $R^{13}$ are as defined above;

X is

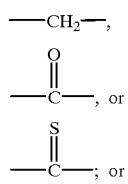

Y is

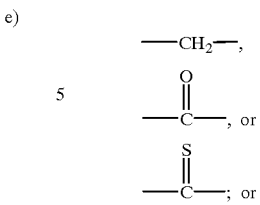

$R^5$ is selected from the group consisting of:
—$OR^{14}$ wherein $R^{14}$ is selected from the group consisting of:
hydrogen,
alkyl,
alkenyl,
alkynyl,
cycloalkyl,
cycloalkylalkyl,
haloalkyl,
hydroxyalkyl,
mercaptoalkyl,
cyanoalkyl,
nitroalkyl,
alkoxyalkyl,
arylalkyl,
heteroarylalkyl,
benzyloxyalkyl,
thioalkoxyalkyl,
acetamidoalkyl,
$HOCH_2CH_2$—S—S—$CH_2CH_2$—,

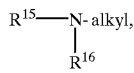

wherein $R^{15}$ and $R^{16}$ may be the same or different and are selected from the group consisting of:
hydrogen,
alkyl or $R^{15}$ and $R^{16}$ are taken together with N to form a 5- or 6-membered ring optionally containing a heteroatom selected from the group consisting of: S, O, and N—$R^{10}$ wherein $R^{10}$ is as defined above,
$HO_2C$-alkyl,
alkyl-$O_2C$-alkyl, and

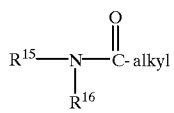

wherein $R^{15}$ and $R^{16}$ are as defined above,
—S—$R^{14}$ wherein $R^{14}$ is as defined above with the proviso that $R^{14}$ is not hydrogen,

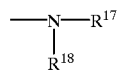

wherein $R^{17}$ and $R^{18}$ may be the same or different and are selected from the group consisting of:
hydrogen,
alkyl,
alkenyl, alkynyl,
cyanoalkyl,
hydroxyalkyl,
alkoxyalkyl,
arylalkyl,
heteroarylalkyl,
benzyloxyalkyl,
cycloalkyl,
cycloalkylalkyl,
haloalkyl,
mercaptoalkyl,
nitroalkyl,
thioalkoxyalkyl,
acetamidoalkyl,

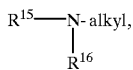

wherein $R^{15}$ and $R^{16}$ may be the same or different and are selected from the group consisting of:
hydrogen,
alkyl or $R^{15}$ and $R^{16}$ are taken together with N to form a 5- or 6-membered ring optionally containing a heteroatom selected from the group consisting of: S, O, and N—$R^{10}$ wherein $R^{10}$ is as defined above,
or $R^{17}$ and $R^{18}$ are taken together with N to form a 5- or 6-membered ring optionally containing a heteroatom selected from the group consisting of: S, O, and N—$R^{10}$ wherein $R^{10}$ is as defined above,
—NH—$OR^{10}$ wherein $R^{10}$ is as defined above,
alkyl,
alkenyl, and
arylalkyl; and
$R^6$ is hydrogen,
—SR where R is as defined above,
—OR where R is as defined above, or

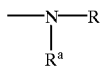

wherein R and $R^a$ may be the same or different and are as defined above for R;
and when X is —$CH_2$— and $R^{17}$ is hydrogen or alkyl then
$R^{18}$ may be

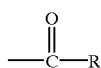

wherein R is as defined above, or

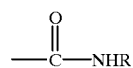

wherein R is as defined above; and when

X is

must be

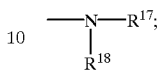

and
excluding the compound wherein
R is hydrogen,
$R^1$ and $R^2$ are each

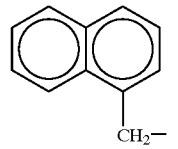

$R^3$ is hydrogen,
$R^4$ is hydrogen,

X is 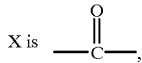

Y is 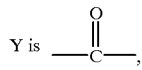

$R^5$ is $OR^{14}$ wherein $R^{14}$ is hydrogen, and
$R^6$ is hydrogen;
and corresponding isomers thereof;
or a pharmaceutically acceptable salt thereof.

As inhibitors of farnesyltransferase, the compounds of Formula I are antiproliferative agents. Thus, they are useful for the treatment of cancer, restenosis, and psoriasis, and as antiviral agents. Additionally, a compound of Formula I may be combined with other conventional anti-cancer agents such as, for example, cisplatin.

A still further embodiment of the present invention is a pharmaceutical composition for administering an effective amount of a compound of Formula I in unit dosage form in the treatment methods mentioned above. Finally, the present invention is directed to methods for production of a compound of Formula I.

DETAILED DESCRIPTION OF THE INVENTION

In the compounds of Formula I, the term "alkyl" means a straight or branched hydrocarbon radical having from 1 to 12 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl, undecyl, dodecyl, and the like.

The term "alkenyl" means a straight or branched unsaturated hydrocarbon radical having from 2 to 12 carbon atoms and includes, for example, ethenyl, 2-propenyl, 1-butenyl, 2-butenyl, 1-pentenyl, 2-pentenyl, 3-methyl-3-butenyl, 1-hexenyl, 2-hexenyl, 3-hexenyl, 3-heptenyl, 1-octenyl, 1-nonenyl, 1-decenyl, 1-undecenyl, 1-dodecenyl, and the like.

The term "alkynyl" means a straight or branched triple bonded unsaturated hydrocarbon radical having from 2 to 12 carbon atoms and includes, for example, ethynyl, 2-propynyl, 3-butynyl, 4-pentynyl, 5-hexynyl, 6-heptynyl, 7-octynyl, 8-nonynyl, 9-decynyl, 10-undecynyl, 11-dodecynyl, and the like.

The term "cycloalkyl" means a saturated hydrocarbon ring which contains from 3 to 12 carbon atoms, for example, cyclopropyl, cyclobutyl, cyclopentyl, cyclohexyl, adamantyl, and the like.

The term "cycloalkylalkyl" means a saturated hydrocarbon ring attached to an alkyl group wherein alkyl is as defined above. The saturated hydrocarbon ring contains from 3 to 12 carbon atoms. Examples of such are cyclopropylmethyl, cyclopentylmethyl, cyclohexylmethyl, adamantylmethyl and the like.

The terms "alkoxy" and "thioalkoxy" are O-alkyl or S-alkyl as defined above for alkyl.

The term "aryl" means an aromatic radical which is a phenyl group, a naphthyl group, a phenyl group substituted by 1 to 4 substituents selected from alkyl as defined above, alkoxy as defined above, thioalkoxy as defined above, hydroxy, halogen, trifluoromethyl, amino, alkylamino as defined above for alkyl, dialkylamino as defined for alkyl, N-acetylamino, cyano —SO$_2$NH$_2$, or nitro, or a naphthyl group substituted by 1 to 4 substituents as defined above for a phenyl group substituted by 1 to 4 substituents.

The term "heteroaryl" means a heteroaromatic radical which is 2- or 3-thienyl; 2- or 3-furanyl; 1-, 2- or 3-pyrrolyl; 1-, 2-, 4-, or 5-imidazolyl; 1-, 3-, 4-, or 5-pyrazolyl; 2-, 4-, or 5-thiazolyl; 3-, 4-, or 5-isothiazolyl; 2-, 4-, or 5-oxazolyl; 3-, 4-, or 5-isoxazolyl; 1-, 3-, or 5-1,2,4-triazolyl; 1-, 2-, 4-, or 5-1,2,3-triazolyl; 1- or 5-tetrazolyl; 4-, or 5-1,2,3-oxadiazolyl; 3-, or 5-1,2,4-oxadiazolyl; 2-1,3,4-oxadiazolyl; 2-1,3,4-thiadiazoyl; 2-1,3,5-triazinyl; 3-pyridinyl; 3-, 4-, or 5-pyridazinyl; 2-pyrazinyl; 2-, 4-, or 5-pyrimidinyl; unsubstituted or substituted by 1 to 2 substituents selected from NH$_2$, OH, S, halogen as defined hereinafter, alkyl as defined above, or alkoxy as defined above.

The term "arylalkyl" means an aromatic radical attached to an alkyl radical wherein aryl and alkyl are as defined above, for example, benzyl, naphthylmethyl, 4-sulfamoylphenylmethyl and the like.

The term "heteroarylalkyl" means a heteroaromatic radical attached to an alkyl radical wherein heteroaryl and alkyl are as defined above, for example, 2-imidazol-1-yl-ethyl, 3-imidazol-1-yl-propyl, 2-(1H-imidazol-4-yl)-ethyl, 2-butyl-1H-imidazol-4-ylmethyl, 2-thiophen-2-yl-ethyl, thiophen-3-ylmethyl, and the like.

"Halogen" is fluorine, chlorine, bromine, or iodine.

The term "haloalkyl" means a halogen atom attached to an alkyl radical wherein halogen and alkyl are as defined above.

The term "hydroxyalkyl" means a hydroxy group attached to an alkyl radical wherein alkyl is as defined above.

The term "mercaptoalkyl" means a mercapto group attached to an alkyl radical wherein alkyl is as defined above.

The term "cyanoalkyl" means a cyano group attached to an alkyl radical wherein alkyl is as defined above.

The term "nitroalkyl" means a nitro group attached to an alkyl radical wherein alkyl is as defined above.

The term "alkoxyalkyl" means an alkoxy group attached to an alkyl radical wherein alkoxy and alkyl are as defined above.

The term "thioalkoxyalkyl" means a thioalkoxy group attached to an alkyl radical wherein thioalkoxy and alkyl are as defined above.

The term "acetamidoalkyl" means a

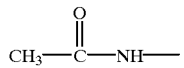

group attached to an alkyl radical wherein alkyl is as defined above.

The term "benzyloxyalkyl" means a benzyloxy group attached to an alkyl radical wherein alkyl is as defined above.

The ring designated:

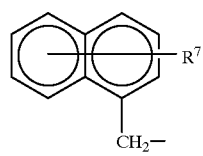

represents a bicyclic ring that may be either aromatic, or partially or completely saturated, for example:

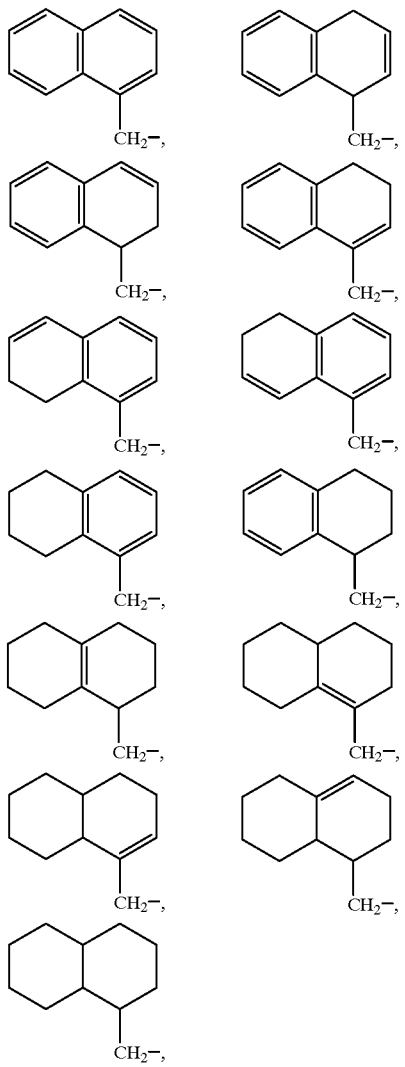

and the like mono- to trisubstituted by $R^7$ which may be attached at any carbon atom of the bicyclic ring excluding unsaturated bridgehead carbon atoms and unsaturated carbon atoms wherein the —$CH_2$— group is attached, and $R^7$ is selected from hydrogen, alkyl, alkenyl, alkoxy, thioalkoxy, hydroxy, mercapto, halogen, nitro,

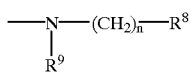

wherein $R^8$ and $R^9$ may be the same or different and are selected from the group consisting of:

hydrogen, alkyl, or $R^8$ and $R^9$ are taken together with N to form a 5- or 6-membered ring optionally containing a heteroatom selected from the group consisting of: S, O, and N—$R^{10}$ wherein $R^{10}$ is hydrogen or alkyl, n is zero or an integer of one to four,

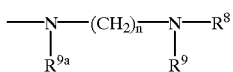

wherein $R^{9a}$ is hydrogen or alkyl and $R^8$, $R^9$, and n are as defined above, and

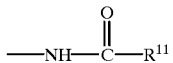

wherein $R^{11}$ is selected from the group consisting of hydrogen, alkyl, and aryl wherein alkyl, alkenyl, alkoxy, thioalkoxy, halogen, aryl, and $R^7$ are as defined above.

The ring designated:

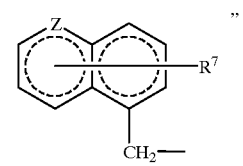

represents a bicyclic ring that may be either aromatic, or partially or completely saturated, wherein Z is selected from the group consisting of: $NR^{12}$ wherein $R^{12}$ is hydrogen or alkyl or

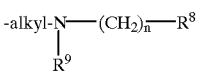

wherein $R^8$, $R^9$, and n are as defined above, or $R^{12}$ is absent, O, S, SO, and $SO_2$ and Z may be at other positions in the bicyclic ring system provided that when the bicyclic ring system is aromatic, Z is not at the point of attachment of the $CH_2$— unit, and $R^{12}$ is absent, for example:

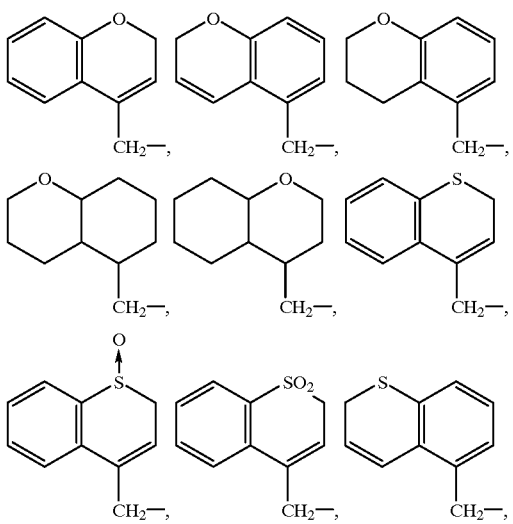

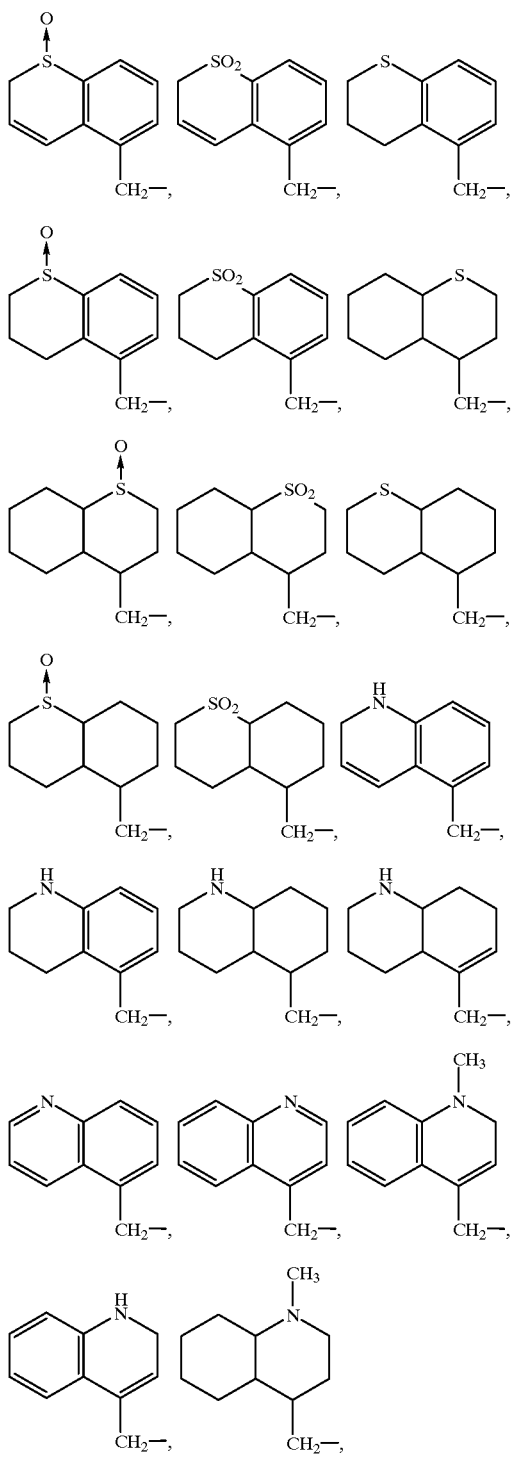

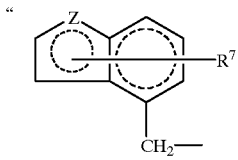

The ring designated:

represents a bicyclic ring that may be either aromatic, or partially or completely saturated, for example:

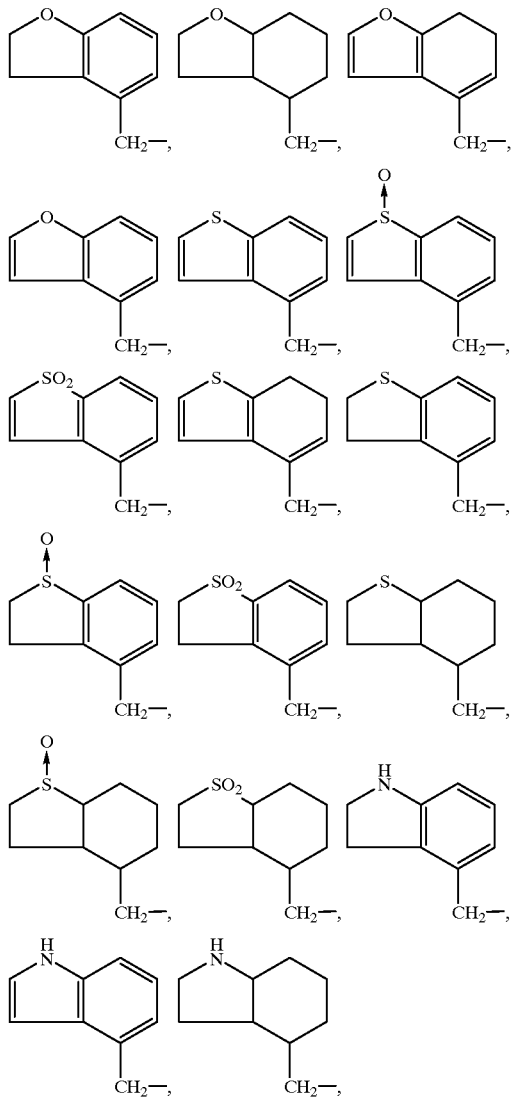

and the like mono- to trisubstituted by $R^7$ as defined above wherein $R^7$ may be attached at any carbon atom of the bicyclic ring excluding unsaturated bridgehead carbon atoms and unsaturated carbon atoms wherein the —$CH_2$— group is attached.

and the like mono- and trisubstituted by $R^7$ as defined above wherein $R^7$ may be attached at any carbon atom of the bicyclic ring excluding unsaturated bridgehead carbon atoms, and unsaturated carbon atoms wherein the —$CH_2$— group is attached, and Z is as defined above and $R^{12}$ may be present.

The ring designated:

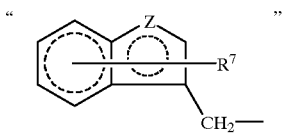

represents a bicyclic ring that may be either aromatic, or partially or completely saturated, for example:

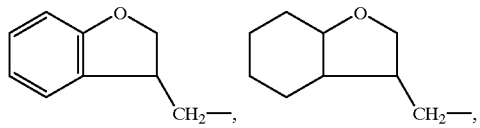

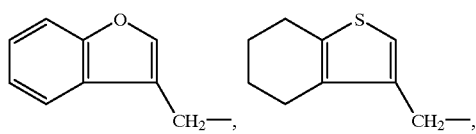

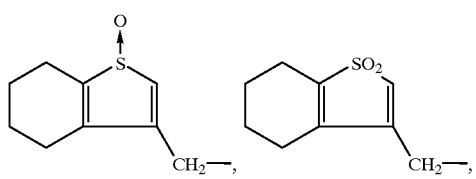

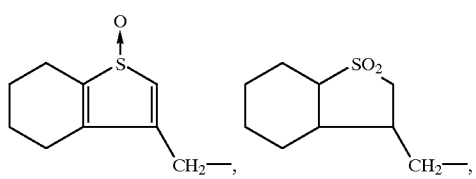

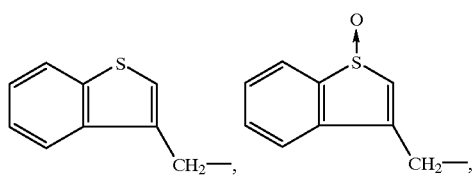

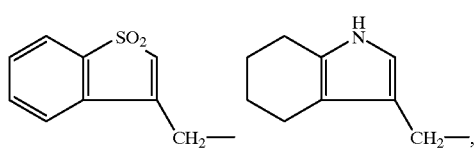

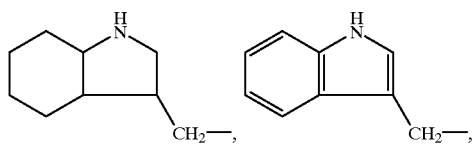

and the like mono- and trisubstituted by $R^7$ as defined above wherein $R^7$ may be attached at any carbon atom of the bicyclic ring excluding unsaturated bridgehead carbon atoms, and unsaturated carbon atoms wherein the —CH$_2$— is attached, and Z is as defined above and $R^{12}$ may be present.

The ring designated:

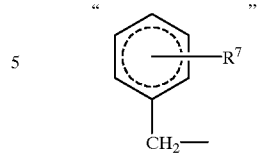

wherein the monocyclic ring may be aromatic, or partially or completely saturated, for example:

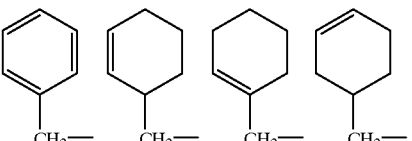

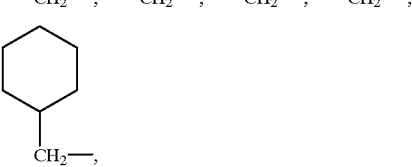

and the like mono- to trisubstituted by $R^7$ as defined above wherein $R^7$ may be attached at any carbon atom of the monocyclic ring excluding unsaturated carbon atoms wherein the —CH$_2$— group is attached.

The ring designated:

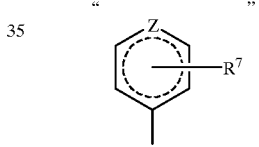

wherein the monocyclic ring may be aromatic, or partially or completely saturated, for example:

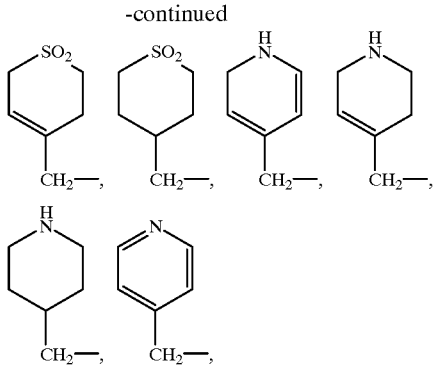

and the like mono- to trisubstituted by $R^7$ as defined above wherein $R^7$ may be attached at any carbon atom of the monocyclic ring excluding unsaturated carbon atoms wherein the —$CH_2$— group is attached.

The compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *J. of Pharma. Sci.*, 66:1 (1977)).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S. M., et al., "Pharmaceutical Salts," *J. of Pharma. Sci.*, 66:1 (1977)).

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

A preferred compound of Formula I is one wherein

R is hydrogen;

$R^7$ is selected from the group consisting of:
hydrogen,
methoxy,
thiomethoxy,
hydroxy,
halogen, and $$—\underset{R^9}{\overset{}{N}}—R^8$$

wherein $R^8$ and $R^9$ may be the same or different and are selected from the group consisting of:
hydrogen, and
alkyl;

$R^3$ is hydrogen or methyl;

$R^4$ is selected from the group consisting of:
hydrogen,
methyl,
ethyl, and
—$CH_2$—O—$CH_3$;

X is

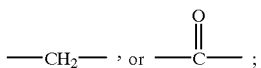

or

Y is

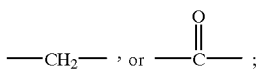

or $R^5$ is selected from the group consisting of:
—O—$R^{14}$ wherein $R^{14}$ is selected from the group consisting of:
hydrogen,
alkyl,
alkenyl,
alkynyl,
cycloalkyl,
cycloalkylalkyl, hydroxyalkyl,
mercaptoalkyl,
cyanoalkyl,
alkoxyalkyl,
arylalkyl,
heteroarylalkyl,
benzyloxyalkyl,
thioalkoxyalkyl,
acetamidoalkyl,
HOCH$_2$CH$_2$—S—S—CH$_2$CH$_2$—,

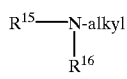

wherein R$^{15}$ and R$^{16}$ may be the same or different and are selected from the group consisting of:
hydrogen,
alkyl or R$^{15}$ and R$^{16}$ are taken together with N to form a 5- or 6-membered ring optionally containing a heteroatom selected from the group consisting of: O, and NR$^{10}$ wherein R$^{10}$ is hydrogen or methyl, and
alkyl-O$_2$C-alkyl,
—S—R$^{14}$ wherein R$^{14}$ is as defined above with the proviso that R$^{14}$ is not hydrogen, and

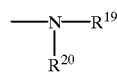

wherein R$^{19}$ is
hydrogen,
alkyl,
alkenyl,
alkynyl,
cycloalkyl,
cycloalkylalkyl,
cyanoalkyl,
hydroxyalkyl,
alkoxyalkyl,
arylalkyl,
heteroarylalkyl,
benzyloxyalkyl,
mercaptoalkyl,
thioalkoxyalkyl,
acetamidoalkyl,

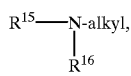

wherein R$^{15}$ and R$^{16}$ may be the same or different and are selected from the group consisting of:
hydrogen,
alkyl or R$^{15}$ and R$^{16}$ are taken together with N to form a 5- or 6-membered ring optionally containing a heteroatom selected from the group consisting of: S, O, and N—R$^{10}$ wherein R$^{10}$ is as defined above, and
R$^{20}$ is hydrogen or methyl; and
R$^6$ is hydrogen.

A more preferred compound of Formula I is one wherein R$^1$ and R$^2$ may be the same or different and are selected from the group consisting of:

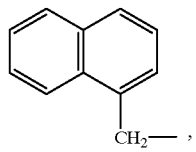

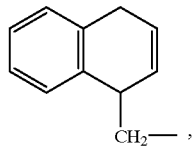

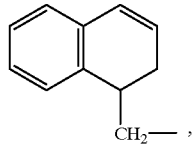

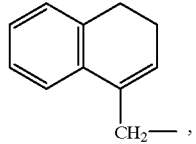

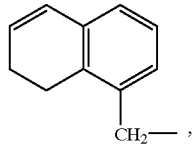

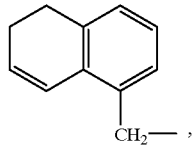

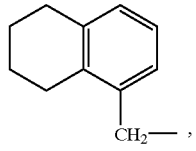

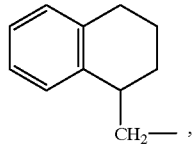

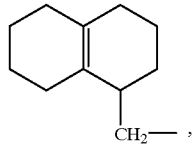

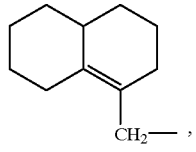

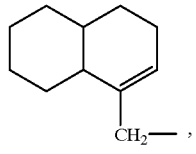

-continued
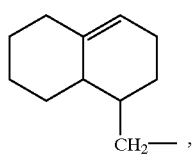
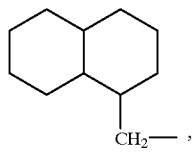
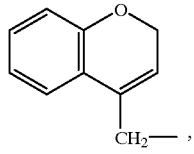
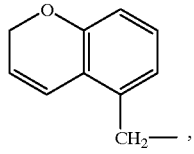
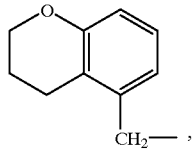
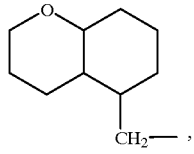
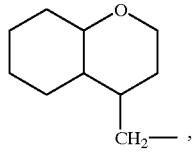
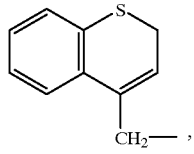
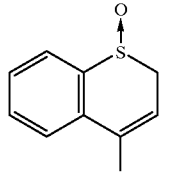
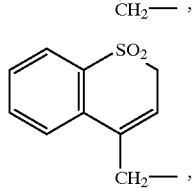
-continued
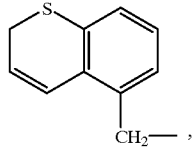
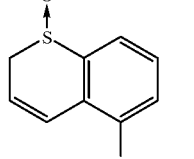
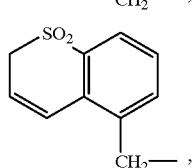
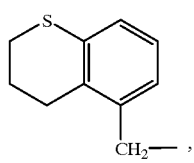
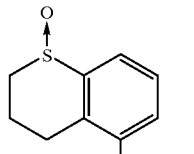
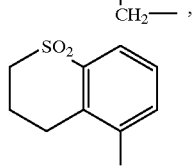
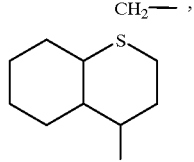
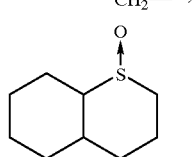
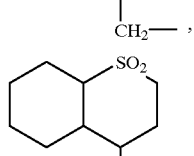
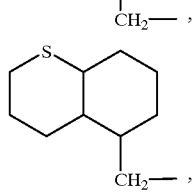

-continued
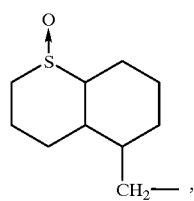
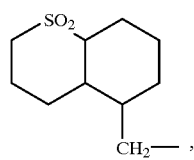
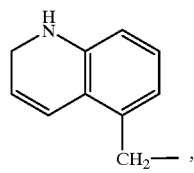
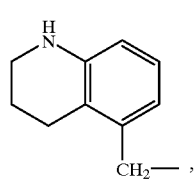
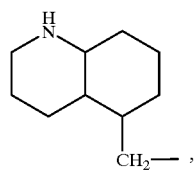
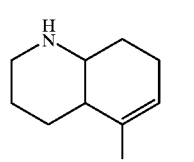
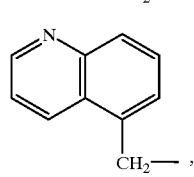
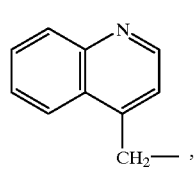
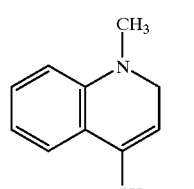
-continued
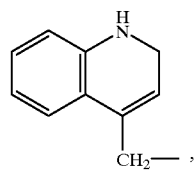
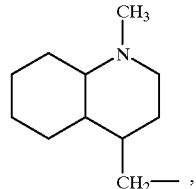
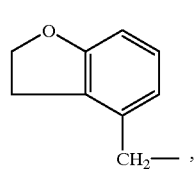
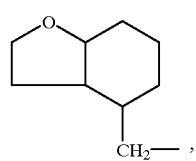
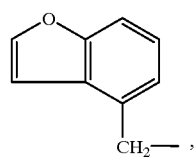
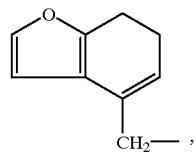
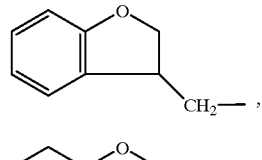
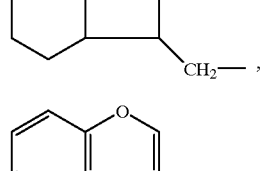
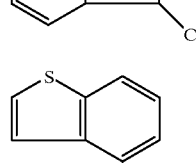

-continued
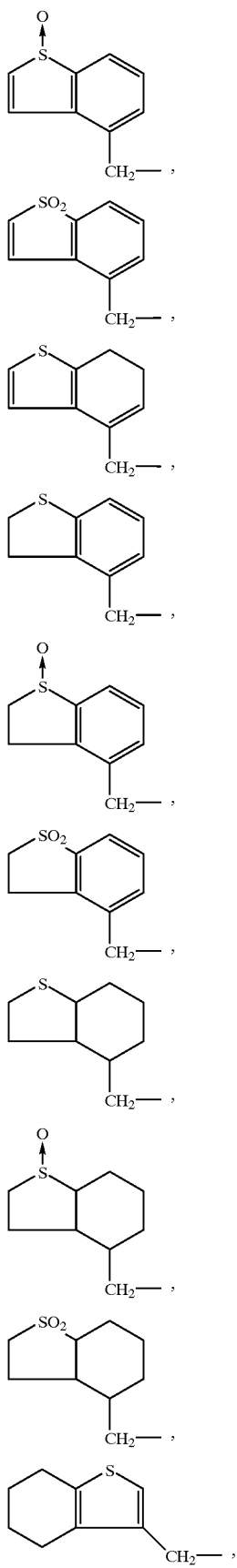
-continued
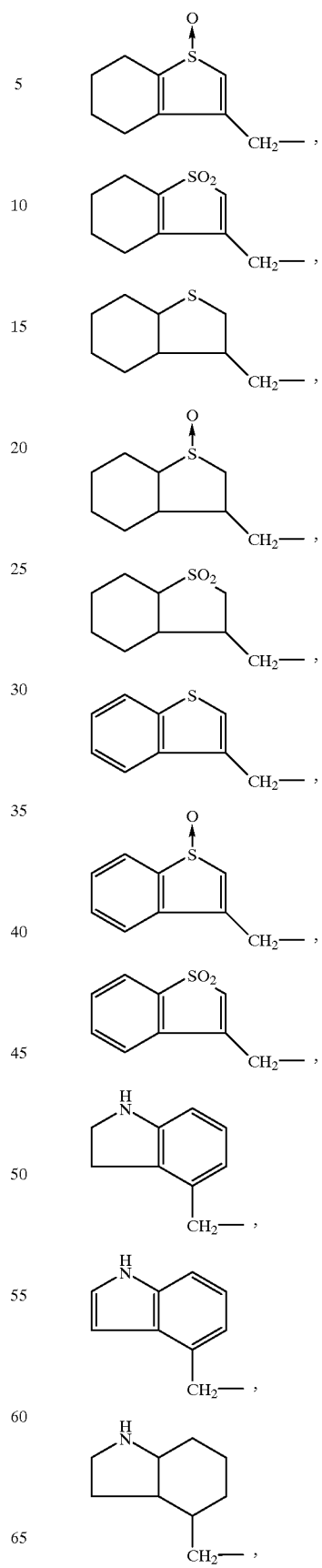

-continued

[structure: 4,5,6,7-tetrahydroindol-3-ylmethyl]  —CH₂—,

[structure: octahydroindol-3-ylmethyl]  —CH₂—,

[structure: indol-3-ylmethyl]  —CH₂—, and

[structure: benzyl]  —CH₂— ;

R³ is hydrogen or methyl;
R⁴ is hydrogen, methyl, or —CH₂OCH₃;
X is —CH₂— or $$-\overset{O}{\underset{}{\overset{\|}{C}}}- ;$$

Y is —CH₂—, or $$-\overset{O}{\underset{}{\overset{\|}{C}}}- ;$$

and
R⁵ is selected from the group consisting of:
—O—R¹⁴ wherein R¹⁴ is selected from the group consisting of:
hydrogen,
alkyl,
alkenyl,
alkynyl,

—CH₂—CH₂—N(CH₃)—CH₃,

—CH₂—CH₂—N(C₂H₅)—C₂H₅,

—CH₂—[phenyl],

—CH₂—CH₂—[phenyl],

—CH₂—CH₂—[phenyl]—SO₂NH₂,

—CH₂—[methylcyclohexyl],

—CH₂—[cyclohexyl],

—CH₂—[cyclopropyl],

—CH₂—CH₂—N[morpholine]O,

—CH₂—CH₂—N[piperazine]NH,

—CH₂—CH₂—N[piperazine]N—CH₃,

—CH₂—CH₂—[imidazol-4-yl]H,

—CH₂—CH₂—N[imidazol-1-yl],

—CH₂—CH₂—CH₂—N[imidazol-1-yl],

—CH₂—[2-butylimidazol-4-yl]—C₄H₉,

—CH₂—CN,

—CH(CH₃)—CN,

—CH₂—CH₂—CN,

—CH₂—CH₂—CH₂—CN,

—CH₂—CH₂—OH,

—CH₂—CH₂—CH₂—OH,

—CH₂—CH₂—SH,

—CH₂—CH₂—S—C₂H₅,

—CH₂—CH₂—S—S—CH₂CH₂OH,

—CH₂—CH₂—O—CH₂—[phenyl],

—CH₂—CH₂—[2-pyridyl],

—CH₂—CH₂—[3-pyridyl],

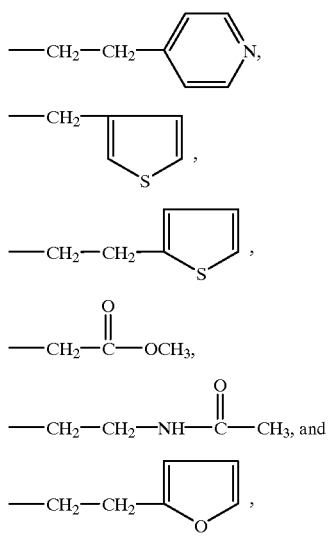
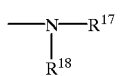
—SR$^{14}$ wherein R$^{14}$ is as defined above with the proviso that R$^{14}$ is not hydrogen, and
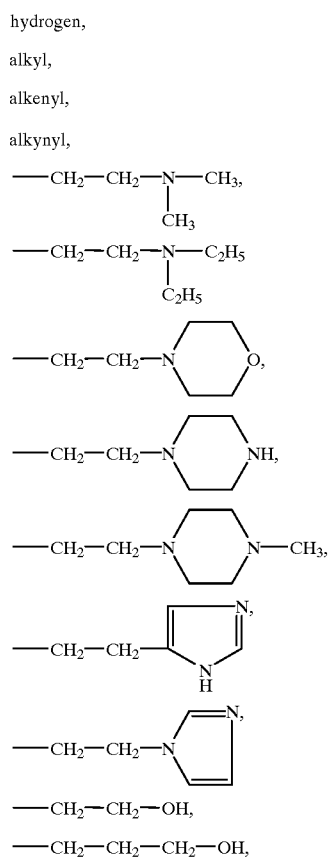
wherein R$^{17}$ is selected from the group consisting of:
hydrogen,
alkyl,
alkenyl,
alkynyl,
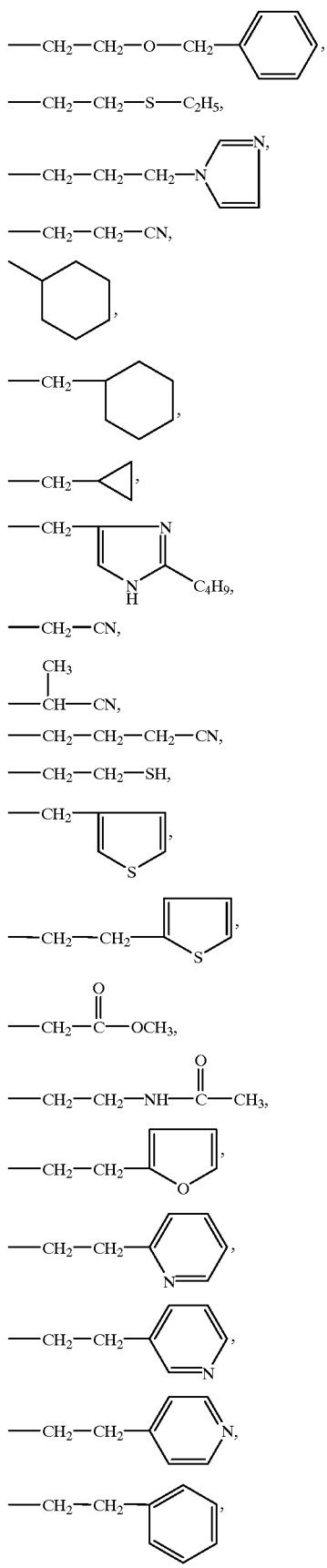

-continued

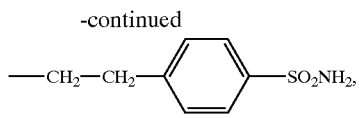

$R^{18}$ is hydrogen or methyl, and —NH—$OR^{10}$ wherein $R^{10}$ is hydrogen or methyl.

Particularly valuable is a compound selected from the group consisting of:

(S)-3-(1H-Imidazol-4-yl)-2-(3-naphthalen-1-yl-2-naphthalen-1-ylmethyl-propionylamino)-propionic acid, methyl ester;

(R)-3-(1H-Imidazol-4-yl)-2-(3-naphthalen-1-yl-2-naphthalen-1-ylmethyl-propionylamino)-propionic acid, methyl ester;

(S)-3-(1H-Imidazol-4-yl)-2-(3-naphthalen-1-yl-2-naphthalen-1-ylmethyl-propionylamino)-propionic acid;

(R)-3-(1H-Imidazol-4-yl)-2-(3-naphthalen-1-yl-2-naphthalen-1-ylmethyl-propionylamino)-propionic acid;

(S)-3-(1H-Imidazol-4-yl)-2-(3-naphthalen-1-yl-2-naphthalen-1-ylmethyl-propionylamino)-propionic acid, ethyl ester;

(S)-3-(3-Methyl-3H-imidazol-4-yl)-2-(3-naphthalen-1-yl-2-naphthalen-1-ylmethyl-propionylamino)-propionic acid, methyl ester;

(S)-3-(1H-Imidazol-4-yl)-2-(3-naphthalen-1-yl-2-naphthalen-1-ylmethyl-propionylamino)-propionic acid, propyl ester;

(S)-3-(1H-Imidazol-4-yl)-2-(3-naphthalen-1-yl-2-naphthalen-1-ylmethyl-propionylamino)-propionic acid, isopropyl ester;

(S)-3-(1H-Imidazol-4-yl)-2-(3-naphthalen-1-yl-2-naphthalen-1-ylmethyl-propionylamino)-propionic acid, butyl ester;

(S)-3-(1H-Imidazol-4-yl)-2-(3-naphthalen-1-yl-2-naphthalen-1-ylmethyl-propionylamino)-propionic acid, benzyl ester;

(S)-3-(1H-Imidazol-4-yl)-2-(3-naphthalen-1-yl-2-naphthalen-1-ylmethyl-propionylamino)-propionic acid, cyclohexyl ester;

(S)-3-(1H-Imidazol-4-yl)-2-(3-naphthalen-1-yl-2-naphthalen-1-ylmethyl-propionylamino)-propionic acid, cyclopropylmethyl ester;

(S)-3-(1H-Imidazol-4-yl)-2-(3-naphthalen-1-yl-2-naphthalen-1-ylmethyl-propionylamino)-propionic acid, 2-butyl-1H-imidazol-4-ylmethyl ester;

(S)-3-(1H-Imidazol-4-yl)-2-(3-naphthalen-1-yl-2-naphthalen-1-ylmethyl-propionylamino)-propionic acid, (±)-sec-butyl ester;

(S)-3-(1H-Imidazol-4-yl)-2-(3-naphthalen-1-yl-2-naphthalen-1-ylmethyl-propionylamino)-propionic acid, allyl ester;

(S)-3-(1H-Imidazol-4-yl)-2-(3-naphthalen-1-yl-2-naphthalen-1-ylmethyl-propionylamino)-propionic acid, prop-2-ynyl ester;

(S)-3-(1H-Imidazol-4-yl)-2-(3-naphthalen-1-yl-2-naphthalen-1-ylmethyl-propionylamino)-propionic acid, 2-cyano-ethyl ester;

(S)-3-(1H-Imidazol-4-yl)-2-(3-naphthalen-1-yl-2-naphthalen-1-ylmethyl-propionylamino)-propionic acid, 2-benzyloxy-ethyl ester;

(S)-3-(1H-Imidazol-4-yl)-2-(3-naphthalen-1-yl-2-naphthalen-1-ylmethyl-propionylamino)-propionic acid, 2-thiophen-2-yl-ethyl ester;

(S)-3-(1H-Imidazol-4-yl)-2-(3-naphthalen-1-yl-2-naphthalen-1-ylmethyl-propionylamino)-propionic acid, thiophen-3-ylmethyl ester;

(S)-3-(1H-Imidazol-4-yl)-2-(3-naphthalen-1-yl-2-naphthalen-1-ylmethyl-propionylamino)-propionic acid, 2-diethylamino-ethyl ester;

(S)-3-(1H-Imidazol-4-yl)-2-(3-naphthalen-1-yl-2-naphthalen-1-ylmethyl-propionylamino)-propionic acid, 2-morpholin-4-yl-ethyl ester;

(S)-N-[1-(2-Benzyloxy-ethylcarbamoyl)-2-(1H-imidazol-4-yl)-ethyl]-3-naphthalen-1-yl-2-naphthalen-1-ylmethyl-propionamide;

(S)-N-[1-(Carbamoyl-2-(1H-imidazol-4-yl)-ethyl]-3-naphthalen-1-yl-2-naphthalen-1-ylmethyl-propionamide;

(S)-N-[2-(1H-Imidazol-4-yl)-1-(2-iraidazol-1-yl-ethylcarbamoyl)-ethyl]-3-naphthalen-1-yl-2-naphthalen-1-ylmethyl-propionamide;

(S)-N-[1-(2-Ethylsulfanyl-ethylcarbamoyl)-2-(1H-imidazol-4-yl)-ethyl]-3-naphthalen-1-yl-2-naphthalen-1-ylmethyl-propionamide;

(S)-N-[2-(1H-Imidazol-4-yl)-1-[2-(1H-imidazol-4-yl)-ethylcarbamoyl]-ethyl]-3-naphthalen-1-yl-2-naphthalen-1-ylmethyl-propionamide;

(S)-N-[2-(1H-Imidazol-4-yl)-1-(3-imidazol-1-yl)-propylcarbamoyl)-ethyl]-3-naphthalen-1-yl-2-naphthalen-1-ylmethyl-propionamide;

(S)-N-[1-(2-Hydroxy-ethylcarbamoyl)-2-(1H-imidazol-4-yl)-ethyl]-3-naphthalen-1-yl-2-naphthalen-1-ylmethyl-propionamide;

(S)-N-[2-(1H-Imidazol-4-yl)-1-isopropylcarbamoyl-ethyl]-3-naphthalen-1-yl-2-naphthalen-1-ylmethyl-propionamide;

(S)-N-[2-(1H-Imidazol-4-yl)-1-(2-morpholin-4-yl-ethylcarbamoyl)-ethyl]-3-naphthalen-1-yl-2-naphthalen-1-ylmethyl-propionamide;

(S)-N-[1-(2-Diethylamino-ethylcarbamoyl)-2-(1H-imidazol-4-yl)-ethyl]-(3-naphthalen-1-yl-2-naphthalen-1-ylmethyl-propionamide;

(S)-N-[2-(1H-Imidazol-4-yl)-1-methylcarbamoyl-ethyl]-3-naphthalen-1-yl-2-naphthalen-1-ylmethyl-propionamide;

(S)-N-[1-Ethylcarbamoyl-2-(1H-imidazol-4-yl)-ethyl]-3-naphthalen-1-yl-2-naphthalen-1-ylmethyl-propionamide;

(S)-N-{2-(1H-Imidazol-4-yl)-1-[2-(4-sulfamoyl-phenyl)-ethylcarbamoyl]-ethyl}-3-naphthalen-1-yl-2-naphthalen-1-ylmethyl-propionamide;

(S)-2-[3-(Decahydro-naphthalen-1-yl)-2-(decahydro-naphthalen-1-ylmethyl)-propionylamino]-3-(1H-imidazol-4-yl)-propionic acid, methyl ester;

(S)-3-(1H-Imidazol-4-yl)-2-[3-(5,6,7,8-tetrahydro-naphthalen-1-yl)-2-(5,6,7,8-tetrahydro-naphthalen-1-ylmethyl)-propionylamino]-propionic acid, methyl ester;

(S)-N-[1-(2-Benzyloxy-ethylcarbamoyl)-2-(1H-imidazol-4-yl)-ethyl]-3-(5,6,7,8-tetrahydro-naphthalen-1-yl)-2-(5,6,7,8-tetrahydro-naphthalen-1-ylmethyl)-propionamide;

(S)-2-(3-Benzo[b]thiophen-3-yl-2-benzo[b]thiophen-3-ylmethyl-propionylamino)-3-(1H-imidazol-4-yl)-propionic acid, methyl ester;

(S)-3-(1H-Imidazol-4-yl)-2-(3-naphthalen-1-yl-2-naphthalen-1-ylmethyl-propionylamino)-thiopropionic acid, S-(2-acetylamino-ethyl) ester;

(S)-N-[1-(2-Cyano-ethylcarbamoyl)-2-(1H-imidazol-4-yl)-ethyl]-3-naphthalen-1-yl-2-naphthalen-1-ylmethyl-propionamide;

(S)-3-(1H-Imidazol-4-yl)-2-(3-naphthalen-1-yl-2-naphthalen-1-ylmethyl-propionylamino)-propionic acid, 2-hydroxy-ethyl ester;

(S)-N-[1-Dimethylcarbamoyl-2-(1H-imidazol-4-yl)-ethyl]-3-naphthalen-1-yl-2-naphthalen-1-ylmethyl-propionamide;

(S)-3-(1H-Imidazol-4-yl)-2-(3-naphthalen-1-yl-2-naphthalen-1-ylmethyl-propionylamino)-propionic acid, but-3-ynyl ester;

(S)-2-[3-(Decahydro-naphthalen-1-yl)-2-(decahydro-naphthalen-1-ylmethyl)-propionylamino]-3-(1H-imidazol-4-yl)-propionic acid, 2-cyano-ethyl ester;

(S)-N-[2-(1H-Imidazol-4-yl)-1-propylcarbamoyl-ethyl]-3-naphthalen-1-yl-2-naphthalen-1-ylmethyl-propionamide;

(S)-3-(1H-Imidazol-4-yl)-2-(3-naphthalen-1-yl-2-naphthalen-1-ylmethyl-propionylamino)-propionic acid, 2-imidazol-1-yl-ethyl ester;

(S)-3-(1H-Imidazol-4-yl)-2-(3-naphthalen-1-yl-2-naphthalen-1-ylmethyl-propionylamino)-propionic acid, but-3-enyl ester;

(S)-3-(1H-Imidazol-4-yl)-2-[3-(5,6,7,8-tetrahydro-naphthalen-1-yl)-2-(5,6,7,8-tetrahydro-naphthalen-1-ylmethyl)-propionylamino]-propionic acid, 2-cyano-ethyl ester;

(S)-N-[2-(1H-Imidazol-4-yl)-1-phenethylcarbamoyl-ethyl]-3-naphthalen-1-yl-2-naphthalen-1-ylmethyl-propionamide;

(S)-3-(1H-Imidazol-4-yl)-2-[methyl-(3-naphthalen-1-yl-2-naphthalen-1-ylmethyl-propiony)-amino]-propionic acid, methyl ester;

(S)-N-[1-Hydroxymethyl-2-(1H-imidazol-4-yl)-ethyl]-3-naphthalen-1-yl-2-naphthalen-1-ylmethyl-propionamide;

(S)-3-[1H-Imidazol-4-yl]-2-(3-naphthalen-1-yl-2-naphthalen-1-ylmethyl-propionylamino)-propionic acid, phenethyl ester;

(S)-3-(1H-Imidazol-4-yl)-2-(3-naphthalen-1-yl-2-naphthalen-1-ylmethyl-propionylamino)-propionic acid, 3-cyano-propyl ester;

(S)-3-(1H-Imidazol-4-yl)-2-(3-naphthalen-1-yl-2-naphthalen-1-ylmethyl-propionylamino)-propionic acid, 3-methyl-but-2-enyl ester;

(S)-3-(1H-Imidazol-4-yl)-2-(3-naphthalen-1-yl-2-naphthalen-1-ylmethyl-propylamino)-propionic acid, methyl ester;

(S)-3-(1H-Imidazol-4-yl)-2-(3-naphthalen-1-yl-2-naphthalen-1-ylmethyl-propionylamino)-propionic acid, methoxycarbonylmethyl ester;

(S)-3-(1H-Imidazol-4-yl)-2-(3-naphthalen-1-yl-2-naphthalen-1-ylmethyl-propionylamino)-propionic acid, cyanomethyl ester;

(S)-3-(1H-Imidazol-4-yl)-2-(3-naphthalen-1-yl-2-naphthalen-1-ylmethyl-propionylamino)-propionic acid, 2-(2-hydroxy-ethyldisulfanyl)-ethyl ester;

(S)-3-(3-Methoxymethyl-3H-imidazol-4-yl)-2-(3-naphthalen-1-yl-2-naphthalen-1-ylmethyl-propionylamino)-propionic acid, methyl ester;

(S)-3-(1H-Imidazol-4-yl)-2-(3-naphthalen-1-yl-2-naphthalen-1-ylmethyl-propionylamino)-propionic acid, 1-cyano-ethyl ester;

(S)-3-(1H-Imidazol-4-yl)-2-(3-naphthalen-1-yl-2-naphthalen-1-ylmethyl-propylamino)-propan-1-ol;

(S)-3-(1H-Imidazol-4-yl)-N-methyl-2-(3-naphthalen-1-yl-2-naphthalen-1-ylmethyl-propylamino)-propionamide;

(S)-N-[1-Methylcarbamoyl-2-(3-methyl-3H-imidazol-4-yl)-ethyl]-3-naphthalen-1-yl-2-naphthalen-1-ylmethyl-propionamide; and (S)-2-(2-Benzyl-3-naphthalen-1-yl-propionylamino)-3-(1H-imidazol-4-yl)-propionic acid, methyl ester; and corresponding isomers thereof; or a pharmaceutically acceptable salt thereof.

The compounds of Formula I are valuable inhibitors of the enzyme farnesyltransferase.

The protein:farnesyltransferase (PFT) or farnesyl protein transferase (FPT) inhibitory activity of compounds of Formula I was assayed in HEPES buffer (pH 7.4) containing 5 mM potassium phosphate and 20 $\mu$M $ZnCl_2$. The solution also contained 7 mM DTT, 1.2 mM $MgCl_2$. Assays were performed in 96 well plates (Wallec) and employed solutions composed of varying concentrations of a compound of Formula I in 100% DMSO. Upon addition of both substrates, radiolabeled farnesyl pyrophosphate ([1-$^3$H], specific activity 15–30 Ci/mmol, final concentration 0.12 $\mu$M) and (biotinyl)-Ahe-Tyr-Lys-Cys-Val-Ile-Met ([3aS[3a alpha, 4 beta, 6a alpha]-hexahydro-2-oxo-1H-thieno[3,4-d] imidazole-5-pentanoic acid]-[7-aminoheptanoic acid]-Thr-Lys-Cys-Val-Ile-Met) (final concentration 0.2 $\mu$M), the enzyme reaction was started by addition of 40-fold purified rat brain farnesyl protein transferase. After incubation at 37° C. for 30 minutes, the reaction was terminated by diluting the reaction 2.5-fold with a stop buffer containing 1.5 M magnesium acetate, 0.2 M $H_3PO_4$, 0.5% BSA, and streptavidin beads (Amersham) at a concentration of 1.3 mg/mL. After allowing the plate to settle for 30 minutes at room temperature, radioactivity was quantitated on a microBeta counter (Model 1450, Wallec). Compounds of Formula I show $IC_{50}$ values of 0.06 to 60 $\mu$M in this assay and are thus valuable inhibitors of protein:farnesyltransferase enzyme which may be used in the medical treatment of tissue proliferative diseases, including cancer and restenosis. The assay was also carried out without 5 mM potassium phosphate.

Gel Shift Assay

Twenty-four hours after planting 2×10$^6$ ras-transformed cells per treatment condition, the farnesylation inhibitor is added at varying concentrations. Following an 18-hour incubation period, cells are lysed in phosphate-buffered saline containing 1% Triton X-100, 0.5% sodium deoxycholate, and 0.1% SDS, pH 7.4 in the presence of several protease inhibitors (PMSF, antipain, leupeptin, pepstatin A, and aprotinin all at 1 $\mu$g/mL). Ras protein is immunoprecipitated from the supernatants by the addition of 3 $\mu$g v-H-ras Ab-2 (Y13-259 antibody from Oncogene Science). After overnight immunoprecipitation, 30 $\mu$L of a 50% protein G-Sepharose slurry (Pharmacia) is added followed by 45-minute incubation. Pellets are resuspended in 2× tris-glycine loading buffer (Novex) containing 5% B-mercaptoethanol and then denatured by 5 minutes boiling prior to electrophoresis on 14% Tris-glycine SDS gels. Using Western transfer techniques, proteins are transferred to nitrocellulose membranes followed by blocking in blocking buffer. Upon overnight incubation with primary antibody (pan-ras Ab-2 from Oncogene Science), an antimouse HRP conjugate secondary antibody (Amersham) is employed for detection of the ras protein. Blots are developed using ECL techniques (Amersham).

The data in Table 1 show farnesyl protein transferase inhibitory activity, and activity in the gel shift assay against ras protein of selected compounds of Formula I.

TABLE 1

Biological Activity of Compounds of Formula I

| Example | Compound | Farnesyl Protein Transferase Inhibition | | Inhibition of Ras Farnesylation (Minimum Effective Dose, $\mu$M) | |
|---|---|---|---|---|---|
| | | Hepes IC$_{50}$ ($\mu$M) | Hepes/5 mM PO$_4^{-3}$ IC$_{50}$ ($\mu$M) | H-ras Me 12/+ Cells | H-ras-NIH3T3 Cells |
| 1 | (S)-3-(1H-Imidazol-4-yl)-2-(3-naphthalen-1-yl-2-naphthalen-1-ylmethyl-propionylamino)-propionic acid, methyl ester | 0.26 | 0.30 | 2.5 | 5.0 |
| 2 | (R)-3-(1H-Imidazol-4-yl)-2-(3-naphthalen-1-yl-2-naphthalen-1-ylmethyl propionylamino)-propionic acid, methyl ester | 12 | 10 | | |
| 3 | (S)-3-(1H-Imidazol-4-yl)-2-(3-naphthalen-1-yl-2-naphthalen-1-ylmethyl-propionylamino)-propionic acid | 1.0 | 2.3 | | |
| 4 | (R)-3-(1H-Imidazol-4-yl)-2-(3-naphthalen-1-yl-2-naphthalen-1-ylmethyl-propionylamino)-propionic acid | 6.1 | 19.5 | | |
| 5 | (S)-3-(1H-Imidazol-4-yl)-2-(3-naphthalen-1-yl-2-naphthalen-1-ylmethyl-propionylamino)-propionic acid, ethyl ester | 0.13 | 0.13 | 2.5 | |
| 6 | (S)-3-(3-Methyl-3H-imidazol-4-yl)-2-(3-naphthalen-1-yl-2-naphthalen-1-ylmethyl-propionylamino)-propionic acid, methyl ester | 0.42 | 0.22 | 1 | 2.5 |
| 7 | (S)-3-(1H-Imidazol-4-yl)-2-(3-naphthalen-1-yl-2-naphthalen-1-ylmethyl-propionylamino)-propionic acid, propyl ester | 0.11 | 0.10 | 5.0 | |
| 8 | (S)-3-(1H-Imidazol-4-yl)-2-(3-naphthalen-1-yl-2-naphthalen-1-ylmethyl-propionylamino)-propionic acid, isopropyl ester | 0.18 | 0.16 | 5.0 | 5.0 |
| 9 | (S)-3-(1H-Imidazol-4-yl)-2-(3-naphthalen-1-yl-2-naphthalen-1-ylmethyl-propionylamino)-propionic acid, butyl ester | 1.3 | 1.1 | | |
| 10 | (S)-3-(1H-Imidazol-4-yl)-2-(3-naphthalen-1-yl-2-naphthalen-1 ylmethyl-propionylamino)-propionic acid, benzyl ester | 4.2 | 2.9 | | |
| 11 | (S)-3-(1H-Imidazol-4-yl)-2-(3-naphthalen-1-yl-2-naphthalen-1-ylmethyl-propionylamino)-propionic acid, cyclohexyl ester | 20 | 14 | | |
| 12 | (S)-3-(1H-Imidazol-4-yl)-2-(3-naphthalen-1-yl-2-naphthalen-1-ylmethyl-propionylamino)-propionic acid, cyclopropylmethyl ester | 0.40 | 0.25 | | |
| 13 | (S)-3-(1H-Imidazol-4-yl)-2-(3-naphthalen-1-yl-2-naphthalen-1-ylmethyl-propionylamino)-propionic acid, 2-butyl-1H-imidazol-4-ylmethyl ester | 2.1 | 1.7 | | |
| 14 | (S)-3-(1H-Imidazol-4-yl)-2-(3-naphthalen-1-yl-2-naphthalen-1-ylmethyl-propionylamino)-propionic acid, ±-sec-butyl ester | 0.82 | 0.54 | | |
| 15 | (S)-3-(1H-Imidazol-4-yl)-2-(3-naphthalen-1-yl-2-naphthalen-1-ylmethyl-propionylamino)-propionic acid, allyl ester | 0.40 | 0.20 | | 25.0 |
| 16 | (S)-3-(1H-Imidazol-4-yl)-2-(3-naphthalen-1-yl-2-naphthalen-1-ylmethyl-propionylamino)-propionic | 0.50 | 0.59 | | |

TABLE 1-continued

Biological Activity of Compounds of Formula I

| Example | Compound | Farnesyl Protein Transferase Inhibition | | Inhibition of Ras Farnesylation (Minimum Effective Dose, $\mu$M) | |
|---|---|---|---|---|---|
| | | Hepes IC$_{50}$ ($\mu$M) | Hepes/5 mM PO$_4^{-3}$ IC$_{50}$ ($\mu$M) | H-ras Me 12/+ Cells | H-ras-NIH3T3 Cells |
| 17 | (S)-3-(1H-Imidazol-4-yl)-2-(3-naphthalen-1-yl-2-naphthalen-1-ylmethyl-propionylamino)-propionic acid, 2-cyanoethyl ester | 0.08 | 0.07 | | 10 |
| 18 | (S)-3-(1H-Imidazol-4-yl)-2-(3-naphthalen-1-yl-2-naphthalen-1-ylmethyl-propionylamino)-propionic acid, 2-benzyloxyethyl ester | 0.57 | 0.54 | | |
| 19 | (S)-3-(1H-Imidazol-4-yl)-2-(3-naphthalen-1-yl-2-naphthalen-1-ylmethyl-propionylamino)-propionic acid, 2-thiophen-2-yl-ethyl ester | 1.1 | 1.1 | | |
| 20 | (S)-3-(1H-Imidazol-4-yl)-2-(3-naphthalen-1-yl-2-naphthalen-1-ylmethyl-propionylamino)-propionic acid, thiophen-3-ylmethyl ester | 3.5 | 2.4 | | |
| 21 | (S)-3-(1H-Imidazol-4-yl)-2-(3-naphthalen-1-yl-2-naphthalen-1-ylmethyl-propionylamino)-propionic acid, 2-diethylamino-ethyl ester | 21 | 9.0 | | |
| 22 | (S)-3-(1H-Imidazol-4-yl)-2-(3-naphthalen-1-yl-2-naphthalen-1-ylmethyl-propionylamino)-propionic acid, 2-morpholin-4-yl-ethyl ester | 5.8 | 4.3 | | |
| 23 | (S)-N-[1-(2-Benzyloxy-ethylcarbamoyl)-2-(1H-imidazol-4-yl)-ethyl]-3-naphthalen-1-yl-2-naphthalen-1-ylmethyl-propionamide | 0.74 | 0.55 | 5.0 | |
| 24 | (S)-N-[1-Carbamoyl-2-(1H-imidazol-4-yl)-ethyl]-3-naphthalen-1-yl-2-naphthalen-1-ylmethyl-propionamide | 5.3 | 3.8 | | |
| 25 | (S)-N-[2-(1H-Imidazol-4-yl)-1-(2-imidazol-1-yl-ethylcarbamoyl)-ethyl]-3-naphthalen-1-yl-2-naphthalen-1-ylmethyl-propionamide | 1.9 | 1.5 | | |
| 26 | (S)-N-[1-(2-Ethylsulfanyl-ethylcarbamoyl)-2-(1H-imidazol-4-yl)-ethyl]-3-naphthalen-1-yl-2-naphthalen-1-ylmethyl-propionamide | 12 | 8.7 | | |
| 27 | (S)-N-{2-(1H-Imidazol-4-yl)-1-[2-(1H-imidazol-4-yl)-ethylcarbamoyl]-ethyl}-3-naphthalen-1-yl-2-naphthalen-1-ylmethyl-propionamide | 4.8 | 3.9 | 10.0 | |
| 28 | (S)-N-[2-(1H-Imidazol-4-yl)-1-(3-imidazol-1-yl)-propylcarbamoyl)-ethyl]-3-naphthalen-1-yl-2-naphthalen-1-ylmethyl-propionamide | 8.1 | 4.2 | | |
| 29 | (S)-N-[1-(2-Hydroxy-ethylcarbamoyl)-2-(1H-imidazol-4-yl)-ethyl]-3-naphthalen-1-yl-2-naphthalen-1-ylmethyl-propionamide | 3.2 | 3.7 | | |
| 30 | (S)-N-[2-(1H-Imidazol-4-yl)-1-isopropylcarbamoyl-ethyl]-3-naphthalen-1-yl-2-naphthalen-1-ylmethyl-propionamide | 4.6 | 3.5 | | |
| 31 | (S)-N-[2-(1H-Imidazol-4-yl)-1-(2-morpholin-4-yl-ethylcarbamoyl)-ethyl]-3-naphthalen-1-yl-2-naphthalen-1-ylmethyl-propionamide | 26 | 15 | | |
| 32 | (S)-N-[1-(2-Diethylamino-ethylcarbamoyl)-2-(1H-imidazol-4-yl)-ethyl]-(3-naphthalen-1-yl-2-naphthalen-1-ylmethyl-propionamide | 19 | 14 | | |
| 33 | (S)-N-[2-(1H-Imidazol-4-yl)-1-methylcarbamoyl-ethyl]-3-naphthalen-1-yl-2-naphthalen-1- | 0.61 | 0.44 | 1.0 | 1.0 |

TABLE 1-continued

Biological Activity of Compounds of Formula I

| Example | Compound | Farnesyl Protein Transferase Inhibition | | Inhibition of Ras Farnesylation (Minimum Effective Dose, μM) | |
|---|---|---|---|---|---|
| | | Hepes IC$_{50}$ (μM) | Hepes/5 mM PO$_4^{-3}$ IC$_{50}$ (μM) | H-ras Me 12/+ Cells | H-ras-NIH3T3 Cells |
| 34 | ylmethyl-propionamide (S)-N-[1-Ethylcarbamoyl-2-(1H-imidazol-4-yl)-ethyl]-3-naphthalen-1-yl-2-naphthalene-1-ylmethyl-propionamide | 2.9 | 2.0 | | |
| 35 | (S)-N-{2-(1H-Imidazol-4-yl)-1-[2-(4-sulfamoyl-phenyl)-ethylcarbamoyl]-ethyl}-3-naphthalen-1-yl-2-naphthalen-1-ylmethyl-propionamide | 15 | 14 | | |
| 36 | (S)-2-[3-(Decahydro-naphthalen-1-yl)-2-(decahydro-naphthalen-1-ylmethyl)-propionylamino]-3-(1H-imidazol-4-yl)-propionic acid, methyl ester | 0.31 | 0.37 | 25.0 | |
| 37 | (S)-3-(1H-Imidazol-4-yl)-2-[3-(5,6,7,8-tetrahydro-naphthalen-1-yl)-2-(5,6,7,8-tetrahydro-naphthalen-1-ylmethyl)-propionylamino]-propionic acid, methyl ester | 0.42 | 0.18 | 10.0 | |
| 38 | (S)-N-[1-(2-Benzyloxy-ethylcarbamoyl)-2-(1H-imidazol-4-yl)-ethyl]-3-(5,6,7,8-tetrahydro-naphthalen-1-yl)-2-(5,6,7,8-tetrahydro-naphthalen-1-ylmethyl)-propionamide | 0.78 | 0.85 | | |
| 39 | (S)-2-(3-Benzo[b]thiophen-3-yl-2-benzo[b]thiophen-3-ylmethyl-propionylamino)-3-(1H-imidazol-4-yl)-propionic acid, methyl ester | 1.2 | 0.97 | | |
| 40 | (S)-3-(1H-Imidazol-4-yl)-2-(3-naphthalen-1-yl-2-naphthalen-1-ylmethyl-propionylamino)-thiopropionic acid, S-(2-acetylamino-ethyl)ester | 2.6 | 3.2 | | |
| 41 | (S)-N-[1-(2-Cyano-ethylcarbamoyl)-2-(1H-imidazol-4-yl)-ethyl]-3-naphthalen-1-yl-2-naphthalen-1-ylmethyl-propionamide | 0.97 | 0.71 | | 5 |
| 42 | (S)-3-(1H-Imidazol-4-yl)-2-(3-naphthalen-1-yl-2-naphthalen-1-ylmethyl-propionylamino)-propionic acid, 2-hydroxy-ethyl ester, trifluoroacetate salt | 1.8 | 1.3 | | |
| 43 | (S)-N-[1-Dimethylcarbamoyl-2-(1H-imidazol-4-yl)-ethyl]-3-naphthalen-1-yl-2-naphthalen-1-ylmethyl-propionamide | 5.6 | 3.8 | | |
| 44 | (S)-3-(1H-Imidazol-4-yl)-2-(3-naphthalen-1-yl-2-naphthalen-1-ylmethyl-propionylamino)-propionic acid, but-3-ynyl ester, trifluoroacetate salt | 0.23 | 0.21 | | |
| 45 | (S)-2-[3-(Decahydro-naphthalen-1-yl)-2-(decahydro-naphthalen-1-ylmethyl)-propionylamino]-3-(1H-imidazol-4-yl)-propionic acid, 2-cyano-ethyl ester | 0.49 | 0.32 | | |
| 46 | (S)-N-(2-(1H-Imidazol-4-yl)-1-propylcarbamoyl-ethyl)-3-naphthalen-1-yl-2-naphthalen-1-ylmethyl)-propionamide | 4.9 | 5.6 | | |
| 47 | (S)-3-(1H-Imidazol-4-yl)-2-(3-naphthalen-1-yl-2-naphthalen-1-ylmethyl-propionylamino)-propionic acid, 2-imidazol-1-yl-ethyl ester | 1.1 | 1.4 | | |
| 48 | (S)-3-(1H-Imidazol-4-yl)-2-(3-naphthalen-1-yl-2-naphthalen-1- | 1.2 | 1.3 | | |

TABLE 1-continued

Biological Activity of Compounds of Formula I

| | | Farnesyl Protein Transferase Inhibition | | Inhibition of Ras Farnesylation (Minimum Effective Dose, $\mu M$) | |
|---|---|---|---|---|---|
| Example | Compound | Hepes IC$_{50}$ ($\mu M$) | Hepes/5 mM PO$_4^{-3}$ IC$_{50}$ ($\mu M$) | H-ras Me 12/+ Cells | H-ras-NIH3T3 Cells |
| | ylmethyl-propionylamino)-propionic acid, but-3-enyl ester | | | | |
| 49 | (S)-3-(1H-Imidazol-4-yl)-2-[3-(5,6,7,8-tetrahydro-naphthalen-1-yl)-2-(5,6,7,8-tetrahydro-naphthalen-1-ylmethyl)-propionylamino]-propionic acid, 2-cyano-ethyl ester | 0.29 | 0.37 | | |
| 50 | (S)-N-[2-(1H-Imidazol-4-yl)-1-phenethylcarbamoyl-ethyl]-3-naphthalen-1-yl-2-naphthalen-1-ylmethyl)-propionamide | 4.8 | 6.0 | | |
| 51 | (S)-3-(1H-Imidazol-4-yl)-2-[methyl-(3-naphthalen-1-yl-2-naphthalen-1-ylmethyl-propionyl)-amino]-propionic acid, methyl ester, trifluoroacetate salt | 2.0 | 2.2 | | 5 |
| 52 | (S)-N-[1-Hydroxymethyl-2-(1H-imidazol-4-yl)-ethyl)-3-naphthalen-1-yl-2-naphthalen-1-ylmethyl-propionamide | 3.0 | 3.4 | | 25 |
| 53 | (S)-3-(1H-Imidazol-4-yl)-2-(3-naphthalen-1-yl-2-naphthalen-1-ylmethyl-propionylamino)-propionic acid, phenethyl ester | 0.07 | 0.06 | | 25 |
| 54 | (S)-3-(1H-Imidazol-4-yl)-2-(3-naphthalen-1-yl-2-naphthalen-1-ylmethyl-propionylamino)-propionic acid, 3-cyano-propyl ester | 0.44 | 0.37 | | |
| 55 | (S)-3-(1H-Imidazol-4-yl)-2-(3-naphthalen-1-yl-2-naphthalen-1-ylmethyl-propionylamino)-propionic acid, 3-methyl-but-2-enyl ester | 5.3 | 4.3 | | |
| 56 | (S)-3-(1H-Imidazol-4-yl)-2-(3-naphthalen-1-yl-2-naphthalen-1-ylmethyl-propylamino)-propionic acid, methyl ester | 0.37 | 0.36 | | |
| 57 | (S)-3-(1H-Imidazol-4-yl)-2-(3-naphthalen-1-yl-2-naphthalen-1-ylmethyl-propionylamino)-propionic acid, methoxycarbonylmethyl ester | 5.5 | 4.1 | | |
| 58 | (S)-3-(1H-Imidazol-4-yl)-2-(3-naphthalen-1-yl-2-naphthalen-1-ylmethyl-propionylamino)-propionic acid, cyanomethyl ester | 0.40 | 0.51 | | |
| 59 | (S)-3-(1H-Imidazol-4-yl)-2-(3-naphthalen-1-yl-2-naphthalen-1-ylmethyl-propionylamino)-propionic acid, 2-(2-hydroxy-ethyl-disulfanyl)-ethyl ester | 1.3 | 1.0 | | |
| 60 | (S)-3-(3-Methoxymethyl-3H-imidazol-4-yl)-2-(3-naphthalen-1-yl-2-naphthalen-1-ylmethyl-propionylamino)-propionic acid, methyl ester | 0.93 | 1.0 | | |
| 61 | (S)-3-(1H-Imidazol-4-yl)-2-(3-naphthalen-1-yl-2-naphthalen-1-ylmethyl-propionylamino)-propionic acid, 1-cyano-ethyl ester | 0.64 | 0.61 | | |
| 62 | (S)-3-(1H-Imidazol-4-yl)-2-(3-naphthalen-1-yl-2-naphthalen-1-ylmethyl-propylamino)-propan-1-ol | 0.55 | 0.50 | | |
| 63 | (S)-3-(1H-Imidazol-4-yl)-N-methyl-2-(3-naphthalen-1-yl-2-naphthalen-1-ylmethyl-propylamino)-propionamide | 0.20 | 0.24 | | |
| 64 | (S)-N-[1-Methylcarbamoyl-2-(3-methyl-3H-imidazol-4-yl)-ethyl]-3-naphthalen-1-yl-2-naphthalen-1-yl- | 0.61 | 0.46 | | |

TABLE 1-continued

Biological Activity of Compounds of Formula I

| Example | Compound | Farnesyl Protein Transferase Inhibition | | Inhibition of Ras Farnesylation (Minimum Effective Dose, µM) | |
|---|---|---|---|---|---|
| | | Hepes IC$_{50}$ (µM) | Hepes/5 mM PO$_4^{-3}$ IC$_{50}$ (µM) | H-ras Me 12/+ Cells | H-ras-NIH3T3 Cells |
| 65 | ylmethyl-propionamide (S)-2-(2-Benzyl-3-naphthalen-1-yl-propionylamino)-3-(1H-imidazol-4-yl)-propionic acid, methyl ester | 1.6 | 2.9 | | 25 |

A compound of Formula Ia

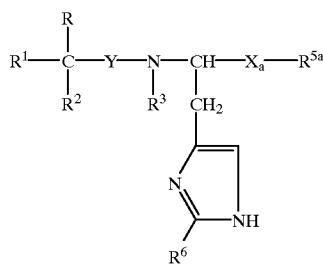

Ia wherein R is hydrogen or alkyl; $R^1$ and $R^2$ may be the same or different and are selected from the group consisting of:

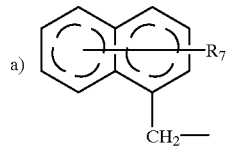

wherein the bicyclic ring may be aromatic, or partially or completely saturated, and $R^7$ may be 1 to 3 substituents selected from the group consisting of:
hydrogen,
alkyl,
alkenyl,
alkoxy,
thioalkoxy,
hydroxy,
mercapto,
halogen,
nitro,

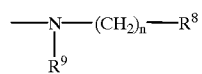

wherein $R^8$ and $R^9$ may be the same or different and are selected from the group consisting of:
hydrogen,
alkyl, or $R^8$ and $R^9$ are taken together with N to form a 5- or 6-membered ring optionally containing a heteroatom selected from the group consisting of: S, O, and N—$R^{10}$ wherein $R^{10}$ is hydrogen or alkyl, and n is zero or an integer of one to four,

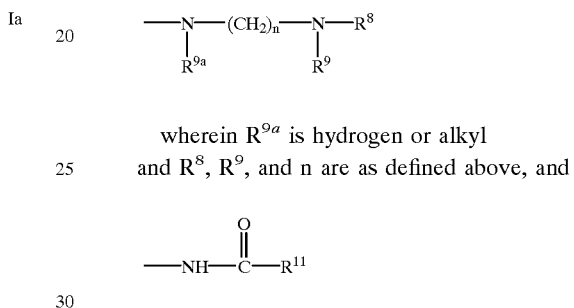

wherein $R^{9a}$ is hydrogen or alkyl
and $R^8$, $R^9$, and n are as defined above, and

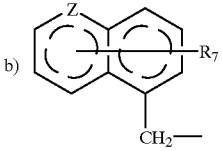

wherein $R^{11}$ is selected from the group consisting of:
hydrogen,
alkyl, and
aryl,

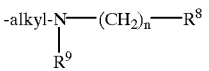

wherein the bicyclic ring may be aromatic, or partially or completely saturated, and Z is selected from the group consisting of:

$NR^{12}$ wherein $R^{12}$ is hydrogen, alkyl, or

-alkyl-N—(CH$_2$)$_n$—$R^8$
          |
          $R^9$ wherein $R^8$, $R^9$, and n are as defined above, or $R^{12}$ is absent,
O,
S,
SO, and
SO$_2$, and
Z may be at other positions in the bicyclic ring system provided that when the bicyclic ring is aromatic, Z is not at the point of attachment of the CH$_2$ unit and $R^{12}$ is absent, and $R^7$ is as defined above, c) 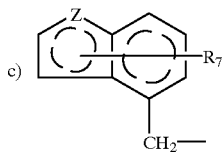

wherein the bicyclic ring may be aromatic, or partially or completely saturated, and Z and $R^7$ are as defined above and $R^{12}$ may be present, d) 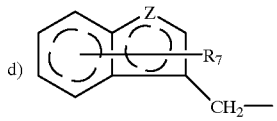

wherein the bicyclic ring may be aromatic, or partially or completely saturated, and Z and $R^7$ are as defined above, and $R^{12}$ may be present, e) 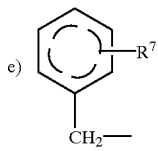

wherein the monocyclic may be aromatic, or partially or completely saturated, and $R^7$ is as defined above with the proviso that $R^1$ and $R^2$ are not both a monocyclic ring, and f) 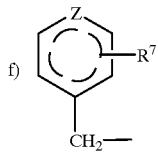

wherein the monocyclic ring may be aromatic, or partially or completely saturated, and $R^7$ and Z are as defined above with the proviso that $R^1$ and $R^2$ are not both a monocyclic ring;

$R^3$ is hydrogen or alkyl;

$X_a$ is

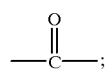;

Y is

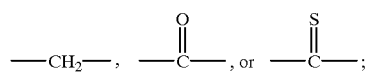;

$R^{5a}$ is selected from the group consisting of:
—$OR^{14a}$ wherein $R^{14a}$ is selected from the group consisting of:
alkyl,
alkenyl,
alkynyl,
cycloalkyl,
cycloalkylalkyl,
haloalkyl,
hydroxyalkyl,
mercaptoalkyl,
cyanoalkyl,
nitroalkyl,
alkoxyalkyl,
arylalkyl,
heteroarylalkyl,
benzyloxyalkyl,
thioalkoxyalkyl,
acetamidoalkyl,
$HOCH_2CH_2$—S—S—$CH_2CH_2$—,

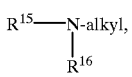

wherein $R^{15}$ and $R^{16}$ may be the same or different and are selected from the group consisting of:
hydrogen,
alkyl or $R^{15}$ and $R^{16}$ are taken together with N to form a 5- or 6-membered ring optionally containing a heteroatom selected from the group consisting of: S, O, and N—$R^{10}$ wherein $R^{10}$ is as defined above,
$HO_2C$-alkyl,
alkyl-$O_2C$-alkyl, and

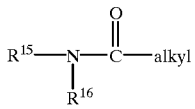

wherein $R^{15}$ and $R^{16}$ are as defined above,
—S—$R^{14a}$ wherein $R^{14a}$ is as defined above;

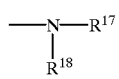

wherein $R^{17}$ and $R^{18}$ may be the same or different and are selected from the group consisting of:
hydrogen,
alkyl,
alkenyl,
alkynyl,
cyanoalkyl,
hydroxyalkyl,
alkoxyalkyl,
arylalkyl,
heteroarylalkyl,
benzyloxyalkyl,
cycloalkyl,
cycloalkylalkyl,
haloalkyl,
mercaptoalkyl,
nitroalkyl,
thioalkoxyalkyl, acetamidoalkyl,

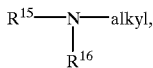

wherein $R^{15}$ and $R^{16}$ may be the same or different and are selected from the group consisting of:

hydrogen, alkyl or $R^{15}$ and $R^{16}$ are taken together with N to form a 5- or 6-membered ring optionally containing a heteroatom selected from the group consisting of: S, O, and N—$R^{10}$ wherein $R^{10}$ is as defined above, or $R^{17}$ and $R^{18}$ are taken together with N to form a 5- or 6-membered ring optionally containing a heteroatom selected from the group consisting of: S, O, and N—$R^{10}$ wherein $R^{10}$ is as defined above, —NH—$OR^{10}$ wherein $R^{10}$ is as defined above, alkyl, alkenyl, and arylalkyl; and $R^6$ is hydrogen, —SR where R is as defined above, —OR where R is as defined above, or

wherein R and $R^a$ may be the same or different and are as defined above for R; and corresponding isomers thereof; or a pharmaceutically acceptable salt thereof may be prepared by reacting a compound of Formula II

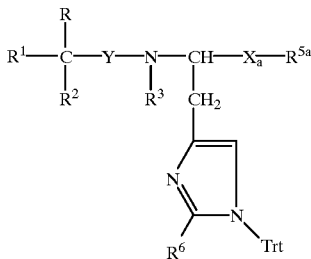

II wherein Trt is $(C_6H_5)_3$—C— and R, $R^1$, $R^2$, $R^3$, $X_a$, Y, $R^{5a}$ and $R^6$ are as defined above with an acid such as, for example, 80% to 85% acetic acid and the like at about 90° C. for about 0.5 hours to afford a compound of Formula Ia. Preferably, the reaction is carried out with 80% to 85% acetic aced at about 90° C. for about 0.5 hours.

A compound of Formula Ib

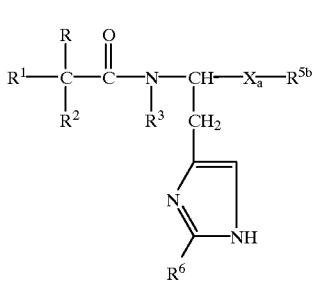

Ib wherein $R^{5b}$ is OH and R, $R^1$, $R^2$, $R^3$, $X_a$, and $R^6$ as defined above may be prepared by reacting a compound of Formula Ic

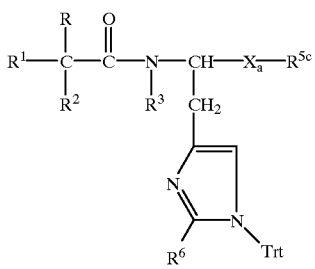

Ic wherein $R^{5c}$ is $OCH_3$ or $SCH_3$ and R, $R^1$, $R^2$, $R^3$, $X_a$, $R^6$ and Trt are as defined above with a base such as, for example, 1N sodium hydroxide and the like in a solvent such as, for example, methanol, dioxane, and the like at about room temperature for about 2 hours to afford a compound of Formula Ic-1.

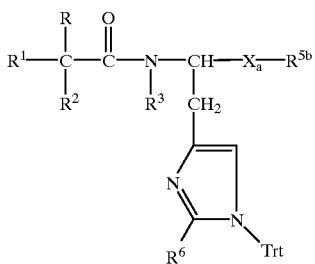

Ic-1 wherein R, $R^1$, $R^2$, $R^3$, $X_a$, $R^{5b}$, $R^6$, and Trt are as defined above. Preferably, the reaction is carried out with 1N sodium hydroxide in methanol at about room temperature for about 2 hours. A compound of Formula Ic-1 is converted to a compound of Formula Ib using methodology used to prepare a compound of Formula Ia from a compound of Formula II to afford a compound of Formula Ib.

A compound of Formula Id

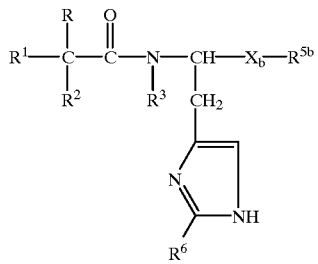

wherein $X_b$ is —CH$_2$— and R, $R^1$, $R^2$, $R^3$, $R^{5b}$, and $R^6$ are as defined above may be prepared by reacting a compound of Formula Ia with a metal hydride such as, for example, lithium borohydride and the like in a solvent such as, for example, tetrahydrofuran and the like at about 0° C. to about room temperature to afford a compound of Formula Id. Preferably, the reaction is carried out with lithium borohydride in tetrahydrofuran at about 25° C.

A compound of Formula Ie

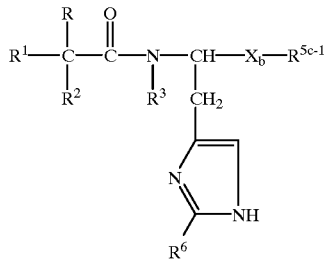

wherein $R^{5c-1}$ is $OR^{14a}$ wherein $R^{14a}$ is selected from the group consisting of:
alkyl,
alkenyl,
alkynyl,
cycloalkyl,
cycloalkylalkyl,
haloalkyl,
hydroxyalkyl,
mercaptoalkyl,
cyanoalkyl,
nitroalkyl,
alkoxyalkyl,
arylalkyl,
heteroarylalkyl,
benzyloxyalkyl,
thioalkoxyalkyl,
acetamidoalkyl,
HOCH$_2$CH$_2$—S—S—CH$_2$CH$_2$—,

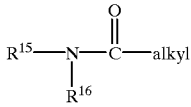

wherein $R^{15}$ and $R^{16}$ may be the same or different and are selected from the group consisting of:
hydrogen,
alkyl or $R^{15}$ and $R^{16}$ are taken together with N to form a 5- or 6-membered ring optionally containing a heteroatom selected from the group consisting of: S, O, and N—$R^{10}$ wherein $R^{10}$ is as defined above,
HO$_2$C-alkyl,
alkyl-O$_2$C-alkyl, and

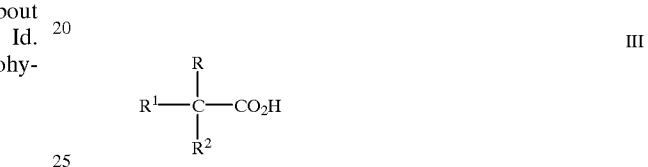

wherein $R^{15}$ and $R^{16}$ are as defined above;

and R, $R^1$, $R^2$, $R^3$, $X_b$, and $R^6$ are as defined above may be prepared by reacting a compound of Formula III

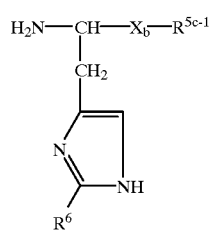

wherein R, $R^1$, and $R^2$ are as defined above with a compound of Formula IV

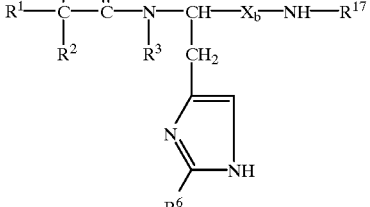

wherein $X_b$, $R^{5c-1}$, and $R^6$ are as defined above in the presence of a coupling reagent such as, for example, N,N-dicyclohexylcarbodiimide (DCC) and 1-hydroxybenzotriazole (HOBt) and the like in a solvent such as, for example, tetrahydrofuran (THF) at about room temperature for about 12 hours to afford a compound of Formula Ie. Preferably, the reaction is carried out with DCC and HOBt in THF at about room temperature.

A compound of Formula I$_f$ wherein $R^{17}$ is

R, $R^1$, $R^2$, $R^3$, $X_b$, and $R^6$ are as defined above may be prepared from a compound of Formula V

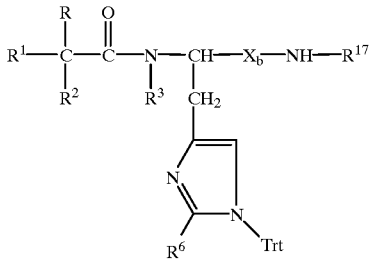

wherein R, $R^1$, $R^2$, $R^3$, $X_b$, $R^6$, $R^{17}$, and Trt are as defined above using methodology used to prepare a compound of Formula Ia from a compound of Formula II to afford a compound of Formula $I_f$.

A compound of Formula $I_g$

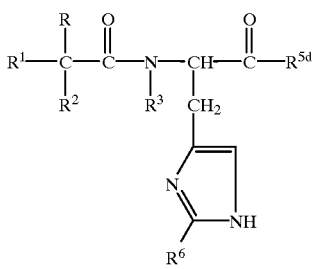

wherein $R^{5d}$ is
alkyl,
alkenyl, and
arylalkyl, and
R, $R^1$, $R^2$, $R^3$, and $R^6$ are as defined above may be prepared by reacting a compound of Formula III with a compound of Formula VI

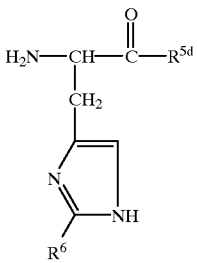

wherein $R^{5d}$ and $R^6$ are as defined above using methodology used to prepare a compound of Formula Ie from a compound of Formula III and a compound of Formula IV to afford a compound of Formula $I_g$.

A compound of Formula $I_h$

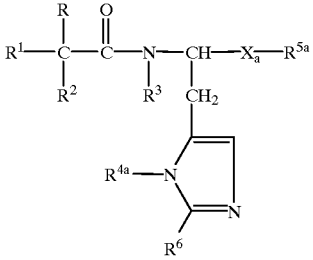

wherein $R^{4a}$ is selected from the group consisting of:

alkyl,
alkenyl,
alkynyl,
benzyl,
alkyl chain wherein the alkyl chain may be interrupted by a heteroatom selected from the group consisting of: S, O, and N—$R^{10}$ wherein $R^{10}$ is hydrogen or alkyl,

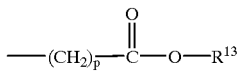

wherein p is an integer of one to four, and $R^{13}$ is alkyl or benzyl, and

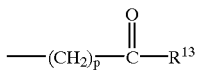

wherein p and $R^{13}$ are as defined above, and

R, $R^1$, $R^2$, $R^3$, $X_a$, $R^{5a}$, and $R^6$ are as defined above may be prepared from a compound of Formula VII

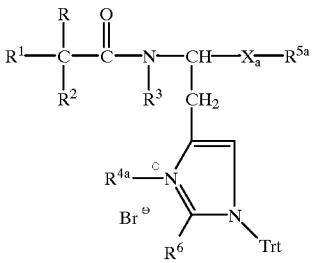

wherein R, $R^1$, $R^2$, $R^3$, $R^{4a}$, $R^{5a}$, $R^6$, $X_a$, and Trt are as defined above in the presence of 80% acetic acid to afford a compound of Formula $I_h$.

A compound of Formula $I_i$

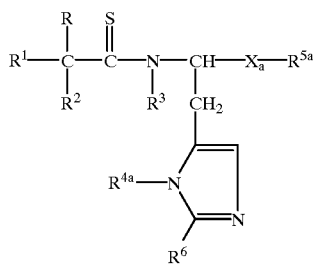

wherein R, $R^1$, $R^2$, $R^3$, $R^{4a}$, $R^{5a}$, $R^6$, and $X_a$ are as defined above may be prepared from a compound of Formula $I_h$ in the presence of Lawesson's Reagent (2,4-bis(4-methoxyphenyl)-1,3-dithia-2,4-diphosphetane-2,4-disulfide) and pyridine to afford a compound of Formula $I_i$ A compound of Formula $I_j$

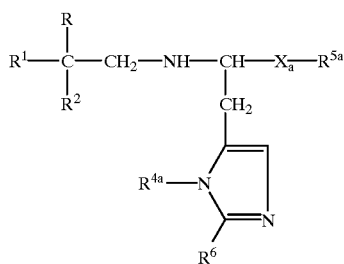

wherein R, $R^1$, $R^2$, $R^{4a}$, $R^{5a}$, $R^6$, and $X_a$ are as defined above by reacting a compound of Formula VIII

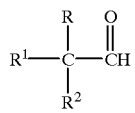

wherein R, $R^1$, and $R^2$ are as defined above with a compound of Formula IX

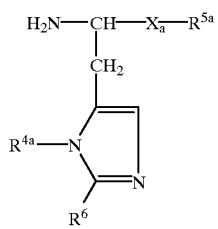

wherein $R^{4a}$, $R^{5a}$, $R^6$, and $X_a$ are as defined above in the presence of a metal hydride such as, for example, sodium cyanoborohydride and the like in the presence of molecular sieves to afford a compound of Formula $I_j$.

A compound of Formula $I_k$

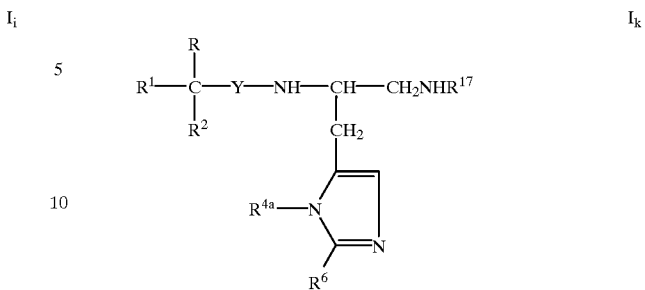

wherein Y is —$CH_2$—,

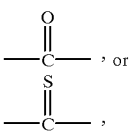

R, $R^1$, $R^2$, $R^{4a}$, $R^6$, and $R^{17}$ are as defined above may be prepared from a compound of Formula X.

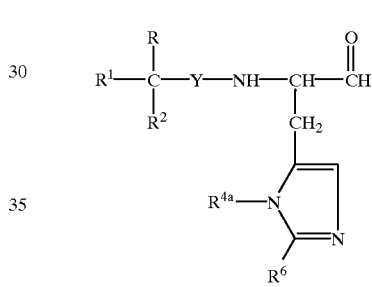

wherein R, $R^1$, $R^2$, $R^{4a}$, $R^6$, and Y are as defined above and a compound of Formula XI

wherein $R^{17}$ is as defined above using the methodology used to prepare a compound of Formula $I_j$ from a compound of Formula VIII and a compound of Formula IX to afford a compound of Formula $I_k$.

A compound of Formula $I_l$

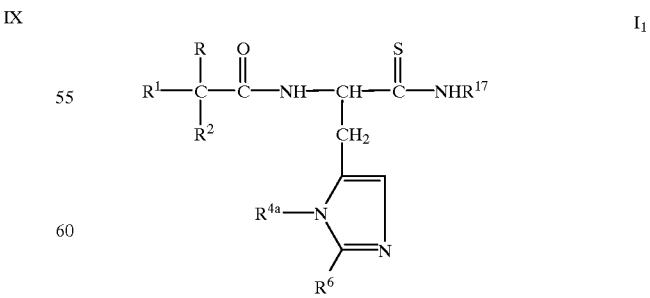

wherein R, $R^1$, $R^2$, $R^{4a}$, $R^6$, and $R^{17}$ are as defined above may be prepared from a compound of Formula III and a compound of Formula XII

XII

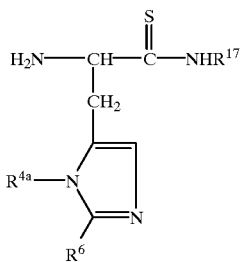

wherein $R^{4a}$, $R^6$, and $R^{17}$ are as defined above using methodology used to prepare a compound of Formula $I_e$ from a compound of Formula III and a compound of Formula IV to afford a compound of Formula $I_f$.

A compound of Formula II may be prepared from a compound of Formula XIII

XIII

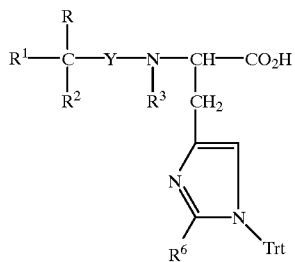

wherein R, $R^1$, $R^2$, $R^3$, $R^6$, Y, and Trt are as defined above and a compound of Formula XIV $$R^{5a}H \qquad \text{XIV}$$

wherein $R^{5a}$ is as defined above using standard methodology such as the methodology used to prepare a compound of Formula $I_e$ from a compound of Formula III and a compound of Formula IV to afford a compound of Formula II.

A compound of Formula XIII may be prepared from a compound of Formula XV

XV

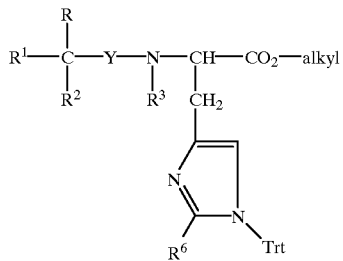

wherein R, $R^1$, $R^2$, $R^3$, $R^6$, Y, and Trt are as defined above in the presence of a dilute base such as, for example, dilute aqueous sodium hydroxide and the like at room temperature to afford a compound of Formula XIII.

A compound of Formula $XV_a$

XV$_a$

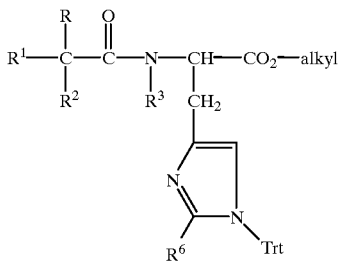

wherein R, $R^1$, $R^2$, $R^3$, $R^6$, and Trt are as defined above may be prepared by reacting a compound of Formula III and a compound of Formula XVI

XVI

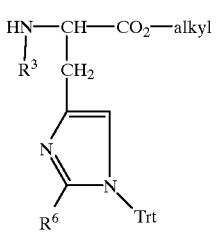

wherein $R^3$, $R^6$, and Trt are as defined above using methodology used to prepare a compound of Formula $I_e$ from a compound of Formula III and a compound of Formula IV to afford a compound of Formula $XV_a$.

A compound of Formula $XV_b$

XV$_b$

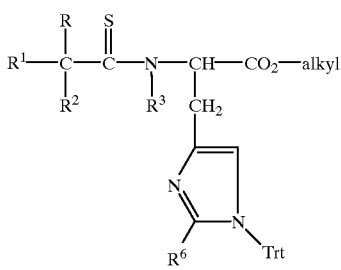

wherein R, $R^1$, $R^2$, $R^3$, $R^6$, and Trt are as defined above may be prepared from a compound of Formula $XV_a$ using the methodology used to prepare compound of Formula $I_i$ from a compound of Formula $I_h$ to afford a compound of Formula $XV_b$.

A compound of Formula $XV_c$

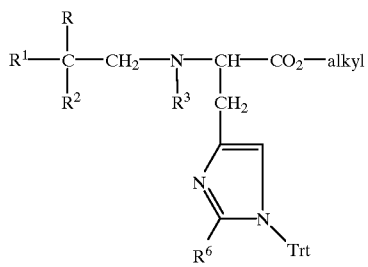
XV$_c$ wherein R, $R^1$, $R^2$, $R^3$, $R^6$, and Trt are as defined above may be prepared from a compound of Formula VIII and a compound of Formula XVI using the methodology used to prepare a compound of Formula $I_j$ from a compound of Formula VIII and a compound of Formula IX to afford a compound of Formula $XV_c$.

A compound of Formula VIII may be prepared from a compound of Formula XVII

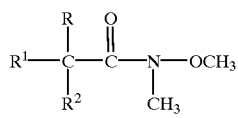
XVII wherein R, $R^1$, and $R^2$ are as defined above by treatment with a metal hydride such as, for example, lithium aluminum hydride and the like at about 0° C. to afford a compound of Formula VIII.

A compound of Formula XVII may be prepared from a compound of Formula III and N,0-dimethyl-hydroxylamine in the presence of methyl chloroformate to afford a compound of Formula XVII.

A compound of Formula III may be prepared from a compound of Formula XVIII

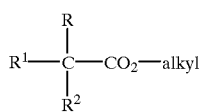
XVIII wherein R, $R^1$, and $R^2$ are as defined above using methodology used to prepare a compound of Formula XIII from a compound of Formula XV to afford a compound of Formula III.

A compound of $XVIII_a$

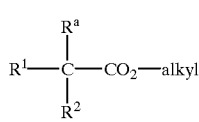
XVIII$_a$ wherein $R^a$ is alkyl and $R^1$ and $R^2$ are as defined above may be prepared by reacting a compound of Formula XIX

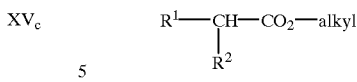
XIX wherein $R^1$ and $R^2$ are as defined above with a compound of Formula XX $R^a$Br     XX wherein $R^a$ is as defined above in the presence of a base such as, for example, sodium hydride and the like to afford a compound of Formula $XVIII_a$.

A compound of Formula XIX may be prepared from a compound of Formula XXI

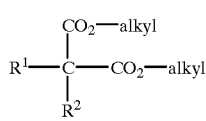
XXI wherein $R^1$ and $R^2$ are as defined above in the presence of about one equivalent of a base such as, for example, sodium hydroxide and the like and a solvent such as, for example, dioxane and the like, and after acidification with an acid such as, for example, hydrochloric acid and the like heating to effect decarboxylation to afford a compound of Formula XIX.

A compound of Formula XXI may be prepared from a compound of Formula XXII

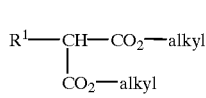
XXII wherein $R_1$ is as defined above by reaction with a compound of Formula XXIII $R^2$Br     XXIII wherein $R^2$ is as defined above using methodology used to prepare a compound of Formula $XVIII_a$ from a compound of Formula XIX and a compound of Formula XX to afford a compound of Formula XXI.

A compound of Formula XXII may be prepared from a dialkylmalonate in the presence of a compound of Formula XXIV $R^1$Br     XXIV wherein $R^1$ is as defined above using methodology used to prepare a compound of Formula $XVIII_a$ from a compound of Formula XIX and a compound of Formula XX to afford a compound of Formula XXII.

A compound of Formula XXIV may be prepared from a compound of Formula XXV $R^1$OH     XXV wherein $R^1$ is as defined above by treatment with $PBr_3$ to afford a compound of Formula XXIV.

A compound of Formula XXV may be prepared from a compound of Formula XXVI $R^{1a}$—$CO_2$H     XXVI wherein $R^{1a}$ is $R^1$ in which the $CH_2$ group is absent by treatment with a metal hydride such as, for example, lithium aluminum hydride and the like at room temperature to afford a compound of Formula XXV.

A compound of Formula IV may be prepared from a compound of Formula XXVII

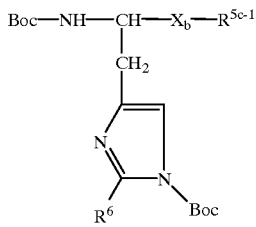

XXVII wherein Boc is tertiary butoxycarbonyl, and $R^{5c-1}$, $R^6$, and $X_b$ are as defined above by treatment with an acid such as, for example, trifluoroacetic acid and the like in the presence of a solvent such as, for example, dichloromethane and the like to afford a compound of Formula IV.

A compound of Formula XXVII may be prepared from a compound of Formula XXVIII

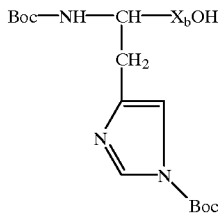

XXVIII wherein Boc and $X_b$ are as defined above by reaction with a compound of Formula XXIX $R^{5c-1}Br$  XXIX wherein $R^{5c-1}$ is as defined above in the presence of a base such as, for example, sodium hydride and the like to afford a compound of Formula XXVII.

A compound of Formula XXVIII may be prepared from a compound of Formula XXX

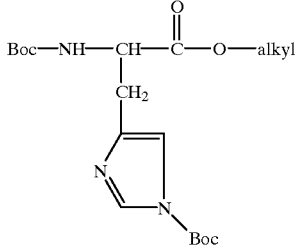

XXX wherein Boc is as defined above by treatment with a metal hydride reagent such as, for example, lithium aluminum hydride and the like in a solvent such as, for example, tetrahydrofuran and the like to afford a compound of Formula XXVIII.

A compound of Formula $V_a$

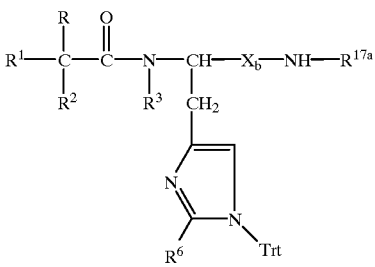

Va wherein $R^{17a}$ is

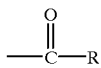

and R, $R^1$, $R^2$, $R^3$, $R^6$, $X_b$, and Trt are as defined above may be prepared from a compound of Formula XXXI

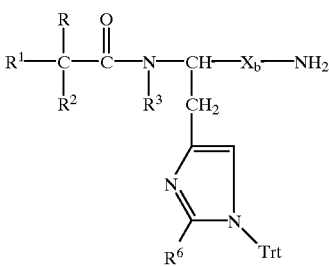

XXXI wherein R, $R^1$, $R^2$, $R^3$, $R^6$, $X_b$, and Trt are as defined above by reaction with a compound of Formula XXXII $R^{17a}Cl$  XXXII wherein $R^{17a}$ is as defined above in the presence of a base such as, for example, triethylamine and the like to afford a compound of Formula $V_a$.

A compound of Formula XXXI may be prepared from a compound of Formula XXXIII

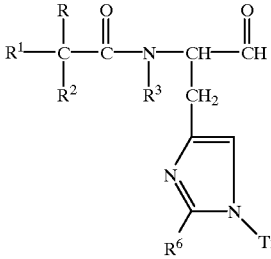

XXXIII wherein R, $R^1$, $R^2$, $R^3$, $R^6$, and Trt are as defined above by treatment with ammonia in the presence of a metal hydride such as, for example, sodium cyanoborohydride and the like and a solvent such as, for example, 2-propanol and the like to afford a compound of Formula XXXI.

A compound of Formula $V_b$

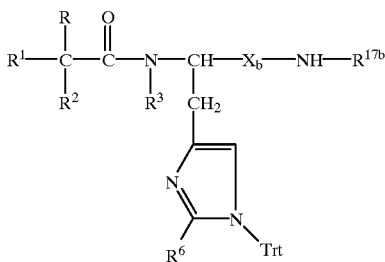
Vb wherein $R^{17b}$ is

and R, $R^1$, $R^2$, $R^3$, $R^6$, $X_b$, and Trt are as defined above may be prepared from a compound of Formula XXXI by treatment with a compound of Formula XXXIV

   XXXIV wherein R is as defined above in the presence of a base such as, for example, triethylamine and the like to afford a compound of Formula $V_b$.

A compound of Formula VI may be prepared from a compound of Formula XXXV

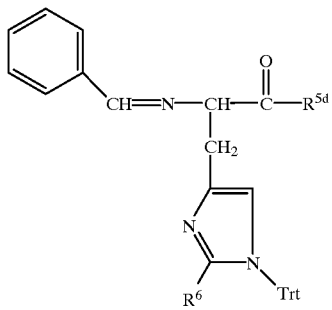
XXXV wherein $R^{5d}$, $R^6$, and Trt are as defined above by treatment with 80% acetic acid at about 90° C. for about 0.5 hour to afford a compound of Formula VI.

A compound of Formula XXXV may be prepared from a compound of Formula XXXVI

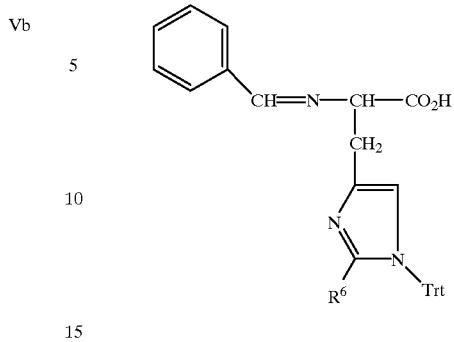
XXXVI wherein $R^6$ and Trt are as defined above by treatment with about 2 mol of a compound of Formula XXXVII

Li   XXXVII wherein $R^{5d}$ is as defined above in the presence of a solvent such as, for example, tetrahydrofuran and the like to afford a compound of Formula XXXV.

A compound of Formula VII may be prepared from a compound of Formula XXXVIII

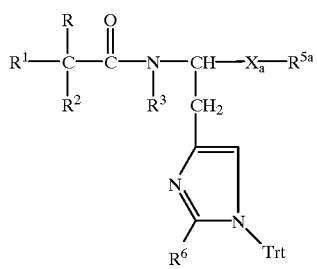
XXXVIII wherein R, $R^1$, $R^2$, $R^3$, $R^{5a}$, $R^6$, $X_a$, and Trt are as defined above by treatment with a compound of Formula XXXIX

Br   XXXIX wherein $R^{4a}$ is as defined above in the presence of a solvent such as, for example, dichloromethane and the like to afford a compound of Formula VII.

A compound of Formula IX may be prepared from a compound of Formula XL

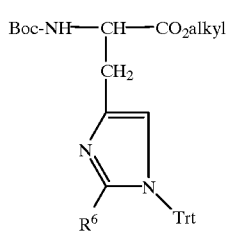
XL wherein $R^6$, Boc, and Trt are as defined above by treatment with a compound of Formula XXXIX followed by removal of the Trt group with 80% acetic acid at about 90° C. for about 0.5 hour and subsequent removal of the Boc group with an acid such as, for example, hydrogen chloride gas and the like in a solvent such as, for example, dichloromethane and the like to afford a compound of Formula IX.

A compound of Formula X may be prepared from a compound of Formula XLI

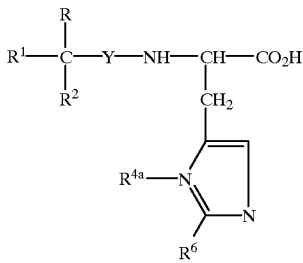

XLI wherein R, $R^1$, $R^2$, $R^{4a}$, $R^6$, and Y are as defined above by treatment with methyl chloroformate, N,O-dimethylhydroxylamine, and piperidine followed by treatment with lithium aluminum hydride in tetrahydrofuran to afford a compound of Formula X.

A compound of Formula XLI may be prepared from a compound of Formula XLII

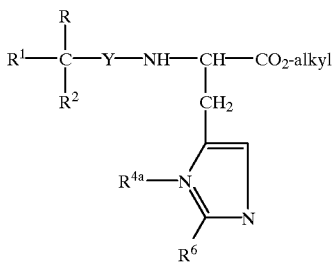

XLII wherein R, $R^1$, $R^2$, $R^{4a}$, $R^6$, and Y are as defined above by treatment with a dilute base such as, for example, dilute sodium hydroxide and the like to afford a compound of Formula XLI.

A compound of Formula XII may be prepared from a compound of Formula XLIII

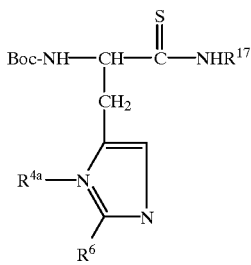

XLIII wherein Boc, $R^{4a}$, $R^6$, and $R^{17}$ are as defined above by treatment with an acid such as, for example, hydrogen chloride gas and the like in a solvent such as, for example, dichloromethane and the line to afford a compound of Formula XII.

A compound of Formula XLIII may be prepared from a compound of Formula XLIV

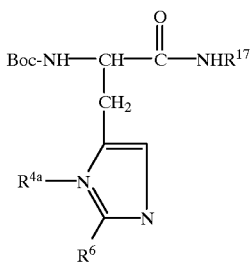

XLIV wherein Boc, $R^{4a}$, $R^6$, and $R^{17}$ are as defined above using the methodology used to prepare a compound of Formula $I_i$ from a compound of Formula $I_h$ to afford a compound of Formula XLIII.

A compound of Formula XLIV may be prepared by reacting a compound of Formula XLV

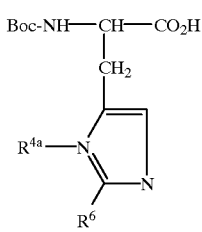

XLV wherein Boc, $R^{4a}$, and $R^6$ are as defined above with a compound of Formula XI in the presence of methyl chloroformate and a base such as, for example, triethylamine and the like to afford a compound of Formula XLIV.

A compound of Formula III wherein $R^1$ and $R^2$ are bicyclic rings, which are partially or completely saturated, may be prepared from the corresponding aromatic bicyclic compound using conventional reducing conditions known in the art.

Compounds of Formula VIII, XI, XIV, XXII, XXVI, XXIX, XXXII, XXXIV, XXXVII, and XXXIX are either known or capable of being prepared by methods known in the art.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg, preferably 10 mg to 100 mg according to the particular application and the potency of the active component. The composition can, if desired, also contain other compatible therapeutic agents.

In therapeutic use as anticancer agents and as agents to treat restenosis and psoriasis, and as antiviral agents, the compounds utilized in the pharmaceutical method of this invention are administered at the initial dosage of about 1 mg to about 50 mg per kilogram daily. A daily dose range of about 5 mg to about 25 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired.

The following nonlimiting examples illustrate the inventors' preferred methods for preparing the compounds of the invention.

EXAMPLE 1

(S)-3-(1H-Imidazol-4-yl)-2-(3-naphthalen-1-yl-2-naphthalen-1-ylmethyl-propionylamino)-propionic acid, methyl ester Step (a) Preparation of: Bis-(1-naphthylmethyl)-acetyl-His(Trt)-OCH$_3$ A solution of 2.0 g (4.9 mmol) of N$^{im}$-tritylhistidine methyl ester (His(Trt)-OCH$_3$) in 20 mL of tetrahydrofuran (THF) was treated with 1.75 g (4.9 mmol) of bis-(1-naphthylmethyl)-acetyl chloride (*J. Med. Chem.*, 35:1032 (1992)) followed by 0.7 mL (4.9 mmol) of triethylamine (Et$_3$N) and the mixture stirred at room temperature for 2 days. The mixture was diluted with ethyl acetate (EtOAc) and washed with H$_2$O, a saturated solution of sodium bicarbonate (NaHCO$_3$), and a saturated solution of sodium chloride (NaCl). Drying over magnesium sulfate (MgSO$_4$) and removal of the solvent under reduced pressure left 3.52 g of the crude product which was used directly in the following reaction.

Step (b) Preparation of: (S)-3-(1H-Imidazol-4-yl)-2-(3-naphthalen-1-yl-2-naphthalen-1-ylmethyl-propionylamino)-propionic acid methyl ester A solution of 3.52 g (4.8 mmol) of bis-(1-naphthylmethyl)-acetyl-His(Trt)-OCH$_3$ in 250 mL of 80% acetic acid was heated at 87° C. for 15 minutes. The solvent was removed under reduced pressure and the residue taken up in EtOAc, then washed with a saturated solution of NaHCO$_3$ and a saturated solution of NaCl. Drying over MgSO$_4$ and removal of the solvent under reduced pressure left the crude product. Chromatography on silica gel, eluting with chloroform/methyl alcohol (CHCl$_3$/MeOH) (95/5) gave 1.51 g of the product as a cream foam. The structure was confirmed by nuclear magnetic resonance spectroscopy (NMR) and mass spectroscopy; (m+H)$^+$=492.

EXAMPLE 2

(R)-3-(1H-Imidazol-4-yl)-2-(3-naphthalen-1-yl-2-naphthalen-1-ylmethyl-propionylamino)-propionic acid, methyl ester Following the procedure of Example 1, but using D-N$^{im}$-tritylhistidine methyl ester (D-HIS(Trt)-OCR$_3$) there was obtained 1.4 g of the product as a white foam. The structure was confirmed by NMR and mass spectroscopy; (m+H)$^+$=492.

EXAMPLE 3

(S)-3-(1H-Imidazol-4-yl)-2-(3-naphthalen-1-yl-2-naphthalen-1-ylmethyl-propionylamino)-propionic acid A solution of 1.37 g (2.8 mmol) of the ester from Example 1 in 15 mL MeOH and 15 mL dioxane was treated with 6.0 mL (6.0 mmol) of 1N sodium hydroxide (NaOH) and stored at room temperature for 2 hours. The solvent was removed under reduced pressure and the residue taken up in H$_2$O. Acidification with 6.0 mL (6.0 mmol) of 1N hydrochloric acid (HCl) gave a gum. The solvent was decanted and nhe gum recrystallized from acetone/$H_2O$ to give 0.59 g of a white solid, mp 193–195° C. The structure was confirmed by NMR and mass spectroscopy; $(m+H)^+=478$.

EXAMPLE 4
(R)-3-(1H-Imidazol-4-yl)-2-(3-naphthalen-1-yl-2-naphthalen-1-ylmethyl-propionylamino)-propionic acid Following the procedure of Example 3, but using the ester of Example 2, there was obtained 0.78 g of the product as a white solid, mp 187–189° C. The structure was confirmed by NMR and mass spectroscopy; $(m+H^+)=478$.

EXAMPLE 5
(S)-3-(1H-Imidazol-4-yl)-2-(3-naphthalen-1-yl-2-naphthalen-1-ylmethyl-propionylamino)-propionic acid, ethyl ester A solution of 0.5 g (1.5 mmol) of bis-(1-naphthylmethyl)-acetic acid, 0.77 g (3.0 mmol) of histidine ethyl ester dihydrochloride (His-OEt•2 HCl), and 0.22 g (1.6 mmol) of 1-hydroxybenzotriazole (HOBt) in 20 mL of THF was treated with 0.85 mL (6.0 mmol) of $Et_3N$ followed by 0.33 g (1.6 mmol) of N,N'-dicyclo hexylcarbodiimide (DCC) and the solution allowed to stir at room temperature overnight. The mixture was filtered and the solvent removed under reduced pressure. The residue was taken up in EtOAc and washed with a saturated solution of $NaHCO_3$, then with a saturated solution of NaCl. Drying over $MgSO_4$ and removal of the solvent under reduced pressure gave the crude product. Chromatography on silica gel, eluting with a gradient of methylene chloride ($CH_2Cl_2$) to $CH_2Cl_2$/MeOH (96/4) gave 0.15 g of the product as a white foam. The structure was confirmed by NMR and mass spectroscopy; $(m+H)^+=506$.

EXAMPLE 6
(S)-3-(3-Methyl-3H-imidazol-4-yl)-2-(3-naphthalen-1-yl-2-naphthalen-1-ylmethyl-propionylamino)-propionic acid, methyl ester A suspension of 0.5 g (2.3 mmol) of $\pi$-$N^{im}$-methyl histidine methyl ester dihydrochloride (($\pi$-MeHis)-OMe•2 HCl) in 20 mL of THF was cooled in ice and 0.82 g (2.3 mmol) of bis-(1-naphthylmethyl-acetyl chloride added, followed by 1.0 mL (6.9 mmol) of $Et_3N$. After 0.5 hour at 0° C., the mixture was allowed to stir at room temperature overnight. The mixture was diluted with EtOAc and washed twice with $H_2O$, then a saturated solution of $NaHCO_3$, then a saturated solution of NaCl. Drying over $MgSO_4$ and removal of the solvent under reduced pressure left the crude product. Chromatography on silica gel, eluting with chloroform ($CHCl_3$)/MeOH (97/3) followed by preparative high performance liquid chromatography (HPLC) gave a white solid when triturated with acetonitrile ($CH_3CN$). There was obtained 53 mg of the product as a white solid, mp 199–200° C. The structure was confirmed by NMR and mass spectroscopy; $(m+H)^+=506$.

EXAMPLE 7
(S)-3-(1H-Imidazol-4-yl)-2-(3-naphthalen-1-yl-2-naphthalen-1-ylmethyl-propionylamino)-propionic acid, propyl ester Step (a) Preparation of: Bis-(1-Naphthylmethyl)-acetyl-His (Trt)-$OCH_3$ A solution of 3.13 g (9.2 mmol) of bis-(1-naphthylmethyl)-acetic acid 4.0 g (9.2 mmol) of His(Trt)-$OCH_3$, and 1.35 g (10.0 mmol) of HOBt in 100 mL THF was treated with 1.39 mL (10.0 mmol) of $Et_3N$ followed by 2.09 g (10.0 mmool) of DCC. The mixture was stirred at room temperature overnight, then filtered and diluted with EtOAc. The EtOAc was washed with a saturated solution of $NaHCO_3$, then a saturated solution of NaCl. Drying over $MgSO_4$ and removal of the solvent under reduced pressure gave 7.55 g of the crude product which was used directly in the following step.

Step (b) Preparation of: Bis-(1-Naphthylmethyl)-acetyl-His (Trt)•HCl

A solution of 7.55 g (assume 9.2 mmol) of the crude material from Step (a) above in 50 mL MeOH and 50 mL THF was treated with a solution of 1.84 g (46 mmol) of sodium hydroxide (NaOH) in 5 mL $H_2O$ and allowed to stir at room temperature overnight. The solvent was removed under reduced pressure and the residue taken up in $H_2O$ and acidified to the Congo red color change with dilute HCl. The aqueous mixture was extracted with EtOA and the EtOAc washed with 1N HCl, then a saturated solution of NaCl. On drying over $MgSO_4$ and filtering, the product started to precipitate from the filtrate. There was obtained 4.0 g of the product as a white solid, mp 190–195° C. The structure was confirmed by mass spectroscopy; $(m+H)^+=720$.

Step (c) Preparation of: Bis-(1-Naphthylmethyl)-acetyl-His (Trt)-O-n-propyl

A solution of 0.5 g (0.7 mmol) of the acid•HCl from Step (b) above, 0.2 g (1.54 mmol) of diisopropylethylamine, and 0.44 g (0.77 mmol) of n-propanol in 20 mL $CH_2Cl_2$ was cooled in ice and stirred for 15 minutes. The BOP reagent (benzotriazol-1-yloxy-tris(dimethylamino)-phosphonium hexafluorophosphate) (0.34 g, 0.77 mmol) was then added and the solution stirred at room temperature overnight. The mixture was then washed twice with a saturated solution of $NaHCO_3$, then a saturated solution of NaCl. Drying over $MgSO_4$ and removal of the solvent under reduced pressure left the crude product which was used directly in the next step.

Step (d) Preparation of: (S)-3-(1H-Imidazol-4-yl)-2-(3-naphthalen-1-yl-2-naphthalen-1-ylmethyl-propionylamino)-propionic acid, propyl ester The material from Step (c) above was dissolved in 12 mL of 85% acetic acid and heated at 90° C. for 2 hours. The solvent was removed under reduced pressure and the residue taken up in EtOAc and washed twice with a saturated solution of $NaHCO_3$, then with a saturated solution of NaCl. Drying over $MgSO_4$ and removal of the solvent under reduced pressure left the crude product. Chromatography on silica gel, eluting with a gradient of $CH_2Cl_2$ to $CH_2Cl_2$/MeOH (96/4) gave 0.18 g of the product as a white foam. The structure was confirmed by NMR and mass spectroscopy; $(m+H)^+=520$.

EXAMPLE 8
(S)-3-(1H-Imidazol-4-yl)-2-(3-naphthalen-1-yl-2-naphthalen-1-ylmethyl-propionylamino)-propionic acid, isopropyl ester Following the procedure of Example 7, but using isopropyl alcohol, there was obtained 0.2 g of the product as a white foam. The structure was confirmed by NMR and mass spectroscopy; $(m+H)^+=520$.

EXAMPLE 9
(S)-3-(1H-Imidazol-4-yl)-2-(3-naphthalen-1-yl-2-naphthalen-1-ylmethyl-propionylamino)-propionic acid, butyl ester Following the procedure of Example 7, but using n-butyl alcohol, there was obtained 0.12 g of the product as a white foam. The structure was confirmed by NMR and mass spectroscopy; $(m+H)^+=534$.

EXAMPLE 10
(S)-3-(1H-Imidazol-4-yl)-2-(3-naphthalen-1-yl-2-naphthalen-1-ylmethyl-propionylamino)-propionic acid, benzyl ester Following the procedure of Example 7, but using benzyl alcohol, there was obtained 0.3 g of the product as a white foam. The structure was confirmed by NMR and mass spectroscopy; (m+H)$^+$=568.

EXAMPLE 11
(S)-3-(1H-Imidazol-4-yl)-2-(3-naphthalen-1-yl-2-naphthalen-1-ylmethyl-propionylamino)-propionic acid, cyclohexyl ester Following the procedure of Example 7, but using cyclohexyl alcohol, there was obtained 0.21 g of the product as a white foam. The structure was confirmed by NMR and mass spectroscopy; (m+H)$^+$=560.

EXAMPLE 12
(S)-3-(1H-Imidazol-4-yl)-2-(3-naphthalen-1-yl-2-naphthalen-1-ylmethyl-propionylamino)-propionic acid, cyclopropylmethyl ester Following the procedure of Example 7, but using cyclopropylmethyl alcohol, there was obtained 0.15 g of the product as a white foam. The structure was confirmed by NMR and mass spectroscopy; (m+H)$^+$=532.

EXAMPLE 13
(S)-3-(1H-Imidazol-4-yl)-2-(3-naphthalen-1-yl-2-naphthalen-1-ylmethyl-propionylamino)-propionic acid, 2-butyl-1H-imidazol-4-ylmethyl ester Following the procedure of Example 7, but using 2-butyl-1H-imidazol-4-ylmethyl alcohol, there was obtained 0.08 g of the product as a white foam. The structure was confirmed by NMR and mass spectroscopy; (m+H)$^+$=614.

EXAMPLE 14
(S)-3-(1H-Imidazol-4-yl)-2-(3-naphthalen-1-yl-2-naphthalen-1-ylmethyl-propionylamino)-propionic acid, (±)-sec-butyl ester Following the procedure of Example 7, but using (±)-sec-butyl alcohol, there was obtained 0.12 g of the product as a white foam. The structure was confirmed by NMR and mass spectroscopy; (m+H)$^+$=534.

EXAMPLE 15
(S)-3-(1H-Imidazol-4-yl)-2-(3-naphthalen-1-yl-2-naphthalen-1-ylmethyl-propionylamino)-propionic acid, allyl ester Following the procedure of Example 7, but using allyl alcohol, there was obtained 0.15 g of a white foam. The structure was confirmed by NMR and mass spectroscopy; (m+H)$^+$=518.

EXAMPLE 16
(S)-3-(1H-Imidazol-4-yl)-2-(3-naphthalen-1-yl-2-naphthalen-1-ylmethyl-propionylamino)-propionic acid, prop-2-ynyl ester Following the procedure of Example 7, but using prop-2-ynyl alcohol, there was obtained 0.24 g of a white solid, mp 187–189° C. The structure was confirmed by NMR and mass spectroscopy; (m+H)$^+$=516.

EXAMPLE 17
(S)-3-(1H-Imidazol-4-yl)-2-(3-naphthalen-1-yl-2-naphthalen-1-ylmethyl-propionylamino)-propionic acid, 2-cyanoethyl ester Following the procedure of Example 7, but using 2-cyanoethanol, there was obtained 0.12 g of the product as a white foam. The structure was confirmed by NMR and mass spectroscopy; (m+H)$^+$=531.

EXAMPLE 18
(S)-3-(1H-Imidazol-4-yl)-2-(3-naphthalen-1-yl-2-naphthalen-1-ylmethyl-propionylamino)-propionic acid, 2-benzyloxyethyl ester Following the procedure of Example 7, but using 2-benzyloxyethanol, there was obtained 0.12 g of the product as a white foam. The structure was confirmed by NMR and mass spectroscopy; (m+H)$^+$=612.

EXAMPLE 19
(S)-3-(1H-Imidazol-4-yl)-2-(3-naphthalen-1-yl-2-naphthalen-1-ylmethyl-propionylamino)-propionic acid, 2-thiophen-2-yl-ethyl ester Following the procedure of Example 7, but using benzotriazol-1-yloxy-tripyrrolidino phosphonium hexafluorophosphate (PyBOP) as the coupling agent and using 2-thiophen-2-yl-ethyl alcohol, there was obtained 60 mg of the product as a white solid, mp 203–206° C. The structure was confirmed by NMR and mass spectroscopy; (m+H)$^+$=588.

EXAMPLE 20
(S)-3-(1H-Imidazol-4-yl)-2-(3-naphthalen-1-yl-2-naphthalen-1-ylmethyl-propionylamino)-propionic acid, thiophen-3-ylmethyl ester Following the procedure of Example 7, but using PyBOP as the coupling agent and using 2-thiophen-3-ylmethyl alcohol, there was obtained 0.12 g of the product as a white solid, mp 200–203° C. The structure was confirmed by NMR and mass spectroscopy; (m+H)$^+$=574.

EXAMPLE 21
(S)-3-(1H-Imidazol-4-yl)-2-(3-naphthalen-1-yl-2-naphthalen-1-ylmethyl-propionylamino)-propionic acid, 2-diethylamino-ethyl ester Following the procedure of Example 7, but using PyBOP as the coupling agent and using 2-diethylamino ethanol, there was obtained 0.22 g of the product as a white foam. The structure was confirmed by NMR and mass spectroscopy; (m+H)$^+$=577.

EXAMPLE 22
(S)-3-(1H-Imidazol-4-yl)-2-(3-naphthalen-1-yl-2-naphthalen-1-ylmethyl-propionylamino)-propionic acid, 2-morpholin-4-yl-ethyl ester Following the procedure of Example 7, but using PyBOP as the coupling agent and using 2-morpholin-4-yl-ethanol, there was obtained 0.12 g of the product as a white foam. The structure was confirmed by NMR and mass spectroscopy; (m+H)$^+$=591.

EXAMPLE 23
(S)-N-[1-(2-Benzyloxy-ethylcarbamoyl)-2-(1H-imidazol-4-yl)-ethyl]-3-naphthalen-1-yl-2-naphthalen-1-ylmethyl-propionamide A solution of 0.5 g (0.7 mmol) of bis-(1-naphthylmethyl)-acetyl-His(Trt)•HCl and 0.1 g (0.77 mmol) of HOBt in 20 mL THF was treated with 0.16 g (0.77 mmol) of DCC, 0.13 g (0.7 mmol) of 2-benzyloxyethylamine•HCl, and then with 0.24 mL (1.7 mmol) of Et$_3$N. The mixture was stirred at room temperature overnight. The mixture was filtered and the filtrate diluted with EtOAc and washed with H$_2$O, a saturated solution of NaHCO$_3$, then a saturated solution of NaCl. Drying over MgSO$_4$ and removal of the solvent under reduced pressure gave the trityl amide.

This was taken up in 12 mL of 85% acetic acid and heated at 90° C. for 2 hours. The solvent was removed under reduced pressure and the residue taken up in EtOAc and washed twice with a saturated solution of NaHCO$_3$, then with a saturated solution of NaCl. Drying over MgSO$_4$ and removal of the solvent under reduced pressure gave the crude product. Chromatography on silica gel, eluting with a

EXAMPLE 24
(S)-N-[1-Carbamoyl-2-(1H-imidazol-4-yl)-ethyl]-3-naphthalen-1-yl-2-naphthalen-1-ylmethyl-propionamide Following the procedure of Example 23, but using a THF solution of ammonia ($NH_3$) as the amine, there was obtained 0.12 g of the product obtained as an amorphous solid. The structure was confirmed by NMR and mass spectroscopy; $(m+H)^+=477$.

EXAMPLE 25
(S)-N-[2-(1H-Imidazol-4-yl)-1-(2-imidazol-1-yl-ethylcarbamoyl)-ethyl]-3-naphthalen-1-yl-2-naphthalen-1-ylmethyl-propionamide Following the procedure of Example 23, but using 2-(1-imidazoyl)-ethylamine, there was obtained 0.14 g of the product as a white foam. The structure was confirmed by NMR and mass spectroscopy; (m+H)+571.

EXAMPLE 26
(S)-N-[1-(2-Ethylsulfanyl-ethylcarbamoyl)-2-(1H-imidazol-4-yl)-ethyl]-3-naphthalen-1-yl-2-naphthalen-1-ylmethyl-propionamide Following the procedure of Example 23, but using 2-(ethylthio)-ethylamine•HCl, there was obtained 0.3 g of the product as a white foam. The structure was confirmed by NMR and mass spectroscopy; $(m+H)^+=565$.

EXAMPLE 27
(S)-N-{2-(1H-Imidazol-4-yl)-1-[2-(1H-imidazol-4-yl)-ethylcarbamoyl]-ethyl}-3-naphthalen-1-yl-2-naphthalen-1-ylmethyl-propionamide Following the procedure of Example 23, but using the BOP reagent for coupling, and using histamine, there was obtained 0.1 g of the product as a white solid. The structure was confirmed by NMR and mass spectroscopy; $(m+H)^+=571$.

EXAMPLE 28
(S)-N-[2-(1H-Imidazol-4-yl)-1-(3-imidazol-1-yl)-propylcarbamoyl)-ethyl]-3-naphthalen-1-yl-2-naphthalen-1-ylmethyl-propionamide Following the procedure of Example 23, but using the BOP reagent for coupling, and using 3-(1-imidazoyl)-propylamine, there was obtained 0.17 g of the product as a white foam. The structure was confirmed by NMR and mass spectroscopy; $(m+H)^+=585$.

EXAMPLE 29
(S)-N-[1-(2-Hydroxy-ethylcarbamoyl)-2-(1H-imidazol-4-yl)-ethyl]-3-naphthalen-1-yl-2-naphthalen-1-ylmethyl-propionamide Following the procedure of Example 23, but using the BOP reagent for coupling, and using 2-hydroxy-ethylamine, there was obtained 0.08 g of the product as a white foam. The structure was confirmed by NMR and mass spectroscopy; $(m+H)^+=521$.

EXAMPLE 30
(S)-N-[2-(1H-Imidazol-4-yl)-1-isopropylcarbamoyl-ethyl]-3-naphthalen-1-yl-2-naphthalen-1-ylmethyl-propionamide Following the procedure of Example 23, but using the BOP reagent for coupling, and using isopropylamine, there was obtained 0.22 g of the product as a white foam. The structure was confirmed by NMR and mass spectroscopy; $(m+H)^+=520$.

EXAMPLE 31
(S)-N-[2-(1H-Imidazol-4-yl)-1-(2-morpholin-4-yl-ethylcarbamoyl)-ethyl]-3-naphthalen-1-yl-2-naphthalen-1-ylmethyl-propionamide Following the procedure of Example 23, but using the PyBOP as the coupling reagent, and using (2-morpholin-4-yl)-ethylamine, there was obtained 0.26 g of the product as a white foam. The structure was confirmed by NMR and mass spectroscopy; $(m+E)^+=590$.

EXAMPLE 32
(S)-N-[1-(2-Diethylamino-ethylcarbamoyl)-2-(1H-imidazol-4-yl)-ethyl]-(3-naphthalen-1-yl-2-naphthalen-1-ylmethyl-propionamide Following the procedure of Example 23, but using the PyBOP as the coupling reagent, and using 2-diethylaminoethylamine, there was obtained 0.30 g of the product as a white foam. The structure was confirmed by NMR and mass spectroscopy; $(m+H)^+=576$.

EXAMPLE 33
(S)-N-[2-(1H-Imidazol-4-yl)-1-methylcarbamoyl-ethyl]-3-naphthalen-1-yl-2-naphthalen-1-ylmethyl-propionamide Following the procedure of Example 23, but using the PyBOP as the coupling reagent, and using methylamine, there was obtained 0.22 g of the product as a white foam. The structure was confirmed by NMR and mass spectroscopy; $(m+H)^+=491$.

EXAMPLE 34
(S)-N-[1-Ethylcarbamoyl-2-(1H-imidazol-4-yl)-ethyl]-3-naphthalen-1-yl-2-naphthalen-1-ylmethyl-propionamide Following the procedure of Example 23, but using the PyBOP as the coupling reagent, and using ethylamine, there was obtained 0.21 g of the product as a white foam. The structure was confirmed by NMR and mass spectroscopy; $(m+H)^+=505$.

EXAMPLE 35
(S)-N-{2-(1H-Imidazol-4-yl-1-[2-(4-sulfamoyl-phenyl)-ethylcarbamoyl]-ethyl}-3-naphthalen-1-yl-2-naphthalen-1-ylmethyl-propionamide Following the procedure of Example 23, but using the PyBOP as the coupling reagent, and using 2-(4-sulfamoylphenyl)-ethylamine, there was obtained 0.22 g of the product as a white foam. The structure was confirmed by NMR and mass spectroscopy; $(m+H)^+=660$.

EXAMPLE 36
(S)-2-[3-(Decahydro-naphthalen-1-yl)-2-(decahydro-naphthalen-1-ylmethyl)-propionylamino]-3-(1H-imidazol-4-yl)-propionic acid, methyl ester Step (a) Preparation of: Bis-(1-decahydro-naphthylmethyl)-acetic acid A solution of 1.0 g (2.9 mmol) of bis-(1-naphthylmethyl)-acetic acid in 100 mL acetic acid was reduced at 40° C., 54 pounds per square inch (psi) using 0.1 g of platinum oxide ($PtO_2$). The solvent was removed under reduced pressure, the residue taken up in $CH_2Cl_2$ and the solvent again removed leaving 1.0 g of the product as an oil.

Step (b) Preparation of: (S)-2-[3-(Decahydro-naphthalen-1-yl)-2-(decahydro-naphthalen-1-ylmethyl)-propionylamino]-3-(1H-imidazol-4-yl)-propionic acid, methyl ester A solution of 0.55 g (1.5 mmol) of bis-(1-decahydronaphthylmethyl)-acetic acid, 0.73 g (1.7 mmol) of His(Trt)-OCH$_3$•HCl, and 0.23 g (1.7 mmol) of HOBt in 30 mL THF was treated with 0.35 g (1.7 mmol) of DCC followed by 0.3 mL (1.7 mmol) of Et$_3$N and the mixture stirred at room temperature overnight. The mixture was filtered and the solvent removed under reduced pressure. The residue was taken up in EtOAc and washed with H$_2$O, a saturated solution of NaHCO$_3$, and a saturated solution of NaCl. Drying over MgSO$_4$ and removal of the solvent under reduced pressure gave the crude trityl derivative.

This was taken up in 12 mL of 85% acetic acid and heated at 90° for 2 hours. The solvent was removed under reduced pressure and the residue taken up in EtOAc, washed twice with a saturated solution of NaHCO$_3$, then with a saturated solution of NaCl. Drying over MgSO$_4$ and removal of the solvent under reduced pressure gave the crude product. Chromatography on silica gel, eluting with a gradient of EtOAc/hexane (10/90) to EtOAc/MeOH (96/4) gave 0.35 g of the product as a yellow foam. The structure was confirmed by NMR and mass spectroscopy; (m+H)$^+$=512.

EXAMPLE 37

(S)-3-(1H-Imidazol-4-yl)-2-[3-(5,6,7,8-tetrahydro-naphthalen-1-yl)-2-(5,6,7,8-tetrahydro-naphthalen-1-ylmethyl)-propionylamino]-propionic acid, methyl ester Step (a) Preparation of: Dimethyl bis-(5,6,7,8-tetrahydro-1-naphthylmethyl)-malonate To a suspension of 0.77 g (0.02 mol) of sodium hydride (NaH)•oil (60%) in 30 mL THF, cooled to 0° C. was added dropwise 1.06 g (8.0 mmol) of dimethyl malonate. After stirring for 15 minutes, the mixture was treated with 3.6 g (16 mmol) of 1-bromomethyl-5,6,7,8-tetrahydro-naphthalene (Chemical Abstracts, 75:76445 (1971)). After stirring at room temperature overnight, the mixture was diluted with EtOAc and washed with 1N HCl, then with a saturated solution of NaCl. Drying over MgSO$_4$ and removal of the solvent under reduced pressure gave 3.1 g of an oil which solidified on standing. The structure was confirmed by NMR spectroscopy.

Step (b) Preparation of Bis-(5,6,7,8-tetrahydro-1-naphthylmethyl)-acetic acid

A solution of 3.1 g (7.4 mmol) of dimethyl bis-(5,6,7,8-tetrahydro-1-naphthylmethyl)-malonate in 20 mL n-butanol was treated with a solution of 1.24 g (22 mmol) of potassium hydroxide (KOH) in 20 mL H$_2$O and the solution heated at reflux overnight. The solvent was removed under reduced pressure and the residue taken up in H$_2$O and acidified with dilute HCl to the Congo red color change. The mixture was extracted with EtOAc and the EtOAc washed with 1N HCl, and then a saturated solution of NaCl. Drying over MgSO$_4$ and removal of the solvent under reduced pressure gave 2.03 g of the product. A small amount recrystallized from EtOAc/hexane had mp 144–146° C. The structure was confirmed by NMR spectroscopy.

Step (c) (S)-3-(1H-Imidazol-4-yl)-2-[3-(5,6,7,8-tetrahydronaphthalen-1-yl)-2-(5,6,7,8-tetrahydro-naphthalen-1-ylmethyl)-propionylamino]-propionic acid, methyl ester Following the procedure of Example 36, Step (b), there was obtained 0.55 g of the product as a white foam. The structure was confirmed by NMR and mass spectroscopy; (m+H)$^+$=500.

EXAMPLE 38

(S)-N-[1-(2-Benzyloxy-ethylcarbamoyl)-2-(1H-imidazol-4-yl)-ethyl]-3-(5,6,7,8-tetrahydro-naphthalen-1-yl)-2-(5,6,7,8-tetrahydro-naphthalen-1-ylmethyl)-propionamide Following the procedure of Example 36, Step (b), but using PyBOP as the coupling agent, and using 2-benzyloxy-ethylamine, there was obtained 0.25 g of the product as a white foam. The structure was confirmed by NMR and mass spectroscopy; (m+H)$^+$=619.

EXAMPLE 39

(S)-2-(3-Benzo[b]thiophen-3-yl-2-benzo[b]thiophen-3-ylmethyl-propionylamino)-3-(1H-imidazol-4-yl)-propionic acid, methyl ester Step (a) Preparation of: Dimethyl bis-(benzo[b]thiophen-3-ylmethyl)-malonate A suspension of 0.34 g (8.5 mmol) of NaH•oil (60%) in 30 mL THF was treated with 0.45 g (3.4 mmol) of dimethyl malonate and stirred at room temperature for 15 minutes. The mixture was then treated with 1.55 g (6.8 mmol) of 3-bromomethyl-benzo[b]thiophene and the mixture then heated at reflux overnight. The solvent was removed under reduced pressure and the residue taken up in EtOAc and washed twice with 1N HCl, then with a saturated solution of NaCl. Drying over MgSO$_4$ and removal of the solvent under reduced pressure left 1.33 g of the product as an oil. The structure was confirmed by NMR spectroscopy.

Step (b) Preparation of: Bis-(benzo[b]thiophen-3-ylmethyl)-acetic acid

A solution of 1.3 g (3.3 mmol) of the material from Step (a) above in 10 mL n-butanol was treated with a solution of 0.52 g (9.3 mmol) of KOH in 10 mL H$_2$O and heated at reflux overnight. The solvent was removed under reduced pressure and the residue taken up in H$_2$O and acidified with dilute HCl. The mixture was extracted with EtOAc and washed with 1N HCl, and then a saturated solution of NaCl. Drying over MgSO$_4$ and removal of the solvent under reduced pressure left the crude product which was recrystallized from EtOAc/hexane to give 0.58 g of the product as a white solid. The structure was confirmed by NMR spectroscopy.

Step (c) Preparation of: (S)-2-(3-Benzo[b]-thiophen-3-yl-2-benzo[b]thiophen- 3-ylmethyl-propionylamino-3-(1H-imidazol-4-yl)-propionic acid, methyl ester Following the procedure of Example 36, Step (b), but using the BOP reagent as the coupling agent, and using bis-(benzo[b]thiophen-3-ylmethyl)-acetic acid, there was obtained 0.2 g of the product as a white foam. The structure was confirmed by NMR and mass spectroscopy; (m+H)$^+$=504.

EXAMPLE 40

(S)-3-(1H-Imidazol-4-yl)-2-(3-naphthalen-1-yl-2-naphthalen-1-ylmethyl-propionylamino)-thiopropionic acid, S-(2-acetylamino-ethyl)ester Following the procedure of Example 23, but using 2-acetylthioethylamine•HCl, there was obtained 0.82 g of the rearranged thio-ester as the product. The structure was confirmed by NMR and mass spectroscopy; (m+H)$^+$=579.

EXAMPLE 41

(S)-N-[1-(2-Cyano-ethylcarbamoyl)-2-(1H-imidazol-4-yl)-ethyl]-3-naphthalen-1-yl-2-naphthalen-1-ylmethyl-propionamide Following the procedure of Example 23, but using PyBOP as the coupling agent, and using 2-cyanoethylamine, there was obtained 0.2 g of the product as a white foam. The structure was confirmed by NMR and mass spectroscopy; (m+H)$^+$=530.

EXAMPLE 42

(S)-3-(1H-Imidazol-4-yl)-2-(3-naphthalen-1-yl-2-naphthalen-1-ylmethyl-propionylamino)-propionic acid, 2-hydroxy-ethyl ester, trifluoroacetate salt Following the procedure of Example 23, but using PyBOP as the coupling agent, and using ethylene glycol, there was obtained 0.13 g of the crude product. Purification by preparative HPLC gave 80 mg of the pure product as the

EXAMPLE 43
(S)-N-[1-Dimethylcarbamoyl-2-(1H-imidazol-4-yl)-ethyl]-3-naphthalen-1-yl-2-naphthalen-1-ylmethyl-propionamide Following the procedure of Example 23, but using PyBOP as the coupling agent, and using dimethylamine, there was obtained 75 mg of the product. The structure was confirmed by NMR and mass spectroscopy; $(m+H)^+=505$.

EXAMPLE 44
(S)-3-(1H-Imidazol-4-yl)-2-(3-naphthalen-1-yl-2-naphthalen-1-ylmethyl-propionylamino)-propionic acid, but-3-ynyl ester, trifluoroacetate salt Following the procedure of Example 23, but using PyBOP as the coupling agent, and using 3-butyn-1-ol, there was obtained 0.32 g of the crude product. Purification by preparative HPLC gave 30 mg of the pure product as the trifluoroacetate salt. The structure was confirmed by NMR and mass spectroscopy; $(m+H)^+=530$.

EXAMPLE 45
(S)-2-[3-(Decahydro-naphthalen-1-yl)-2-(decahydro-naphthalen-1-ylmethyl)-propionylamino]-3-(1H-imidazol-4-yl)-propionic acid, 2-cyano-ethyl ester Following the procedure of Example 23, Step (b), but using PyBOP as the coupling agent, and using 2-cyanoethanol, there was obtained 70 mg of the product as a white foam. The structure was confirmed by NMR and mass spectroscopy; $(m+H)^+=552$.

EXAMPLE 46
(S)-N-[2-(1H-Imidazol-4-yl)-1-propylcarbamoyl-ethyl]-3-naphthalen-1-yl)-2-naphthalen-1-ylmethyl)-propionamide Following the procedure of Example 23, but using PyBOP as the coupling agent, and using n-propylamine, there was obtained 50 mg of the product. The structure was confirmed by NMR and mass spectroscopy; $(m+H)^+=519$.

EXAMPLE 47
(S)-3-[1H-Imidazol-4-yl)-2-(3-naphthalen-1-yl-2-naphthalen-1-ylmethyl-propionylamino)-propionic acid, 2-imidazol-1-yl-ethyl ester Following the procedure of Example 23, but using BOP reagent as the coupling agent, and using 2-(1-imidazol)-ethanol, there was obtained 70 mg of the product as a white foam. The structure was confirmed by NMR and mass spectroscopy; $(m+H)^+=572$.

EXAMPLE 48
(S)-3-(1H-Imidazol-4-yl)-2-(3-naphthalen-1-yl-2-naphthalen-1-ylmethyl-propionylamino)-propionic acid, but-3-enyl ester Following the procedure from Example 23, but using the BOP reagent as the coupling agent, and using 3-buten-1-ol, there was obtained 160 mg of the product as a white foam. The structure was confirmed by NMR and mass spectroscopy; $(m+H)^+=532$.

EXAMPLE 49
(S)-3-(1H-Imidazol-4-yl)-2-[3-(5,6,7,8-tetrahydro-naphthalen-1-yl)-2-(5,6,7,8-tetrahydro-naphthalen-1-ylmethyl)-propionylamino]-propionic acid, 2-cyano-ethyl ester Following the procedure of Example 37, Step (c), but using the BOP reagent as the coupling agent, and using 2-cyanoethanol, there was obtained 110 mg of the product as a white foam. The structure was confirmed by NMR and mass spectroscopy; $(m+H)^+=539$.

EXAMPLE 50
(S)-N-[2-(1H-Imidazol-4-yl)-1-phenethylcarbamoyl-ethyl]-3-naphthalen-1-yl-2-naphthalen-1-ylmethyl)-propionamide Following the procedure of Example 23, but using PyBOP as the coupling agent, and using phenethylamine, there was obtained 61 mg of the product. The structure was confirmed by NMR and mass spectroscopy; $(m+H)^+=581$.

EXAMPLE 51
(S)-3-(1H-Imidazol-4-yl-2-[methyl-(3-naphthalen-1-yl-2-naphthalen-1-ylmethyl-propionyl)-amino]-propionic acid, methyl ester, trifluoroacetate A suspension of 0.56 g (2.2 mmol) of N-MeHIS-OMe•2 HCl in 15 mL dimethylacetamide (DMA) was treated with 0.8 mL (6.6 mmol) of N-methylpiperidine followed by a solution of 0.79 g (2.2 mmol) of bis-(1-naphthylmethyl)-acetyl chloride in 5 mL $CH_2Cl_2$, and the mixture was stirred at room temperature for 2 days. The mixture was diluted with EtOAc and washed three times with $H_2O$, a saturated solution of $NaHCO_3$, and then a saturated solution of NaCl. Drying over $MgSO_4$, and removal of the solvent under reduced pressure left the crude product. Chromatography on silica gel, eluting with $CH_2Cl_2$/MeOH (99/1) gave 0.4 g of the partly purified product. Preparative HPLC gave 42 mg of the pure product as the trifluoroacetate salt. The structure was confirmed by mass spectroscopy; $(m+H)^+=506$.

EXAMPLE 52
(S)-N-[1-Hydroxymethyl-2-(1H-imidazol-4-yl)-ethyl]-3-naphthalen-1-yl-2-naphthalen-1-ylmethyl-propionamide A solution of 0.5 g (1.0 mmol) of the product from Example 1 in 15 mL of THF was cooled in ice and treated with 88 mg (4.0 mmol) of lithium borohydride. After 15 minutes at 0° C., the mixture was allowed to warm to room temperature over 1 hour. The mixture was acidified with 5 mL of 2N HCl, then made basic with a saturated solution of $NaHCO_3$, and extracted with EtOAc. The EtOAc solution was washed with a saturated solution of NaCl, dried over $MgSO_4$, and the solvent removed under reduced pressure giving the crude product. Chromatography on silica gel, eluting with $CHCl_3$/MeOH (95/5) gave 310 mg of the product as a white foam. The structure was confirmed by NMR and mass spectroscopy; $(m+H)^+=464$.

EXAMPLE 53
(S)-3-(1H-Imidazol-4-yl)-2-(3-naphthalen-1-yl-2-naphthalen-1-ylmethyl-propionylamino)-propionic acid, phenethyl ester This compound was prepared following the procedure of Example 45. The structure was confirmed by NMR and mass spectroscopy; $(m+H)^+=582$.

EXAMPLE 54
(S)-3-(1H-Imidazol-4-yl)-2-(3-naphthalen-1-yl-2-naphthalen-1-ylmethyl-propionyiamino)-propionic acid, 3-cyano-propyl ester This compound was prepared following the procedure of Example 45. The structure was confirmed by NNR and mass spectroscopy; $(m+H)^+=545$.

EXAMPLE 55
(S)-3-(1H-Imidazol-4-yl)-2-(3-naphthalen-1-yl-2-naphthalen-1-ylmethyl-propionylamino)-propionic acid 3-methyl-but-2-enyl ester This compound was prepared following the procedure of Example 47. The structure was confirmed by NMR and mass spectroscopy; $(m+H)^+=546$.

EXAMPLE 56

(S)-3-(1H-Imidazol-4-yl)-2-(3-naphthalen-1-yl-2-naphthalen-1-ylmethyl-propylamino)-propionic acid methyl ester Step (a) Preparation of Bis-(1-naphthylmethyl)-acetic acid, O,N-dimethylamide To a solution of 5.0 g (13.9 mmol) of bis-(1-naphthylmethyl)acetyl chloride in 30 mL $CH_2Cl_2$ cooled in ice was added a solution of 1.36 g (13.9 mmol) of O,N-dimethylhydroxylamine•HCl and 1.7 mL (13.9 mmol) of N-methylpiperidine in 25 mL $CH_2Cl_2$. This was followed with an additional 1.7 mL (13.9 mmol) of N-methylpiperidine. The cooling was removed and the mixture allowed to stir at room temperature overnight. The solvent was removed under reduced pressure and the residue taken up in EtOAc and washed with 1N HCl, $H_2O$, a saturated solution of $NaHCO_3$, and a saturated solution of NaCl. Drying over $MgSO_4$ and removal of the solvent under reduced pressure left the crude product. Chromatography over silica gel, and eluting with $CHCl_3$ gave 3.48 g of the product as an oil which crystallized, mp 101–103° C. The structure was confirmed by NMR and mass spectroscopy; $(m+H)^+=384$.

Step (b) Preparation of Bis-(1-naphthylmethyl)-acetaldehyde

A solution of 3.48 g (9.1 mmol) of bis-(1-naphthylmethyl)-acetic acid, O,N-dimethylamide in 50 mL of tetrahydrofuran was cooled in ice and treated rapidly in portions with 0.45 g (11.8 mmol) of lithium aluminum hydride. After stirring at 0° C. for 45 minutes, the mixture was decomposed with a solution of $KHSO_4$ in $H_2O$. The mixture was diluted with EtOAc, the pH adjusted to 4, an the layers separated. The EtOAc layer was washed with 1N HCl, $H_2O$, a saturated solution of $NaHCO_3$, and a saturated solution of NaCl. Drying over $MgSO_4$ and removal of the solvent under reduced pressure left 2.35 g of the product as an oil which crystallized. The structure was confirmed by NMR and mass spectroscopy; $(m+H)^+=324$.

Step (c) Preparation of (S)-3-(1H-Imidazol-4-yl)-2-(3-naphthalen-1-yl-2-naphthalen-1-ylmethyl-propylamino)-propionic acid, methyl ester A solution of 3.41 g (10.5 mmol) of bis-(1-naphthylmethyl)-acetaldehyde in 60 mL of tetrahydrofuran was treated with 4.32 g (10.5 mmol) of HIS(Trt)-OMe and 14 g of activated 3A molecular sieves and stirred at room temperature overnight. A pinch of bromocresol green was added, and the color adjusted to a light green with 1N HCl in dioxane, and the mixture then treated with 1.2 g (18 mmol) of sodium cyanoborohydride. After stirring at room temperature overnight, the mixture was filtered and the sieves washed with tetrahydrofuran. The organic phase was diluted with EtOAc and washed with a saturated solution of $NaHCO_3$, $H_2O$, and a saturated solution of NaCl. Drying over $MgSO_4$ and removal of the solvent under reduced pressure left 7.27 g of the crude product as a cream foam. This was the trityl compound complexed with $BH_2CN$.

A solution of 1.31 g (1.7 mmol) of this complex in 80 mL of 88% formic acid was heated at 89° C. for 0.5 hour. The solvent was removed under reduced pressure and the residue taken up in EtOAc and washed twice with a saturated solution of $NaHCO_3$, then with a saturated solution of NaCl. Drying over $MgSO_4$ and removal of the solvent under reduced pressure left the crude product. Chromatography on silica gel, and eluting with $CHCl_3$/MeOH (95/5) gave 480 mg of the pure product as a white foam. The structure was confirmed by NMR and mass spectroscopy; $(m+H)^+=478$.

EXAMPLE 57

(S)-3-(1H-Imidazol-4-yl)-2-(3-naphthalen-1-yl-2-naphthalen-1-ylmethyl-propionylamino)-propionic acid, methoxycarbonylmethyl ester This compound was prepared following the procedure of Example 47. The structure was confirmed by NMR and mass spectroscopy; $(m+H)^+=550$.

EXAMPLE 58

(S )-3-(1H-Imidazol-4-yl)-2-(3-naphthalen-1-yl-2-naphthalen-1-ylmethyl-propionylamino)-propionic acid, cyanomethyl ester This compound was prepared following the procedure of Example 47. The structure was confirmed by NMR and mass spectroscopy; $(m+H)^+=517$.

EXAMPLE 59

(S)-3-(1H-Imidazol-4-yl)-2-(3-naphthalen-1-yl-2-naphthalen-1-ylmethyl-propionylamino)-propionic acid, 2-(2-hydroxy-ethyldisulfanyl)-ethyl ester This compound was prepared following the procedure of Example 47. The structure was confirmed by NMR and mass spectroscopy; $(m+H)^+=614$.

EXAMPLE 60

(S)-3-(3-Methoxymethyl-3H-imidazol-4-yl)-2-(3-naphthalen-1-yl-2-naphthalen-1-ylmethyl-propionylamino)-propionic acid, methyl ester A solution of 0.8 g (1.1 mmol) of bis-(1-naphthylmethyl)-acetyl-HIS(Trt)-$OCH_3$ in 15 mL $CH_2Cl_2$ was treated with 0.2 mL (2.4 mmol) of chloromethylmethyl ether and allowed to stir at room temperature for 3 days. The mixture was diluted with 80 mL of 80% acetic acid and heated at 89° C. for 0.5 hour. The solvent was removed under reduced pressure and the residue taken up in EtOAc, and washed twice with a saturated solution of $NaHCO_3$, then with a saturated solution of NaCl. Drying over $MgSO_4$ and removal of the solvent under reduced pressure left the crude product. Chromatography on silica gel, and eluting with $CHCl_3$/MeOH (97/3) gave 0.17 g of the pure product as a solid, mp 182–185° C. The structure was confirmed by NMR and mass spectroscopy; $(m+H)^+=536$.

EXAMPLE 61

(S)-3-(1H-Imidazol-4-yl)-2-(3-naphthalen-1-yl-2-naphthalen-1-ylmethyl-propionylamino)-propionic acid, (±)-1-cyano-ethyl ester This compound was prepared following the procedure of Example 47. The structure was confirmed by NMR and mass spectroscopy; $(m+H)^+=531$.

EXAMPLE 62

(S)-3-(1H-Imidazol-4-yl)-2-(3-naphthalen-1-yl-2-naphthalen-1-ylmethyl-propylamino)-propan-1-ol A solution of 1.0 g (1.3 mmol) of the complex from Example 56, Step (c), in 20 mL of tetrahydrofuran was cooled in ice and treated with 144 mg (6.6 mmol) of lithium borohydride. The cooling was removed and the mixture allowed to stir at room temperature for 1.75 hours. The mixture was decomposed with 2N HCl, then made basic with a saturated solution of $NaHCO_3$, and extracted with EtOAc. The EtOAc was washed with a saturated solution of $NaHCO_3$, then with a saturated solution of NaCl. Drying over $MgSO_4$ and removal of the solvent under reduced pressure left 0.95 g of the reduced complex.

This was taken up in 60 mL of 88% formic acid and heated at 89° C. for 0.5 hour. The solvent was removed under reduced pressure and the residue taken up in 30 mL MeOH and treated with a solution of 2 g NaOH in 10 mL $H_2O$. After stirring at room temperature overnight, the solution was treated with 22 mL of 2N HCl and stripped to dryness under reduced pressure. The residue was taken up in EtOAc and washed with a saturated solution of NaHCO₃, then a saturated solution of NaCl. Drying over MgSO₄ and removal of the solvent under reduced pressure left the crude product. Chromatography on silica gel, and eluting with CHCl₃/MeOH (90/10) gave 0.15 g of the pure product as a cream foam. The structure was confirmed by NMR and mass spectroscopy; (m+H)⁺=450.

EXAMPLE 63

(S)-3-(1H-Imidazol-4-yl)-N-methyl-2-(3-naphthalen-1-yl-2-naphthalen-1-ylmethyl-propylamino)-propionamide A solution of 1.4 g (1.8 mmol) of the complex from Example 56, Step (c), in 15 mL MeOH and 15 mL of tetrahydrofuran was cooled in ice and saturated with methylamine gas and allowed to stir at room temperature for 2 days. The solvent was removed under reduced pressure leaving a brown foam.

This was taken up in 80 mL of 88% formic acid and heated at 89° C. for 0.5 hour. The solvent was removed under reduced pressure and the residue taken up in EtOAc and washed twice with a saturated solution of NaHCO₃, then with a saturated solution of NaCl. Drying over MgSO₄ and removal of the solvent under reduced pressure left the crude product. Chromatography on silica gel, and eluting with CHCl₃/MeOH (95/5) gave 0.59 g of the product as a white foam. The structure was confirmed by NMR and mass spectroscopy; (m+H)⁺=477.

EXAMPLE 64

(S)-N-[1-Methylcarbamoyl-2-(3-methyl-3H-imidazol-4-yl)-ethyl]-3-naphthalen-1-yl-2-naphthalen-1-ylmethyl-propionamide A solution of 611 mg (1.2 mmol) of the product from Example 6 in 20 mL MeOH and 10 mL tetrahydrofuran was cooled in ice and saturated with gaseous methylamine. The cooling was removed and the solution allowed to stir at room temperature overnight. The solvent was removed under reduced pressure and the residue triturated with acetonitrile to give 529 mg of the pure product, mp 250–252° C. The structure was confirmed by NMR and mass spectroscopy; (m+H)⁺=505.

EXAMPLE 65

(S)-2-(2-Benzyl-3-naphthalen-1-yl-propionylamino)-3-(1H-imidazol-4-yl)-propionic acid, methyl ester Following the procedure of Example 7, Steps (a)–(d), but using benzyl-(α-naphthylmethyl)-acetic acid (*Ann.*, 468:300 (1929)), the product is obtained after preparative HPLC as a white foam. The structure was confirmed by NMR and mass spectroscopy; (m+H)⁺=442.

We claim:

1. A compound of Formula I

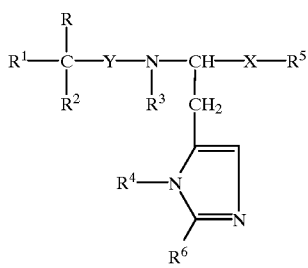

wherein R is hydrogen or alkyl; $R^1$ and $R^2$ are the same or different and are selected from the group consisting of:

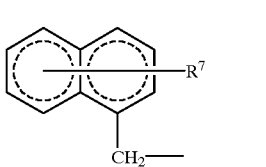

wherein the bicyclic ring is either aromatic, or partially or completely saturated, and $R^7$ is 1 to 3 substituents selected from the group consisting of:

hydrogen,
alkyl,
alkenyl,
alkoxy,
thioalkoxy,
hydroxy,
mercapto,
halogen,
nitro,

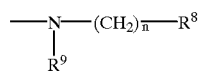

wherein $R^8$ and $R^9$ are the same or different and are selected from the group consisting of:
hydrogen,
alkyl, or $R^8$ and $R^9$ are taken together with N to form a 5- or 6-membered ring which does or does not contain a heteroatom selected from the group consisting of: S, O, and N—$R^{10}$ wherein $R^{10}$ is hydrogen or alkyl, and
n is zero or an integer of one to four,

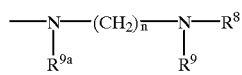

wherein $R^{9a}$ is hydrogen or alkyl, and $R^8$, $R^9$, and n are as defined above, and

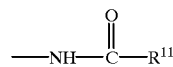

wherein $R^{11}$ is selected from the group consisting of:
hydrogen,
alkyl, and
aryl,

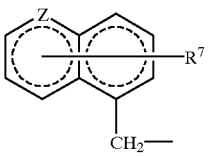

wherein the bicyclic ring is either aromatic, or partially or completely saturated, and Z is selected from the group consisting of:

$NR^{12}$ wherein $R^{12}$ is hydrogen, alkyl or

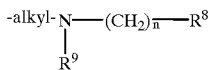

wherein $R^8$, $R^9$, and n are as defined above, or $R^{12}$ is absent,
O,
S,
SO, and
$SO_2$, and
Z is at other positions in the bicyclic ring system provided that when the bicyclic ring is aromatic, Z is not at the point of attachment of the $CH_2$ unit and $R^{12}$ is absent, and $R^7$ is as defined above,

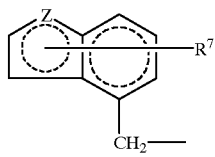

wherein the bicyclic ring is either aromatic, or partially or completely saturated, and Z and $R^7$ are as defined above, and $R^{12}$ is present

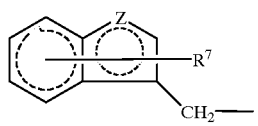

wherein the bicyclic ring is either aromatic, or partially or completely saturated, and Z and $R^7$ are as defined above, and $R^{12}$ is present,

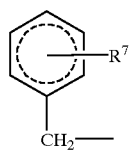

wherein the monocyclic ring is either aromatic, or partially or completely saturated, and $R^7$ is as defined above with the proviso that $R^1$ and $R^2$ are not both a monocyclic ring, and

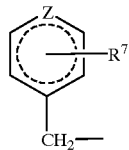

wherein the monocyclic ring is either aromatic, or partially or completely saturated, and $R^7$ and Z are as defined above with the proviso that $R^1$ and $R^2$ are not both a monocyclic ring;
$R^3$ is hydrogen or alkyl;
$R^4$ is selected from the group consisting of:
hydrogen,
alkyl,
alkenyl,
alkynyl,
benzyl,
alkyl chain wherein the alkyl chain is interrupted by a heteroatom selected from the group consisting of: S, O, and $N—R^{10}$ wherein $R^{10}$ is as defined above,

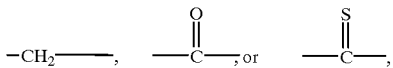

wherein p is an integer of one to four, and $R^{13}$ is alkyl or benzyl, and

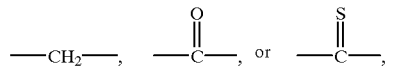

wherein p and $R^{13}$ are as defined above;
X is

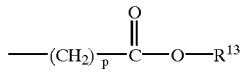

Y is

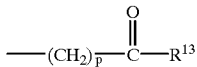

$R^5$ is selected from the group consisting of:
—$OR^{14}$ wherein $R^{14}$ is selected from the group consisting of:
hydrogen,
alkyl,
alkenyl,
alkynyl,
cycloalkyl,
cycloalkylalkyl,
haloalkyl,
hydroxyalkyl,
mercaptoalkyl,
cyanoalkyl,
nitroalkyl,
alkoxyalkyl,
arylalkyl,
heteroarylalkyl,
benzyloxyalkyl,
thioalkoxyalkyl,
acetamidoalkyl,
$HOCH_2CH_2—S—S—CH_2CH_2—$,

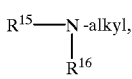

wherein $R^{15}$ and $R^{16}$ are the same or different and are selected from the group consisting of:
hydrogen,
alkyl or $R^{15}$ and $R^{16}$ are taken together with N to form a 5- or 6-membered ring which does or does not contain a heteroatom selected from the group consisting of: S, O, and $N—R^{10}$ wherein $R^{10}$ is as defined above, HO$_2$C-alkyl,
alkyl-O$_2$C-alkyl, and

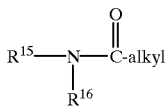

wherein R$^{15}$ and R$^{16}$ are as defined above,
—S—R$^{14}$ wherein R$^{14}$ is as defined above with the proviso that R$^{14}$ is not hydrogen,

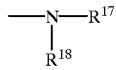

wherein R$^{17}$ and R$^{18}$ are the same or different and are selected from the group consisting of:
hydrogen,
alkyl,
alkenyl,
cyanoalkyl,
hydroxyalkyl,
alkoxyalkyl,
arylalkyl,
heteroarylalkyl,
benzyloxyalkyl,
cycloalkyl,
cycloalkylalkyl,
haloalkyl,
mercaptoalkyl,
nitroalkyl,
thioalkoxyalkyl,
acetamidoalkyl,

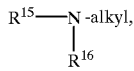

wherein R$^{15}$ and R$^{16}$ are the same or different and are selected from the group consisting of:
hydrogen,
alkyl or R$^{15}$ and R$^{16}$ are taken together with N to form a 5- or 6-membered ring which does or does not contain a heteroatom selected from the group consisting of: S, O, and N—R$^{10}$ wherein R$^{10}$ is as defined above,
or R$^{17}$ and R$^{18}$ are taken together with N to form a 5- or 6-membered ring which does or does not contain a heteroatom selected from the group consisting of: S, O, and N—R$^{10}$ wherein R$^{10}$ is as defined above,
—NH—OR$^{10}$ wherein R$^{10}$ is as defined above,
alkyl,
alkenyl, and
arylalkyl; and
R$^6$ is hydrogen,
—SR where R is as defined above,
—OR where R is as defined above, or

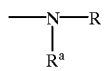

wherein R and R$^a$ are the same or different and are as defined above for R;

and when X is —CH$_2$— and R$^{17}$ is hydrogen or alkyl then R$^{18}$ may be

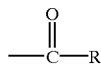

wherein R is as defined above, or

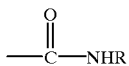

wherein R is as defined above; and when X is

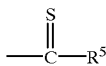

must be

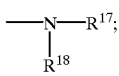

and
excluding the compound wherein
R is hydrogen,
R$^1$ and R$^2$ are each

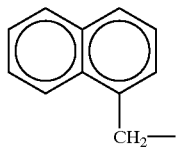

R$^3$ is hydrogen,
R$^4$ is hydrogen,
X is

Y is

R$^5$ is OR$^{14}$ wherein R$^{14}$ is hydrogen, and
R$^6$ is hydrogen;
or corresponding isomers thereof,
or a pharmaceutically acceptable salt thereof.
2. A compound according to claim 1 wherein
R is hydrogen;
R$^7$ is selected from the group consisting of:
hydrogen,
methoxy,
thiomethoxy,
hydroxy, halogen, and

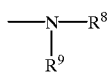

wherein $R^8$ and $R^9$ are the same or different and are selected from the group consisting of:
hydrogen, and
alkyl;

$R^3$ is hydrogen or methyl;

$R^4$ is selected from the group consisting of:
hydrogen,
methyl,
ethyl, and
—$CH_2$—O—$CH_3$;

X is

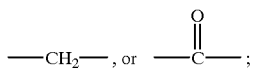

Y is

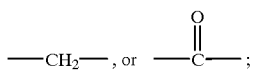

$R^5$ is selected from the group consisting of:
—O—$R^{14}$ wherein $R^{14}$ is selected from the group consisting of:
hydrogen,
alkyl,
alkenyl,
alkynyl,
cycloalkyl,
cycloalkylalkyl,
hydroxyallyl,
mercaptoalkyl,
cyanoalkyl,
alkoxyalkyl,
arylalkyl,
heteroarylalkyl,
benzyloxyalkyl,
thioalkoxyalkyl,
acetamidoalkyl,
$HOCH_2CH_2$—S—S—$CH_2CH_2$—,

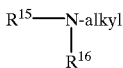

wherein $R^{15}$ and $R^{16}$ are the same or different and are selected from the group consisting of:
hydrogen,
alkyl or $R^{15}$ and $R^{16}$ are taken together with N to form a 5- or 6-membered ring which does or does not contain a heteroatom selected from the group consisting of: O, and $NR^{10}$ wherein $R^{10}$ is hydrogen or methyl, and
alkyl-$O_2C$-alkyl,
—S—$R^{14}$ wherein $R^{14}$ is as defined above with the proviso that $R^{14}$ is not hydrogen, and

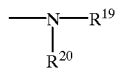

wherein $R^{19}$ is
hydrogen,
alkyl,
alkenyl,
alkynyl,
cycloalkyl,
cycloalkylalkyl,
cyanoalkyl,
hydroxyalkyl,
alkoxyalkyl,
arylalkyl,
heteroarylalkyl,
benzyloxyalkyl,
mercaptoalkyl,
thioalkoxyalkyl,
acetamidoalkyl,

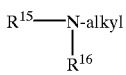

wherein $R^{15}$ and $R^{16}$ are the same or different and are selected from the group consisting of:
hydrogen,
alkyl or $R^{15}$ and $R^{16}$ are taken together with N to form a 5- or 6-membered ring which does or does not contain a heteroatom selected from the group consisting of: S, O, and N—$R^{10}$ wherein $R^{10}$ is as defined above, and
$R^{20}$ is hydrogen or methyl; and $R^6$ is hydrogen.

3. A compound according to claim 2 wherein $R^1$ and $R^2$ are the same or different and are selected from the group consisting of:

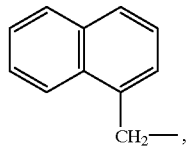

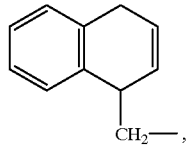

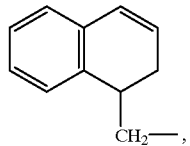

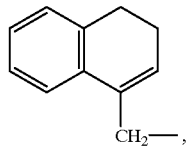

-continued
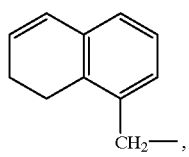
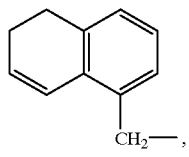
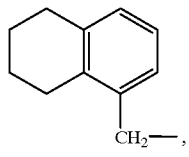
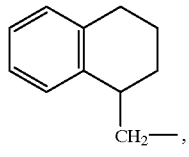
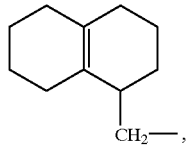
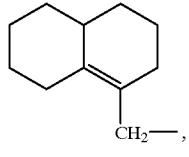
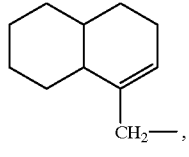
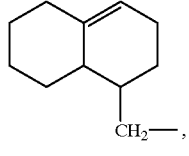
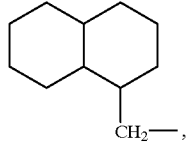
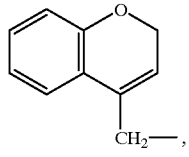
-continued
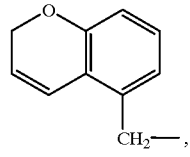
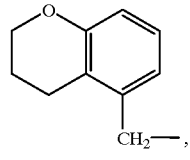
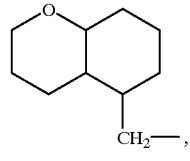
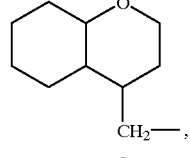
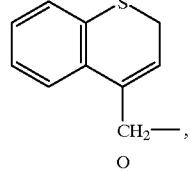
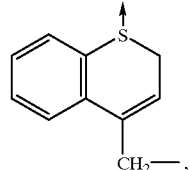
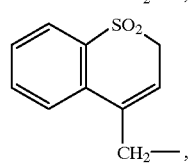
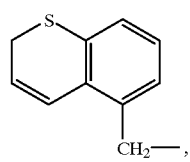
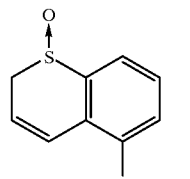
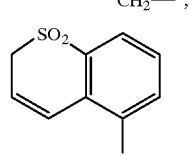

-continued
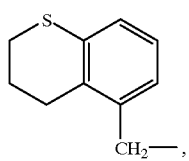
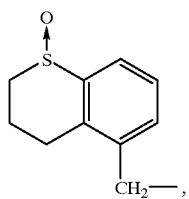
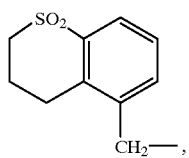
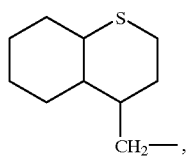
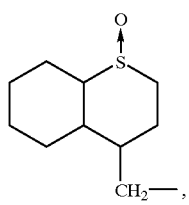
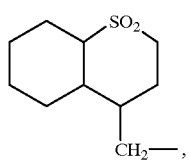
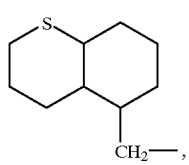
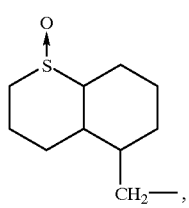
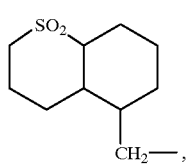
-continued
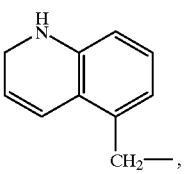
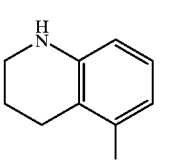
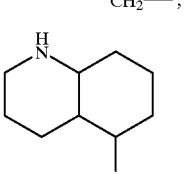
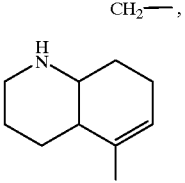
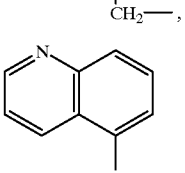
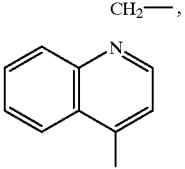
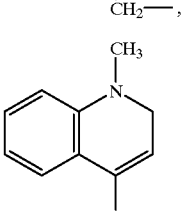
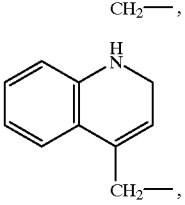
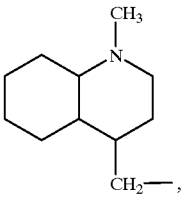

-continued
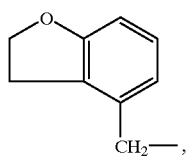
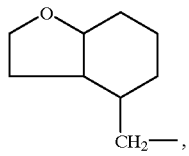
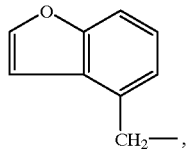
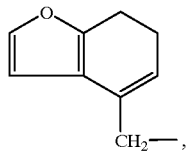
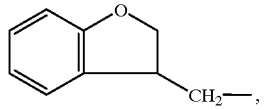
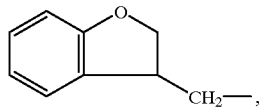
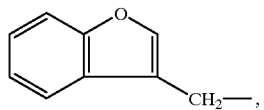
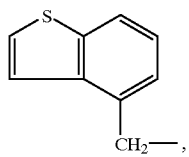
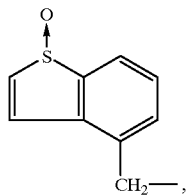
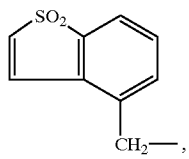
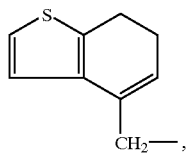
-continued
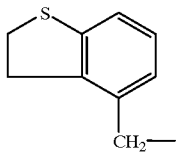
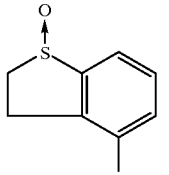
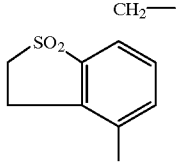
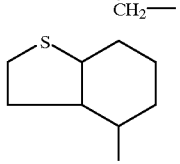
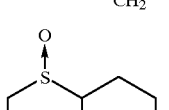
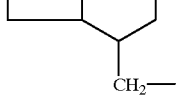
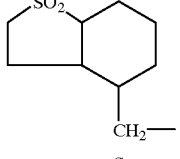
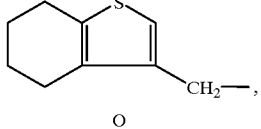
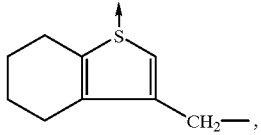
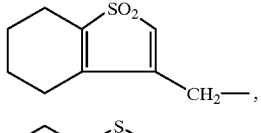
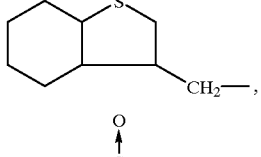
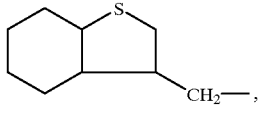

-continued
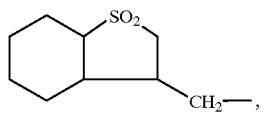
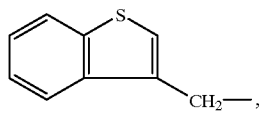
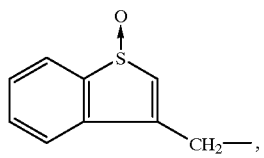
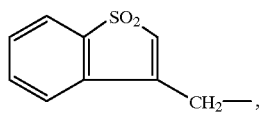
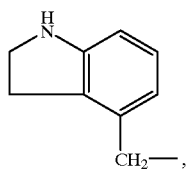
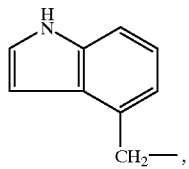
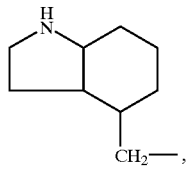
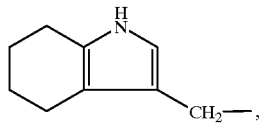
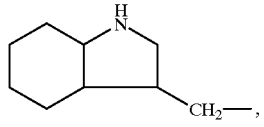
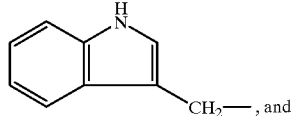
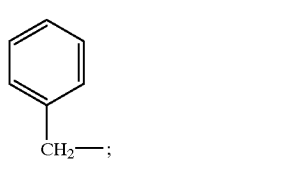
$R^3$ is hydrogen or methyl;
$R^4$ is hydrogen, methyl, or —CH$_2$OCH$_3$;
X is —CH$_2$— or
Y is —CH$_2$—, or
—CH$_2$—, or  ;
and
$R^5$ is selected from the group consisting of:
—O—R$^{14}$ wherein R$^{14}$ is selected from the group consisting of:
hydrogen,
alkyl,
alkenyl,
alkynyl,
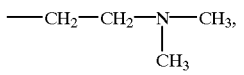
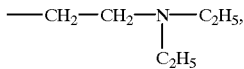
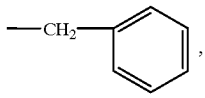
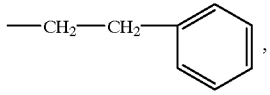
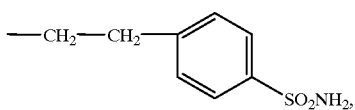
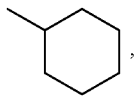
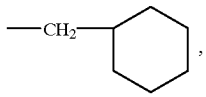
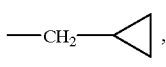
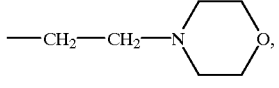
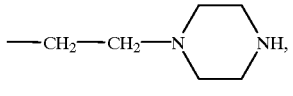
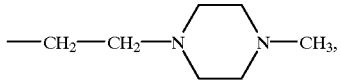

-continued
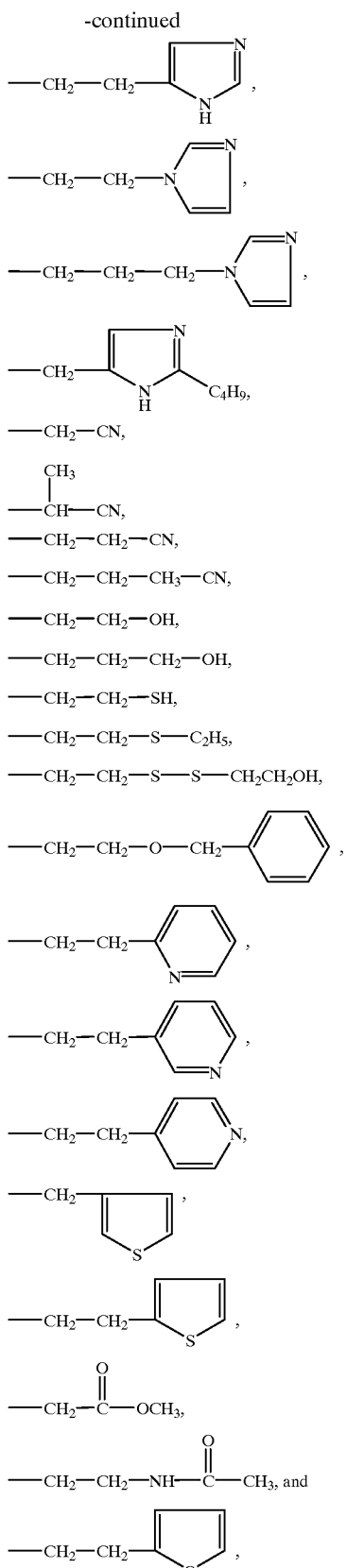
—SR$^{14}$ wherein R$^{14}$ is as defined above with the proviso that R$^{14}$ is not hydrogen, and
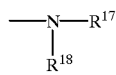
wherein R$^{17}$ is selected from the group consisting of:
hydrogen,
alkyl,
alkenyl,
alkynyl,
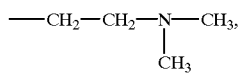
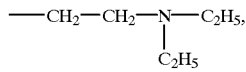
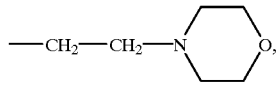
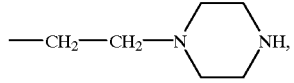
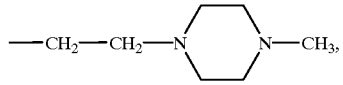
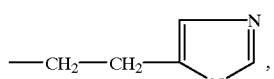
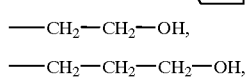
—CH$_2$—CH$_2$—OH,
—CH$_2$—CH$_2$—CH$_2$—OH,
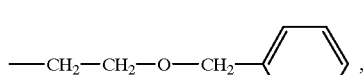
—CH$_2$—CH$_2$—S—C$_2$H$_5$,
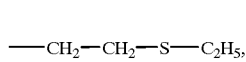
—CH$_2$—CH$_2$—CN,
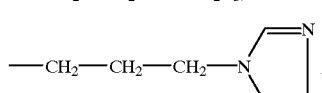
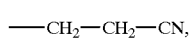
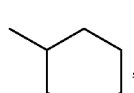
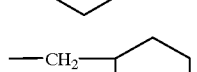
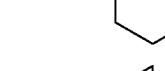
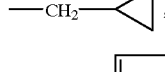
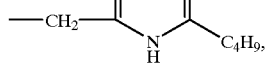

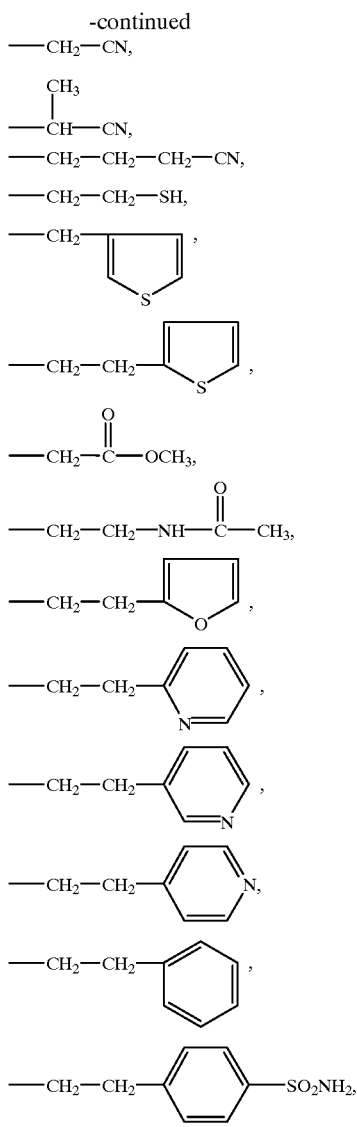

$R^{18}$ is hydrogen or methyl, and
—NH—OR$^{10}$ wherein R$^{10}$ is hydrogen or methyl.

4. A compound according to claim 3 selected from the group consisting of:

(S)-3-(1H-Imidazol-4-yl)-2-(3-naphthalen-1-yl-2-naphthalen-1-ylmethyl-propionylamino)-propionic acid, methyl ester;

(R)-3-(1H-Imidazol-4-yl)-2-(3-naphthalen-1-yl-2-naphthalen-1-ylmethyl-propionylamino)-propionic acid, methyl ester;

(S)-3-(1R-Imidazol-4-yl)-2-(3-naphthalen-1-yl-2-naphthalen-1-ylmethyl-propionylamino)-propionic acid;

(R)-3-(1H-Imidazol-4-yl)-2-(3-naphthalen-1-yl-2-naphthalen-1-ylmethyl-propionylamino)-propionic acid;

(S)-3-(1H-Imidazol-4-yl)-2-(3-naphthalen-1-yl-2-naphthalen-1-ylmethyl-propionylamino)-propionic acid, ethyl ester;

(S)-3-(3-Methyl-3H-imidazol-4-yl)-2-(3-naphthalen-1-yl-2-naphthalen-1-ylmethyl-propionylamino)-propionic acid, methyl ester;

(S)-3-(1H-Imidazol-4-yl)-2-(3-naphthalen-1-yl-2-naphthalen-1-ylmethyl-propionylamino)-propionic acid, propyl ester;

(S)-3-(1H-Imidazol-4-yl)-2-(3-naphthalen-1-yl-2-naphthalen-1-ylmethyl-propionylamino)-propionic acid, isopropyl ester;

(S)-3-(1H-Imidazol-4-yl)-2-(3-naphthalen-1-yl-2-naphthalen-1-ylmethyl-propionylamino)-propionic acid, butyl ester;

(S)-3-(1H-Imidazol-4-yl)-2-(3-naphthalen-1-yl-2-naphthalen-1-ylmethyl-propionylamino)-propionic acid, benzyl ester;

(S)-3-(1H-Imidazol-4-yl)-2-(3-naphthalen-1-yl-2-naphthalen-1-ylmethyl-propionylamino)-propionic acid, cyclohexyl ester;

(S)-3-(1H-Imidazol-4-yl)-2-(3-naphthalen-1-yl-2-naphthalen-1-ylmethyl-propionylamino)-propionic acid, cyclopropylmethyl ester;

(S)-3-(1H-Imidazol-4-yl)-2-(3-naphthalen-1-yl-2-naphthalen-1-ylmethyl-propionylamino)-propionic acid, 2-butyl-1H-imidazol-4-ylmethyl ester;

(S)-3-(1H-Imidazol-4-yl)-2-(3-naphthalen-1-yl-2-naphthalen-1-ylmethyl-propionylamino)-propionic acid, (±)-sec-butyl ester;

(S)-3-(1H-Imidazol-4-yl)-2-(3-naphthalen-1-yl-2-naphthalen-1-ylmethyl-propionylamino)-propionic acid, allyl ester;

(S)-3-(1H-Imidazol-4-yl)-2-(3-naphthalen-1-yl-2-naphthalen-1-ylmethyl-propionylamino)-propionic acid, prop-2-ynyl ester;

(S)-3-(1H-Imidazol-4-yl)-2-(3-naphthalen-1-yl-2-naphthalen-1-ylmethyl-propionylamino)-propionic acid, 2-cyano-ethyl ester;

(S)-3-(1H-Imidazol-4-yl)-2-(3-naphthalen-1-yl-2-naphthalen-1-ylmethyl-propionylamino)-propionic acid, 2-benzyloxy-ethyl ester;

(S)-3-(1H-Imidazol-4-yl)-2-(3-naphthalen-1-yl-2-naphthalen-1-ylmethyl-propionylamino)-propionic acid, 2-thiophen-2-yl-ethyl ester;

(S)-3-(1H-Imidazol-4-yl)-2-(3-naphthalen-1-yl-2-naphthalen-1-ylmethyl-propionylamino)-propionic acid, thiophen-3-ylmethyl ester;

(S)-3-(1H-Imidazol-4-yl)-2-(3-naphthalen-1-yl-2-naphthalen-1-ylmethyl-propionylamino)-propionic acid, 2-diethylamino ethyl ester;

(S)-3-(1H-Imidazol-4-yl)-2-(3-naphthalen-1-yl-2-naphthalen-1-ylmethyl-propionylamino)-propionic acid, 2-morpholin-4-yl-ethyl ester;

(S)-N-[1-(2-Benzyloxy-ethylcarbamoyl)-2-(1H-imidazol-4-yl)-ethyl]-3-naphthalen-1-yl-2-naphthalen-1-ylmethyl-propionamide;

(S)-N-[1-(Carbamoyl-2-(1H-imidazol-4-yl)-ethyl]-3-naphthalen-1-yl-2-naphthalen-1-ylmethyl-propionamide;

(S)-N-[2-(1H-Imidazol-4-yl)-1-(2-imidazol-1-yl-ethylcarbamoyl)-ethyl]-3-naphthalen-1-yl-2-naphthalen-1-ylmethyl-propionamide;

(S)-N-[2-Ethylsulfanyl-ethylcarbamoyl)-2-(1H-imidazol-4-yl)-ethyl]-3-naphthalen-1-yl-2-naphthalen-1-ylmethyl-propionamide;

(S)-N-{2-(1H-Imidazol-4-yl)-1-[2-(1H-imidazol-4-yl)-ethylcarbamoyl]-ethyl}-3-naphthalen-1-yl-2-naphthalen-1-ylmethyl-propionamide;

(S)-N-[2-(1H-Imidazol-4-yl)-1-(3-imidazol-1-yl)-propylcarbamoyl]-ethyl]-3-naphthalen-1-yl-2-naphthalen-1-ylmethyl-propionamide;

(S)-N-[1-(2-Hydroxy-ethylcarbamoyl)-2-(1H-imidazol-4-yl)-ethyl]-3-naphthalen-1-yl-2-naphthalen-1-ylmethyl-propionamide;

(S)-N-[2-(1H-Imidazol-4-yl)-1-isopropylcarbamoyl-ethyl]-3-naphthalen-1-yl-2-naphthalen-1-ylmethyl-propionamide;

(S)-N-[2-(1H-Imidazol-4-yl)-1-(2-morpholin-4-yl-ethylcarbamoyl)-ethyl]-3-naphthalen-1-yl-2-naphthalen-1-ylmethyl-propionamide;

(S)-N-[1-(2-Diethylamino-ethylcarbamoyl)-2-(1H-imidazol-4-yl)-ethyl]-(3-naphthalen-1-yl-2-naphthalen-1-ylmethyl-propionamide;

(S)-N-[2-(1H-Imidazol-4-yl)-1-methylcarbamoyl-ethyl]-3-naphthalen-1-yl-2-naphthalen-1-ylmethyl-propionamide;

(S)-N-[1-Ethylcarbamoyl-2-(1H-Imidazol-4-yl)-ethyl]-3-naphthalen-1-yl-2-naphthalen-1-ylmethyl-propionamide;

(S)-N-{2-(1H-Imidazol-4-yl)-1-[2-(4-sulfamoyl-phenyl)-ethylcarbamoyl]-ethyl}-3-naphthalen-1-yl-2-naphthalen-1-ylmethyl-propionamide;

(S)-2-[3-(Decahydro-naphthalen-1-yl)-2-(decahydro-naphthalen-1-ylmethyl)-propionylamino]-3-(1H-imidazol-4-yl)-propionic acid, methyl ester;

(S)-3-(1H-Imidazol-4-yl)-2-[3-(5,6,7,8-tetrahydro-naphthalen-1-yl)-2-(5,6,7,8-tetrahydro-naphthalen-1-ylmethyl)-propionylamino]-propionic acid, methyl ester;

(S)-N-[1-(2-Benzyloxy-ethylcarbamoyl)-2-(1H-imidazol-4-yl)-ethyl]-3-(5,6,7,8-tetrahydro-naphthalen-1-yl)-2-(5,6,7,8-tetrahydro-naphthalen-1-ylmethyl)-propionamide;

(S)-2-(3-Benzo[b]thiophen-3-yl-2-benzo[b]thiophen-3-ylmethyl-propionylamino)-3-(1H-imidazol-4-yl)-propionic acid, methyl ester;

(S)-3-(1H-Imidazol-4-yl)-2-(3-naphthalen-1-yl-2-naphthalen-1-ylmethyl-propionylamino)-thiopropionic acid, S-(2-acetylamino-ethyl) ester;

(S)-N-[1-(2-Cyano-ethylcarbamoyl)-2-(1H-imidazol-4-yl)-ethyl]-3-naphthalen-1-yl-2-naphthalen-1-ylmethyl-propionamide;

(S)-3-(1H-Imidazol-4-yl)-2-(3-naphthalen-1-yl-2-naphthalen-1-ylmethyl-propionylamino)-propionic acid, 2-hydroxy-ethyl ester;

(S)-N-[1-Dimethylcarbamoyl-2-(1H-imidazol-4-yl)-ethyl]-3-naphthalen-1-yl-2-naphthalen-1-ylmethyl-propionamide;

(S)-3-(1H-Imidazol-4-yl)-2-(3-naphthalen-1-yl-2-naphthalen-1-ylmethyl-propionylamino)-propionic acid, but-3-ynyl ester;

(S)-2-[3-(Decahydro-naphthalen-1-yl)-2-(decahydro-naphthalen-1-ylmethyl)-propionylamino]-3-(1H-imidazol-4-yl)-propionic acid, 2-cyano-ethyl ester;

(S)-N-[2-(1H-Imidazol-4-yl)-1-propylcarbamoyl-ethyl]3-naphthalen-1-yl-2-naphthalen-1-ylmethyl-propionamide;

(S)-3-(1H-Imidazol-4-yl)-2-(3-naphthalen-1-yl-2-naphthalen-1-ylmethyl-propionylamino)-propionic acid, 2-imidazol-1-yl-ethyl ester;

(S)-3-(1H-Imidazol-4-yl)-2-(3-naphthalen-1-yl-2-naphthalen-1-ylmethyl-propionylamino)-propionic acid, but-3-enyl ester;

(S)-3-(1H-Imidazol-4-yl)-2-[3-(5,6,7,8-tetrahydro-naphthalen-1-yl)-2-(5,6,7,8-tetrahydro-naphthalen-1-ylmethyl)-propionylamino]-propionic acid, 2-cyano-ethyl ester;

(S)-N-[2-(1H-imidazol-4-yl)-1-phenethylcarbamoyl-ethyl]-3-naphthalen-1-yl-2-naphthalen-1-ylmethyl-propionamide;

(S)-3-(1H-Imidazol-4-yl)-2-[methyl-(3-naphthalen-1-yl-2-naphthalen-1-ylmethyl-propiony)-amino]-propionic acid, methyl ester;

(S)-N-[1-Hydroxymethyl-2-(1H-imidazol-4-yl)-ethyl]-3-naphthalen-1-yl-2-naphthalen-1-ylmethyl-propionamide;

(S)-3-[1H-Imidazol-4-yl)-2-(3-naphthalen-1-yl-2-naphthalen-1-ylmethyl-propionylamino)-propionic acid, phenethyl ester;

(S)-3-[1H-Imidazol-4-yl)-2-(3-naphthalen-1-yl-2-naphthalen-1-ylmethyl-propionylamino)-propionic acid, 3-cyano-propyl ester;

(S)-3-(1H-Imidazol-4-yl)-2-(3-naphthalen-1-yl-2-naphthalen-1-ylmethyl-propionylamino)-propionic acid, 3-methyl-but-2-enyl ester;

(S)-3-(1H-Imidazol-4-yl)-2-(3-naphthalen-1-yl-2-naphthalen-1-ylmethyl-propylamino)-propionic acid, methyl ester;

(S)-3-(1H-Imidazol-4-yl)-2-(3-naphthalen-1-yl-2-naphthalen-1-ylmethyl-propionylamino)-propionic acid, methoxycarbonylmethyl ester;

(S)-3-(1H-Imidazol-4-yl)-2-(3-naphthalen-1-yl-2-naphthalen-1-ylmethyl-propionylamino)-propionic acid, cyanomethyl ester;

(S)-3-(1H-Imidazol-4-yl)-2-(3-naphthalen-1-yl-2-naphthalen-1-ylmethyl-propionylamino)-propionic acid, 2-(2-hydroxy-ethyldisulfanyl)-ethyl ester;

(S)-3-(3-Methoxymethyl-3H-imidazol-4-yl)-2-(3-naphthalen-1-yl-2-naphthalen-1-ylmethyl-propionylamino)-propionic acid, methyl ester;

(S)-3-(1H-Imidazol-4-yl)-2-(3-naphthalen-1-yl-2-naphthalen-1-ylmethyl-propionylamino)-propionic acid, 1-cyano-ethyl ester;

(S)-3-(1H-Imidazol-4-yl)-2-(3-naphthalen-1-yl-2-naphthalen-1-ylmethyl-propylamino)-propan-1-ol;

(S)-3-(1H-Imidazol-4-yl)-N-methyl-2-(3-naphthalen-1-yl-2-naphthalen-1-ylmethyl-propylamino)-propionamide;

(S)-N-[1-Methylcarbamoyl-2-(3-methyl-3H-imidazol-4-yl)-ethyl]-3-naphthalen-1-yl-2-naphthalen-1-ylmethyl-propionamide; and (S)-2-(2-Benzyl-3-naphthalen-1-yl-propionylamino)-3-(1H-imidazol-4-yl)-propionic acid, methyl ester.

5. A method of treating tissue proliferative diseases comprising administering to a host suffering therefrom a therapeutically effective amount of a compound according to claim 1 in unit dosage form.

6. A method of treating cancer comprising administering to a host suffering therefrom a therapeutically effective amount of a compound according to claim 1 in unit dosage form.

7. A method of treating restenosis comprising administering to a host suffering therefrom a therapeutically effective amount of a compound according to claim 1 in unit dosage form.

8. A method of treating psoriasis comprising administering to a host suffering therefrom a therapeutically effective amount of a compound according to claim 1 in unit dosage form.

9. A method of treating viral infections comprising administering to a host suffering therefrom a therapeutically effective amount of a compound according to claim 1 in unit dosage form.

10. A pharmaceutical composition comprising a compound according to claim 1 in admixture with a pharmaceutically acceptable excipient, diluent, or carrier.

11. A pharmaceutical composition adapted for administration as an antiproliferative agent comprising a therapeutically effective amount of a compound according to claim 1 in admixture with a pharmaceutically acceptable excipient, diluent, or carrier.

12. A pharmaceutical composition adapted for administration as an anticancer agent, or restenosis inhibiting agent or antipsoriasis agent or antiviral agent comprising a therapeutically effective amount of a compound according to claim 1 in admixture with a pharmaceutically acceptable excipient, diluent, or carrier.

13. A method of treating tissue proliferative diseases, cancer, restenosis, psoriasis and viral infections, comprising administering to a host suffering therefrom a therapeutically effective amount of a compound of formula

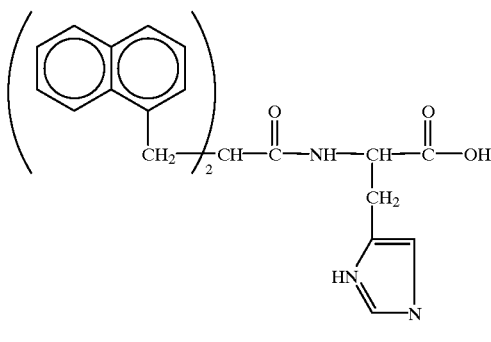

and corresponding isomers thereof; or a pharmaceutically acceptable salt thereof in unit dosage form.

14. A method for preparing a compound having the Formula Ia

Ia

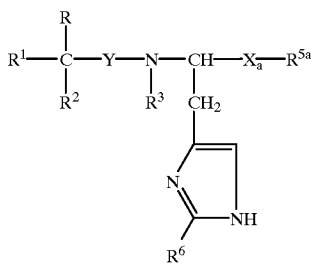

wherein R is hydrogen or alkyl;
$R^1$ and $R^2$ are the same or different and are selected from the group consisting of:

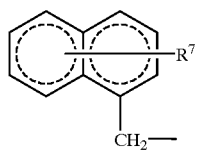

wherein the bicyclic ring is either aromatic, or partially or completely saturated, and $R^7$ are 1 to 3 substituents selected from the group consisting of:

hydrogen,
alkyl,
alkenyl,
alkoxy,
thioalkoxy,
hydroxy,
mercapto,
halogen,
nitro,

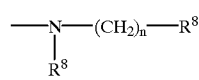

wherein $R^8$ and $R^9$ are the same or different and are selected from the group consisting of:
hydrogen,
alkyl, or $R^8$ and $R^9$ are taken together with N to form a 5- or 6-membered ring which does or does not contain a heteroatom selected from the group consisting of: S, O, and N—$R^{10}$ wherein $R^{10}$ is hydrogen or alkyl, and
n is zero or an integer of one to four,

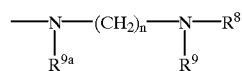

wherein $R^{9a}$ is hydrogen or alkyl, and $R^8$, $R^9$, and n are as defined above, and

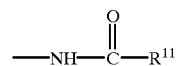

wherein $R^{11}$ is selected from the group consisting of:
hydrogen,
alkyl, and
aryl,

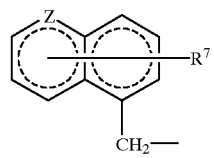

wherein the bicyclic ring is either aromatic, or partially or completely saturated, and Z is selected from the group consisting of:
$NR^{12}$ wherein $R^{12}$ is hydrogen, alkyl or

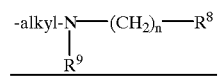

wherein $R^8$, $R^9$, and n are as defined above, or $R^{12}$ is absent,
O,
S,
SO, and
$SO_2$, and
Z is at other positions in the bicyclic ring system provided that when the bicyclic ring is aromatic, Z is not at the point of attachment of the $CH_2$ unit and $R^{12}$ is absent, and $R^7$ is as defined above,

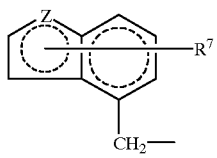

wherein the bicyclic ring is either aromatic, or partially or completely saturated, and Z and $R^7$ are as defined above and $R^{12}$ may be present,

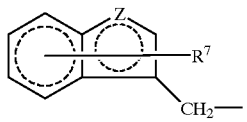

wherein the bicyclic ring is either aromatic, or partially or completely saturated, and Z and $R^7$ are as defined above and $R^{12}$ is present,

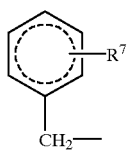

wherein the monocyclic ring is either aromatic, or partially or completely saturated, and $R^7$ is as defined above with the proviso that $R^1$ and $R^2$ are not both a monocyclic ring, and

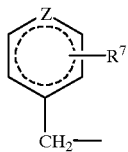

wherein the monocyclic ring is either aromatic, or partially or completely saturated, and $R^7$ and Z are as defined above with the proviso that $R^1$ and $R^2$ are not both a monocyclic ring;
$R^3$ is hydrogen or alkyl;
$X_a$ is

Y is

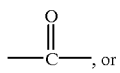, or

$R^{5a}$ is selected from the group consisting of:
—$OR^{14a}$ wherein $R^{14a}$ is selected from the group consisting of:
alkyl,
alkenyl,
alkynyl,
cycloalkyl,
cycloalkylalkyl,
haloalkyl,
hydroxyalkyl,
mercaptoalkyl,
cyanoalkyl,
nitroalkyl,
alkoxyalkyl,
arylalkyl,
heteroarylalkyl,
benzyloxyalkyl,
thioalkoxyalkyl,
acetamidoalkyl,
$HOCH_2CH_2$—S—S—$CH_2CH_2$—,

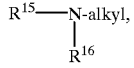

wherein $R^{15}$ and $R^{16}$ are the same or different and are selected from the group consisting of:
hydrogen,
allyl or $R^{15}$ and $R^{16}$ are taken together with N to form a 5- or 6-membered ring which does or does not contain a heteroatom selected from the group consisting of: S, O, and N—$R^{10}$ wherein $R^{10}$ is as defined above,
$HO_2C$-alkyl,
alkyl-$O_2C$-alkyl, and

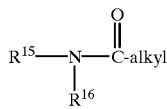

wherein $R^{15}$ and $R^{16}$ are as defined above,
—S—$R^{14a}$ wherein $R^{14a}$ is as defined above;

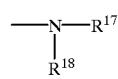

wherein $R^{17}$ and $R^{18}$ are the same or different and are selected from the group consisting of:
hydrogen,
alkyl,
alkenyl,
alkynyl,
cyanoallyl,
hydroxyalkyl,
alkoxyalkyl,
arylalkyl,
heteroarylalkyl,
benzyloxyalkyl,
cycloalkyl,
cycloalkylalkyl, haloalkyl,
mercaptoalkyl,
nitroalkyl,
thioalkoxyalkyl,
acetamidoalkyl,

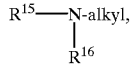

wherein $R^{15}$ and $R^{16}$ are the same or different and are selected from the group consisting of:
hydrogen,
alkyl or $R^{15}$ and $R^{16}$ are taken together with N to form a 5- or 6-membered ring which does or does not contain a heteroatom selected from the group consisting of: S, O, and N—$R^{10}$ wherein $R^{10}$ is as defined above, or $R^{17}$ and $R^{18}$ are taken together with N to form a 5- or 6-membered ring which does or does not contain a heteroatom selected from the group consisting of: S, O, and N—$R^{10}$ wherein $R^{10}$ is as defined above,
—NH—$OR^{10}$ wherein $R^{10}$ is as defined above,
alkyl,
alkenyl, and
arylalkyl; and
$R^6$ is hydrogen,
—SR where R is as defined above,
—OR where R is as defined above, or

wherein R and $R^a$ may be the same or different and are as defined above for R; or corresponding isomers thereof; or a pharmaceutically acceptable salt thereof comprising reacting a compound of Formula II

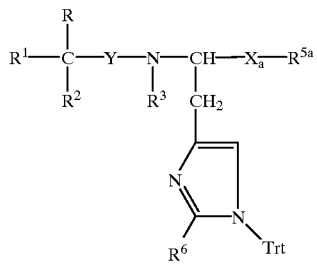

II wherein Trt is $(C_6H_5)_3$—C— and R, $R^1$, $R^2$, $R^3$, $X_a$, Y, $R^{5a}$, and $R^6$ are as defined above with an a to afford a compound of Formula Ia.H

* * * * *